(12) United States Patent
Gravestock et al.

(10) Patent No.: US 7,396,847 B2
(45) Date of Patent: Jul. 8, 2008

(54) OXAZOLIDINONE AND/OR ISOXAZOLINE AS ANTIBACTERIAL AGENTS

(75) Inventors: Michael Barry Gravestock, Waltham, MA (US); Neil James Hales, Cheshire (GB); Michael Lingard Swain, Cheshire (GB); Sheila Irene Hauck, Waltham, MA (US); Stuart Dennett Mills, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 245 days.

(21) Appl. No.: 10/489,266

(22) PCT Filed: Sep. 9, 2002

(86) PCT No.: PCT/GB02/04120

§ 371 (c)(1),
(2), (4) Date: Sep. 9, 2004

(87) PCT Pub. No.: WO03/022824

PCT Pub. Date: Mar. 20, 2003

(65) Prior Publication Data

US 2005/0107435 A1    May 19, 2005

(30) Foreign Application Priority Data

Sep. 11, 2001 (GB) .................................. 0121942.7
Jul. 4, 2002 (GB) .................................. 0215420.1

(51) Int. Cl.
A61K 31/42 (2006.01)
C07D 263/02 (2006.01)
C07D 263/00 (2006.01)
C07D 261/02 (2006.01)

(52) U.S. Cl. .................. 514/374; 514/376; 514/378; 548/215; 548/225; 548/240

(58) Field of Classification Search ............... 514/374, 514/376, 378; 548/215, 225, 240
See application file for complete search history.

(56) References Cited

U.S. PATENT DOCUMENTS 5,043,443 A * 8/1991 Carlson et al. .............. 544/112

FOREIGN PATENT DOCUMENTS

| DE | 10034624 | 1/2002 |
|---|---|---|
| DE | 10034625 | 1/2002 |
| EP | 0 352 781 A2 | 1/1990 |
| JP | 2003335762 A2 | 11/2003 |
| WO | WO-93/23384 A1 | 11/1993 |
| WO | WO-97/14690 A1 | 4/1997 |
| WO | WO-97/27188 A1 | 7/1997 |
| WO | WO-97/30995 A1 | 8/1997 |
| WO | WO-97/31917 A1 | 9/1997 |
| WO | WO-97/43280 A1 | 11/1997 |
| WO | WO-98/01446 A1 | 1/1998 |
| WO | WO-98/01447 A1 | 1/1998 |
| WO | WO-99/10343 A1 | 3/1999 |
| WO | WO-99/11642 A1 | 3/1999 |
| WO | WO-99/10342 A1 | 4/1999 |
| WO | WO-99/28317 A1 | 6/1999 |
| WO | WO-99/33839 A1 | 7/1999 |
| WO | WO-99/63937 A2 | 12/1999 |
| WO | WO-99/64416 A2 | 12/1999 |
| WO | WO-99/64417 A2 | 12/1999 |
| WO | WO-00/21960 A1 | 4/2000 |
| WO | WO-01/40222 A1 | 6/2001 |
| WO | WO-01/40236 A2 | 6/2001 |
| WO | WO-01/81350 A1 | 11/2001 |
| WO | WO-01/94342 A1 | 12/2001 |
| WO | WO-02/051819 A2 | 7/2002 |
| WO | WO-02/080841 A2 | 10/2002 |
| WO | WO-02/081468 A1 | 10/2002 |
| WO | WO-02/081469 A1 | 10/2002 |
| WO | WO-02/081470 A1 | 10/2002 |
| WO | WO-02/096890 A2 | 12/2002 |
| WO | WO-02/096916 A1 | 12/2002 |
| WO | WO-02/096917 A1 | 12/2002 |
| WO | WO-02/096918 A1 | 12/2002 |
| WO | WO-03/006440 A2 | 1/2003 |
| WO | WO-03/011859 A2 | 2/2003 |
| WO | WO-03/031441 A1 | 4/2003 |
| WO | WO-03/031443 A1 | 4/2003 |
| WO | WO-03/035073 A1 | 5/2003 |
| WO | WO-03/035648 A1 | 5/2003 |
| WO | WO-03/072575 A1 | 9/2003 |
| WO | WO-03/072576 A2 | 9/2003 |
| WO | WO-2004/029066 A2 | 4/2004 |

OTHER PUBLICATIONS

U.S. Appl. No. 10/536,686.*
Exp. Opin. Ther. Patents (1999) 9(5): 625-633.*
Junior copending U.S. Appl. No. 10/536,686.*
Gregory, W.A., et al., "Antibacterials. Synthesis and Structure-Activity Studies of 3-Aryl-2-oxooxazolidines. 2. The 'A' Group," J. Med. Chem., 33, 2569-2578 (1990).
Park, C.H., et al., "Antibacterials. Synthesis and Structure-Activity Studies of 3-Aryl-2-oxooxazolidines. 4. Multiply-Substituted Aryl Derivatives," J. Med. Chem., 35, 1156-1165 (1992).
Pae, A.N., et al., "Synthesis and In Vitro Activity of New Oxazolidinone Antibacterial Agents Having Substituted Isoxazoles," Bioorganic & Medicinal Chemistry Letters, 9, 2679-2684 (1999).

* cited by examiner

Primary Examiner—Joseph McKane
Assistant Examiner—Susannah Chung
(74) Attorney, Agent, or Firm—Morgan, Lewis & Bockius LLP

(57) ABSTRACT

Compounds of the formula (I), or a pharmaceutically-acceptable salt, or an in-vivo-hydrolysable ester thereof,

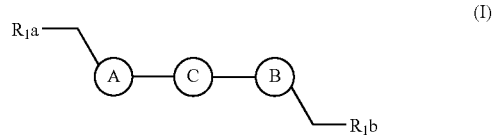

(I)

and compounds as shown in (I) wherein C is for example

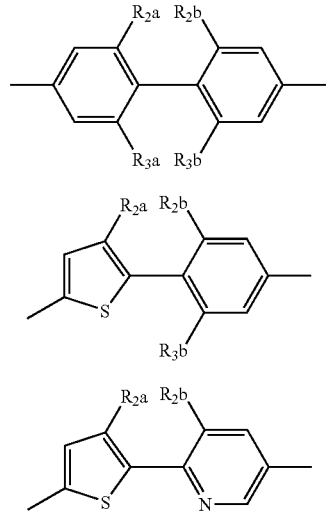

D

E

F wherein A and B are independently selected from

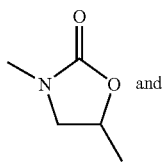

i)

and

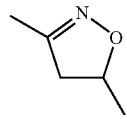

ii)

-continued $R_2a$ to $R_3b$ are independently selected from hydrogen and fluorine;

$R_1a$ and $R_1b$ are independently selected from, for example, hydroxy, —NHC(=W)$R_4$,

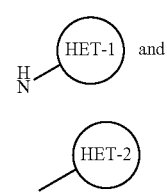

a)

and b)

wherein W is O or S; $R_4$ is, for example, hydrogen, amino, (1-4C)alkyl; HET-1 is, for example, a C-linked 5-membered heteroaryl ring; HET-2 is, for example, an N-linked 5-membered, fully or partially unsaturated heterocyclic ring; are useful as antibacterial agents; and processes for their manufacture and pharmaceutical compositions containing them are described.

6 Claims, No Drawings

OXAZOLIDINONE AND/OR ISOXAZOLINE AS ANTIBACTERIAL AGENTS

CROSS-REFERENCE TO RELATED APPLICATIONS

This application is a national stage filing under 35 U.S.C. 371 of International Application No. PCT/GB02/04120, filed Sep. 9, 2002, which claims priority from United Kingdom Patent Application No. 0121942.7, filed Sep. 11, 2001, and United Kingdom Patent Application No. 0215420.1, filed Jul. 4, 2002, the specifications of which are incorporated by reference herein. International Application No. PCT/GB02/04109 was published under PCT Article 21(2) in English.

The present invention relates to antibiotic compounds and in particular to antibiotic compounds containing substituted oxazolidinone and/or isoxazoline rings. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded as effective against both Gram-positive and certain Gram-negative pathogens.

Gram-positive pathogens, for example *Staphylococci, Enterococci, Streptococci* and mycobacteria, are particularly important because of the development of resistant strains which are both difficult to treat and difficult to eradicate from the hospital environment once established. Examples of such strains are methicillin resistant *staphylococcus* (MRSA), methicillin resistant coagulase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens. There is also now increasing resistance appearing towards agents such as β-lactams, quinolones and macrolides used for the treatment of upper respiratory tract infections, also caused by certain Gram negative strains including *H. influenzae* and *M. catarrhalis*.

Certain antibacterial compounds containing an oxazolidinone ring have been described in the art (for example, Walter A. Gregory et al in J. Med. Chem. 1990, 33, 2569-2578 and 1989, 32(8), 1673-81; Chung-Ho Park et al in J. Med. Chem. 1992, 35, 1156-1165). Bacterial resistance to known antibacterial agents may develop, for example, by (i) the evolution of active binding sites in the bacteria rendering a previously active pharmacophore less effective or redundant, and/or (ii) the evolution of means to chemically deactivate a given pharmacophore, and/or (iii) the evolution of efflux pathways. Therefore, there remains an ongoing need to find new antibacterial agents with a favourable pharmacological profile, in particular for compounds containing new, more potent, pharmacophores.

We have discovered a class of potentially bipharmacophoric antibiotic compounds containing two substituted oxazolidinone and/or isoxazoline rings which has useful activity against Gram-positive pathogens including MRSA and MRCNS and, in particular, against various strains exhibiting resistance to vancomycin and/or linezolid and against *E. faecium* strains resistant to both aminoglycosides and clinically used β-lactams, but also to fastidious Gram negative strains such as *H. influenzae, M. catarrhalis, mycoplasma* spp. and *chlamydial* strains. We use the term 'bipharmacophoric' to indicate that the two substituted oxazolidinone and/or isoxazoline pharmacophores may independently bind at pharmacophore binding sites where the sites may be similar or different, where the similar or different sites may be occupied simultaneously or not simultaneously within a single organism, or where the relative importance of different binding modes to the similar or different sites may vary between two organisms of different genus.

Accordingly the present invention provides a compound of the formula (I), or a pharmaceutically-acceptable salt, or an in-vivo-hydrolysable ester thereof,

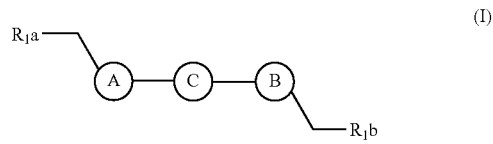

(I)

wherein in (I)C is a biaryl moiety C'-C"

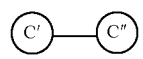

where C' and C" are independently aryl or heteroaryl rings such that the central fragment C is represented by any one of the groups D to L below:

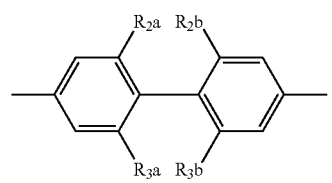

D

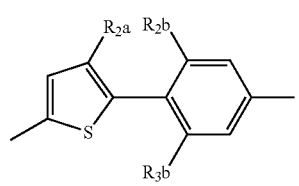

E

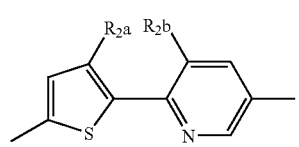

F

-continued

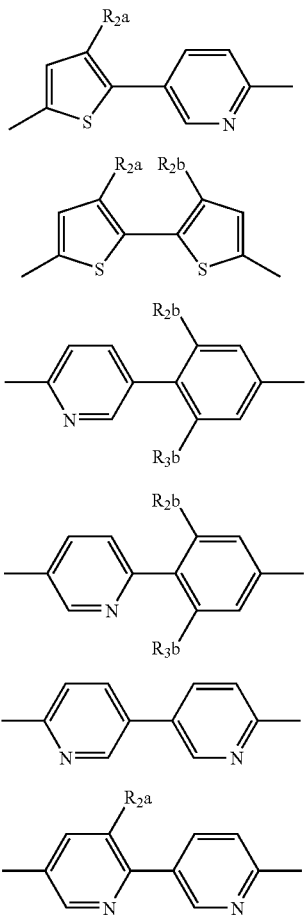

wherein the groups D to L may be attached to rings A and B in either orientation;
wherein A and B are independently selected from

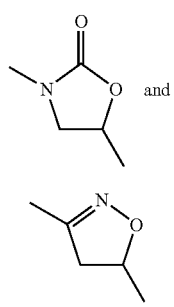

wherein i) and/or ii) are linked as shown in (I) via the 3-position to group C and substituted in the 5-position as shown in (I) by —CH$_2$—R$_1$a and —CH$_2$—R$_1$b;
R$_2$a, R$_2$b, R$_3$a and R$_3$b are independently hydrogen or fluorine;
R$_1$a and R$_1$b are independently selected from hydroxy, —OSi(tri-(1-6C)alkyl) (wherein the 3 (1-6C)alkyl groups are independently selected from all possible (1-6C)alkyl groups), —NR$_5$C(=W)R$_4$, —OC(=O)R$_4$,

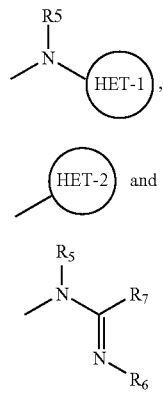

wherein W is O or S;
R$_4$ is hydrogen, amino, (1-8C)alkyl, —NHR$_{12}$, —N(R$_{12}$)(R$_{13}$), —OR$_{12}$ or —SR$_{12}$, (2-4C)alkenyl, (1-8C)alkylaryl, mono-, di-, tri- and per-halo(1-8C)alkyl, —(CH$_2$)$_p$(3-6C)cycloalkyl or —(CH$_2$)p(3-6C)cycloalkenyl wherein p is 0, 1 or 2;
wherein in a) HET-1 is a C-linked 5-membered heteroaryl ring containing 2 to 4 heteroatoms independently selected from N, O and S, which ring is optionally substituted on an available carbon atom by 1 or 2 substituents independently selected from (1-4C)alkyl, (2-4C)alkenyl, (3-6C)cycloalkyl, amino, (1-4C)alkylamino, di-(1-4C)alkylamino, (1-4C)alkylthio, (1-4C)alkoxy, (1-4C)alkoxycarbonyl, halogen and cyano and/or on an available nitrogen atom (provided that the ring is not thereby quaternised) by (1-4C)alkyl; or
HET-1 is a C-linked 6-membered heteroaryl ring containing 2 or 3 nitrogen heteroatoms, which ring is optionally substituted on any available C atom by 1, 2 or 3 substituents independently selected from (1-4C)alkyl, (2-4C)alkenyl, (3-6C)cycloalkyl, amino, (1-4C)alkylamino, di-(1-4C)alkylamino, (1-4C)alkylthio, (1-4C)alkoxy, (1-4C)alkoxycarbonyl, halogen and cyano and/or on an available nitrogen atom (provided that the ring is not thereby quaternised) by (1-4C)alkyl; wherein in b)
HET-2 is an N-linked 5-membered, fully or partially unsaturated heterocyclic ring, containing either (i) 1 to 3 further nitrogen heteroatoms or (ii) a further heteroatom selected from O and S together with an optional further nitrogen heteroatom; which ring is optionally substituted on a C atom by an oxo or thioxo group; and/or which ring is optionally substituted on any available C atom by 1, 2 or 3 substituents independently selected from (1-4C)alkyl, (2-4C)alkenyl, (3-6C)cycloalkyl, amino, (1-4C)alkylamino, di-(1-4C)alkylamino, (1-4C)alkylthio, (1-4C)alkoxy, (1-4C)alkoxycarbonyl, halogen and cyano and/or on an available nitrogen atom (provided that the ring is not thereby quaternised) by (1-4C)alkyl; or HET-2 is an N-linked 6-membered di-hydro-heteroaryl ring containing up to three nitrogen heteroatoms in total (including the linking heteroatom), which ring is substituted on a suitable C atom by oxo or thioxo and/or which ring is optionally substituted on any available C atom by 1, 2 or 3 substituents independently selected from (1-4C)alkyl, (2-4C)alkenyl, (3-6C)cycloalkyl, amino, (1-4C)alkylamino, di-(1-4C)alkylamino, (1-4C)alkylthio, (1-4C)alkoxy, (1-4C)alkoxycarbonyl, halogen and cyano and/or on an available nitrogen atom (provided that the ring is not thereby quaternised) by (1-4C)alkyl;

and wherein at each occurrence, alkyl, alkenyl, cycloalkyl cycloalkenyl in substituents on HET-1 and HET-2, or in $R_4$ is optionally substituted with one, two, three or more F, Cl or CN; wherein in c)

$R_5$ is hydrogen, (3-6C)cycloalkyl, phenyloxycarbonyl, tert-butoxycarbonyl, fluorenyloxycarbonyl, benzyloxycarbonyl, (1-6C)alkyl (optionally substituted by cyano or (1-4C)alkoxycarbonyl), —$CO_2R_8$, —C(=O)$R_8$, —C(=O)$SR_8$, —C(=S)$R_8$, P(O)($OR_9$)($OR_{10}$) and —$SO_2R_{11}$, wherein $R_8$, $R_9$, $R_{10}$ and $R_{11}$ are as defined hereinbelow;

$R_6$ is cyano, —$COR_{12}$, —$COOR_{12}$, —$CONHR_{12}$, —CON($R_{12}$)($R_{13}$), —$SO_2R_{12}$, —$SO_2NHR_{12}$, —$SO_2N(R_{12})(R_{13})$ or $NO_2$, wherein $R_{12}$ and $R_{13}$ are as defined hereinbelow;

$R_7$ is hydrogen, amino, (1-8C)alkyl, —$NHR_{12}$, —$N(R_{12})(R_{13})$, —$OR_{12}$ or —$SR_{12}$, (2-4C)alkenyl, (1-8C)alkylaryl, mono-, di-, tri- and per-halo(1-8C)alkyl, —$(CH_2)_p$(3-6C)cycloalkyl or —$(CH_2)p$(3-6C)cycloalkenyl wherein p is 0, 1 or 2;

$R_8$ is hydrogen, (3-6C)cycloalkyl, phenyl, benzyl, (1-5C)alkanoyl, (1-6C)alkyl (optionally substituted by substituents independently selected from (1-5C)alkoxycarbonyl, hydroxy, cyano, up to 3 halogen atoms and —$NR_{14}R_{15}$ (wherein $R_{14}$ and $R_{15}$ are independently selected from hydrogen, phenyl (optionally substituted with one or more substituents selected from halogen, (1-4C)alkyl and (1-4C)alkyl substituted with one, two, three or more halogen atoms) and (1-4C)alkyl (optionally substituted with one, two, three or more halogen atoms), or for any $N(R_{14})(R_{15})$ group, $R_{14}$ and $R_{15}$ may additionally be taken together with the nitrogen atom to which they are attached to form an unsubstituted or substituted pyrrolidinyl, piperidinyl or morpholinyl group);

$R_9$ and $R_{10}$ are independently selected from hydrogen and (1-4C)alkyl;

$R_{11}$ is (1-4C)alkyl or phenyl;

$R_{12}$ and $R_{13}$ are independently selected from hydrogen, phenyl (optionally substituted with one or more substituents selected from halogen, (1-4C)alkyl and (1-4C)alkyl substituted with one, two, three or more halogen atoms) and (1-4C)alkyl (optionally substituted with one, two, three or more halogen atoms), or for any $N(R_{12})(R_{13})$ group, $R_{12}$ and $R_{13}$ may additionally be taken together with the nitrogen atom to which they are attached to form an unsubstituted or substituted pyrrolidinyl, piperidinyl or morpholinyl group;

provided that, when group C is group I or group J and both groups A and B are oxazolidinones and the oxazolidinone (A or B) that is linked to the pyridyl group in C bears a substitutuent ($R_1$a-$CH_2$ or $R_1$b-$CH_2$ respectively) that is either an hydroxymethyl group or an acetoxymethyl group then the oxazolidinone (B or A) linked to the phenyl group in C is not substituted by an acetamidomethyl group ($R_1$b-$CH_2$ or $R_1$a-$CH_2$ respectively).

A further aspect of the present invention provides a compound of the formula (I), or a pharmaceutically-acceptable salt, or an in-vivo-hydrolysable ester thereof, wherein, in groups D to L, $R_2$a, $R_2$b, $R_3$a and $R_3$b are:

independently hydrogen or fluorine when attached to a phenyl ring, and hydrogen when attached to a thienyl or pyridyl ring;

$R_1$a and $R_1$b are independently selected from hydroxy, —NHC(=W)$R_4$, —OC(=O)$R_4$,

a)

and b)

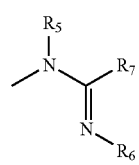

c)

wherein W is O or S;

$R_4$ is hydrogen, amino, (1-4C)alkyl, —NH(1-4C)alkyl, —N(di-(1-4C)alkyl), —O(1-4C)alkyl or —S(1-4C)alkyl, (2-4C)alkenyl, —$(CH_2)_p$(3-6C)cycloalkyl or —$(CH_2)_p$(3-6C)cycloalkenyl wherein p is 0, 1 or 2;

wherein in a) HET-1 is a C-linked 5-membered heteroaryl ring containing 2 to 4 heteroatoms independently selected from N, O and S, which ring is optionally substituted on an available carbon atom by 1 or 2 substituents independently selected from (1-4C)alkyl, (2-4C)alkenyl, (3-6C)cycloalkyl, amino, (1-4C)alkylamino, di-(1-4C)alkylamino, (1-4C)alkylthio, (1-4C)alkoxy, (1-4C)alkoxycarbonyl, halogen, cyano and trifluoromethyl and/or on an available nitrogen atom (provided that the ring is not thereby quaternised) by (1-4C)alkyl; or HET-1 is a C-linked 6-membered heteroaryl ring containing 2 or 3 nitrogen heteroatoms, which ring is optionally substituted on any available C atom by 1, 2 or 3 substituents independently selected from (1-4C)alkyl, (24C)alkenyl, (3-6C)cycloalkyl, amino, (1-4C)alkylamino, di-(1-4C)alkylamino, (1-4C)alkylthio, (1-4C)alkoxy, (1-4C)alkoxycarbonyl, halogen, cyano and trifluoromethyl and/or on an available nitrogen atom (provided that the ring is not thereby quaternised) by (1-4C)alkyl; wherein in b)

HET-2 is an N-linked 5-membered, fully or partially unsaturated heterocyclic ring, containing either (i) 1 to 3 further nitrogen heteroatoms or (ii) a further heteroatom selected from O and S together with an optional further nitrogen heteroatom; which ring is optionally substituted on a C atom by an oxo or thioxo group; and/or which ring is optionally substituted on any available C atom by 1, 2 or 3 substituents independently selected from (1-4C)alkyl, (2-4C)alkenyl, (3-6C)cycloalkyl, amino, (1-4C)alkylamino, di-(1-4C)alkylamino, (1-4C)alkylthio, (1-4C)alkoxy, (1-4C)alkoxycarbonyl, halogen, cyano and trifluoromethyl and/or on an available nitrogen atom (provided that the ring is not thereby quaternised) by (1-4C)alkyl; or HET-2 is an N-linked 6-membered di-hydro-heteroaryl ring containing up to three nitrogen heteroatoms in total (including the linking heteroatom), which ring is substituted on a suitable C atom by oxo or thioxo and/or which ring is optionally substituted on any available C atom by 1, 2 or 3 substituents independently selected from (1-4C)alkyl, (2-4C)alkenyl, (3-6C)cycloalkyl, amino, (1-4C)alkylamino, di-(1-4C)alkylamino, (1-4C)alkylthio, (1-4C)alkoxy, (1-4C)alkoxycarbonyl, halogen, cyano and trifluoromethyl and/or on an available nitrogen atom (provided that the ring is not thereby quaternised) by (1-4C)alkyl;

and wherein at each occurrence, alkyl, alkenyl, cycloalkyl cycloalkenyl in substituents on HET-1 and HET-2, or in $R_4$ is optionally substituted with one or more F, Cl or CN; wherein in c)

$R_5$ is hydrogen, (3-6C)cycloalkyl, phenyloxycarbonyl, tert-butoxycarbonyl, fluorenyloxycarbonyl, benzyloxycarbonyl, (1-6C)alkyl (optionally substituted by cyano or (1-4C) alkoxycarbonyl), —$CO_2R_8$, —C(=O)$R_8$, —C(=O)$SR_8$, —C(=S)$R_8$, P(O)(OR$_9$)(OR$_{10}$) and —$SO_2R_{11}$, wherein $R_8$, $R_9$, $R_{10}$ and $R_{11}$ are as defined hereinbelow;

$R_6$ is cyano, —$COR_{12}$, —$COOR_{12}$, —$CONHR_{12}$, —$CON(R_{12})(R_{13})$, —$SO_2R_{12}$, —$SO_2NHR_{12}$, —$SO_2N(R_{12})(R_{13})$ or $NO_2$, wherein $R_{12}$ and $R_{13}$ are as defined hereinbelow;

$R_7$ is hydrogen, (1-8C)alkyl, —$OR_{12}$, —$SR_{12}$, amino, $NHR_{12}$, $N(R_{12})(R_{13})$, (1-8C)alkylaryl or mono-, di-, tri- and per-halo(1-8C)alkyl;

$R_8$ is hydrogen, (3-6C)cycloalkyl, trifluoromethyl, phenyl, benzyl, (1-5C)alkanoyl, (1-6C)alkyl (optionally substituted by substituents independently selected from (1-5C) alkoxycarbonyl, hydroxy, cyano, up to 3 halogen atoms and —$NR_{14}R_{15}$ (wherein $R_{14}$ and $R_{15}$ are independently selected from hydrogen, phenyl and (1-4C)alkyl));

$R_9$ and $R_{10}$ are independently selected from hydrogen and (1-4C)alkyl;

$R_{11}$ is (1-4C)alkyl or phenyl;

$R_{12}$ and $R_{13}$ are independently selected from hydrogen, alkyl and aryl, or for any $N(R_{12})(R_{13})$ group, $R_{12}$ and $R_{13}$ may additionally be taken together with the nitrogen atom to which they are attached to form an unsubstituted or substituted pyrrolidinyl, piperidinyl or morpholinyl group.

In this specification, HET-1 as a C-linked 5-membered heteroaryl ring containing 2 to 4 heteroatoms independently selected from N, O and S, and HET-1 as a C-linked 6-membered heteroaryl ring containing 2 or 3 nitrogen heteroatoms, are fully unsaturated ring systems.

In this specification, HET-2 as an N-linked 5-membered heterocyclic ring may be a fully or partially unsaturated heterocyclic ring, provided there is some degree of unsaturation in the ring.

Particular examples of 5-membered heteroaryl rings containing 2 to 4 heteroatoms independently selected from N, O and S (with no O—O, O—S or S—S bonds) are pyrazole, imidazole, 1,2,3-triazole, 1,2,4-triazole, oxazole, isoxazole, thiazole, 1,2,3-oxadiazole, 1,2,4-oxadiazole, 1,2,5-oxadiazole, 1,3,4-oxadiazole, isothiazole, 1,2,5-thiadiazole, 1,2,4-thiadiazole and 1,2,3-thiadiazole.

Particular examples of 6-membered heteroaryl ring systems containing up to three nitrogen heteroatoms are pyrimidine, pyridazine, pyrazine, 1,2,3-triazine, 1,2,4-triazine and 1,3,5-triazine.

Particular examples of N-linked 5-membered, fully or partially unsaturated heterocyclic rings, containing either (i) 1 to 3 further nitrogen heteroatoms or (ii) a further heteroatom selected from O and S together with an optional further nitrogen heteroatom include, for example, pyrazole, imidazole, 1,2,3-triazole (preferably 1,2,3-triazol-1-yl), 1,2,4-triazole (preferably 1,2,4-triazol-1-yl) and tetrazole (preferably tetrazol-2-yl) and furazan.

Particular examples of N-linked 6-membered di-hydro-heteroaryl rings containing up to three nitrogen heteroatoms in total (including the linking heteroatom) include di-hydro versions of pyrimidine, pyridazine, pyrazine, 1,2,3-triazine, 1,2,4-triazine, 1,3,5-triazine and pyridine.

Particular examples of halogen-substituted alkyl substituents in HET-1 and HET-2 are monofluoromethyl, difluoromethyl and trifluoromethyl.

A particular example of $R_8$ as a halogen-substituted alkyl group is trifluoromethyl.

In this specification the term 'alkyl' includes straight chained and branched structures. For example, (1-4C)alkyl includes propyl and isopropyl. However, references to individual alkyl groups such as "propyl" are specific for the straight chained version only, and references to individual branched chain alkyl groups such as "isopropyl" are specific for the branched chain version only. In this specification, the terms 'alkenyl' and 'cycloalkenyl' include all positional and geometrical isomers. In this specification, the term 'aryl' is an unsubstituted carbocyclic aromatic group, in particular phenyl, 1- and 2-naphthyl.

There follow particular and suitable values for certain substituents and groups referred to in this specification. These values may be used where appropriate with any of the definitions and embodiments disclosed hereinbefore, or hereinafter. For the avoidance of doubt each stated species represents a particular and independent aspect of this invention.

Examples of (1-4C)alkyl include methyl, ethyl, propyl and isopropyl; examples of (1-6C)alkyl include methyl, ethyl, propyl, isopropyl, butyl, tert-butyl, pentyl and hexyl; examples of (2-4C)alkenyl include vinyl, propenyl, allyl, butenyl; examples of (1-4C)alkanoyl include acetyl and propionyl; examples of (1-5C)alkoxycarbonyl include methoxycarbonyl, ethoxycarbonyl, propoxycarbonyl and pentoxycarbonyl; examples of (1-4C)alkoxy include methoxy, ethoxy and propoxy; examples of (1-4C)alkylamino include methylamino, ethylamino and propylamino; examples of di-(1-4C) alkylamino include dimethylamino, methylethylamino and ethylpropylamino; examples of (1-4C)alkylthio include methylthio and ethylthio; examples of (3-6C)cycloalkyl include cyclopropyl, cyclobutyl, cyclopentyl and cyclohexyl; examples of (3-6C)cycloalkenyl include cyclopropenyl, cyclobutenyl, cyclopentenyl and cyclohexenyl; examples of (1-8C)alkylaryl include benzyl; examples of halo groups include fluoro, chloro and bromo.

Suitable pharmaceutically-acceptable salts include acid addition salts such as methanesulfonate, fumarate, hydrochloride, citrate, maleate, tartrate and (less preferably) hydrobromide. Also suitable are salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine, tris-(2-hydroxyethyl) amine, N-methyl d-glucamine and amino acids such as lysine. There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the invention may be administered in the form of a pro-drug which is broken down in the human or animal body to give a compound of the invention. A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the invention or a pharmaceutically-acceptable salt thereof.

Various forms of prodrugs are known in the art, for examples see:

a) Design of Prodrugs, edited by H. Bundgaard, (Elsevier, 1985) and Methods in Enzymology, Vol. 42, p. 309-396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113-191 (1991);
c) H. Bundgaard, Advanced Drug Delivery Reviews, 8, 1-38 (1992);
d) H. Bundgaard, et al., Journal of Pharmaceutical Sciences, 77, 285 (1988); and
e) N. Kakeya, et al., Chem Pharm Bull, 32, 692 (1984).

An in-vivo hydrolysable ester of a compound of the invention or a pharmaceutically-acceptable salt thereof containing hydroxy group is, for example, a pharmaceutically-acceptable ester which is hydrolysed in the human or animal body to produce the parent alcohol.

An in-vivo hydrolysable ester of a compound of the invention or a pharmaceutically-acceptable salt thereof containing a hydroxy group or groups includes inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include (1-10C)alkanoyl, benzoyl, phenylacetyl and substituted benzoyl and phenylacetyl, (1-10C)alkoxycarbonyl (to give alkyl carbonate esters), di-(1-4C)alkylcarbamoyl and N-(di-(1-4C)alkylaminoethyl)-N-(1-4C)alkylcarbamoyl (to give carbamates), di-(1-4C)alkylaminoacetyl and carboxyacetyl. Examples of ring substituents on phenylacetyl and benzoyl include chloromethyl or aminomethyl, (1-4C)alkylaminomethyl and di-((1-4C)alkyl)aminomethyl, and morpholino or piperazino linked from a ring nitrogen atom via a methylene linking group to the 3- or 4-position of the benzoyl ring. Other interesting in-vivo hydrolysable esters include, for example, $R^4C(O)O(1-6C)$alkyl-CO— (wherein $R^4$ is for example, optionally substituted benzyloxy-(1-4C)alkyl, or optionally substituted phenyl; suitable substituents on a phenyl group in such esters include, for example, 4-(1-4C)piperazino-(1-4C)alkyl, piperazino-(1-4C)alkyl and morpholino-(1-4C)alkyl.

Further in-vivo hydrolysable esters include phosphoramidic esters, and also compounds of invention in which any free hydroxy group independently forms a phosphoryl (npd is 1) or phosphiryl (npd is 0) ester of the formula (PD1):

(PD1)

Useful intermediates for the preparation of such esters include compounds containing a group/s of formula (PD1) in which either or both of the —OH groups in (PD1) is independently protected by (1-4C)alkyl (such compounds also being interesting compounds in their own right), phenyl or phenyl-(1-4C)alkyl (such phenyl groups being optionally substituted by 1 or 2 groups independently selected from (1-4C)alkyl, nitro, halo and (1-4C)alkoxy).

Thus, prodrugs containing groups such as (PD1) may be prepared by reaction of a compound of invention containing suitable hydroxy group/s with a suitably protected phosphorylating agent (for example, containing a chloro or dialkylamino leaving group), followed by oxidation (if necessary) and deprotection.

When a compound of invention contains a number of free hydroxy group, those groups not being converted into a prodrug functionality may be protected (for example, using a t-butyl-dimethylsilyl group), and later deprotected. Also, enzymatic methods may be used to selectively phosphorylate or dephosphorylate alcohol functionalities.

Where pharmaceutically-acceptable salts of an in-vivo hydrolysable ester may be formed this is achieved by conventional techniques. Thus, for example, compounds containing a group of formula (PD1) may ionise (partially or fully) to form salts with an appropriate number of counter-ions. Thus, by way of example, if an in-vivo hydrolysable ester prodrug of a compound of invention contains two (PD1) groups, there are four HO—P— functionalities present in the overall molecule, each of which may form an appropriate salt (i.e. the overall molecule may form, for example, a mono-, di-, tri- or tetra-sodium salt).

The compounds of the present invention have a chiral centre at both of the C-5 positions of the oxazolidinone and/or isoxazoline rings. The pharmaceutically active diastereomer is of the formula (IA):

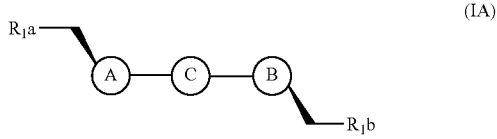

(IA)

The present invention includes the pure diastereomer depicted above (described herein as 'bis (5R)' or mixtures of the bis (5R) and bis (5S) diastereomers, for example a racemic mixture, or diastereomers wherein one ring has the 5R configuration and the other has the 5S ('(5R, 5'S) and (5S, 5'R)'). If a mixture of enantiomers is used (either mixtures of bis (5R) plus bis (5S) or mixtures of (5R, 5'S) plus (5S, 5'R)), a larger amount (depending upon the ratio of the enantiomers) will be required to achieve the same effect as the same weight of the pharmaceutically active enantiomer. The enantiomer depicted above is generally the bis (5R) enantiomer (depending on the nature of $R_1a$, $R_1b$, A and B), although certain compounds (dependant on the nature of $R_1a$, $R_1b$, A and B) are, for example, the bis (5S) enantiomer, or (5R,5'S) enantiomer. To aid understanding, Examples 1 and 2 are shown below; the nature of the side-chain here renders the preferred compound (as shown) to be the bis (5S) and the bis (5R) enantiomer respectively.

EXAMPLE 1

(5S,5S')-N-(3-{4'-[5-(Acetylamino-methyl)-2-oxo-oxazolidin-3-yl]-2,2'-difluoro-biphenyl-4-yl}-2-oxo-oxazolidin-5-ylmethyl)-acetamide

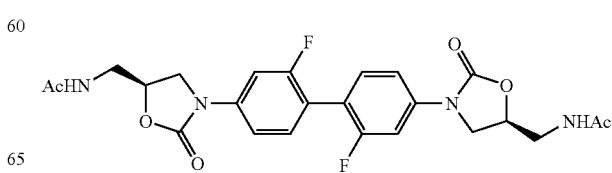

EXAMPLE 2

Acetic acid (5R,5R')-3-[4'-(5-acetoxymethyl-2-oxo-oxazolidin-3-yl)-2,2'-difluoro-biphenyl-4-yl]-2-oxo-oxazolidin-5-ylmethyl ester

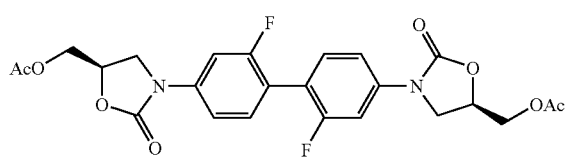

Furthermore, some compounds of the invention may have other chiral centres. It is to be understood that the invention encompasses all such optical and diastereoisomers, and racemic mixtures, that possess antibacterial activity. It is well known in the art how to prepare optically-active forms (for example by resolution of the racemic form by recrystallisation techniques, by chiral synthesis, by enzymatic resolution, by biotransformation or by chromatographic separation) and how to determine antibacterial activity as described hereinafter.

The invention relates to all tautomeric forms of the compounds of the invention that possess antibacterial activity.

It is also to be understood that certain compounds of the invention can exist in solvated as well as unsolvated forms such as, for example, hydrated forms. It is to be understood that the invention encompasses all such solvated forms which possess antibacterial activity.

It is also to be understood that certain compounds of the invention may exhibit polymorphism, and that the invention encompasses all such forms which possess antibacterial activity.

As stated before, we have discovered a range of compounds that have good activity against a broad range of Gram-positive pathogens including organisms known to be resistant to most commonly used antibiotics, together with activity against fastidious Gram negative pathogens such as *H. influenzae, M. catarrhailis, Mycoplasma* and *Chlamydia* strains. The following compounds possess preferred pharmaceutical and/or physical and/or pharmacokinetic properties.

Compounds of the formula (I), or a pharmaceutically-acceptable salt or an in-vivo hydrolysable ester thereof, wherein C is selected from any one of groups D to L represent separate and independent aspects of the invention.

Particularly preferred compounds of the invention comprise a compound of the invention, or a pharmaceutically-acceptable salt or an in-vivo hydrolysable ester thereof, wherein the substituents A, B, $R_1a$, $R_1b$, $R_2a$, $R_2b$, $R_3a$ and $R_3b$ and other substituents mentioned above have values disclosed hereinbefore, or any of the following values (which may be used where appropriate with any of the definitions and embodiments disclosed hereinbefore or hereinafter):

In one embodiment are provided compounds as defined herein in formula (I), in which group C is group D (two phenyl rings).

In another embodiment are provided compounds as defined herein in formula (I), in which group C is group E and $R_2a$ is hydrogen.

In another embodiment are provided compounds as defined herein in formula (I), in which group C is group H and $R_2a$ and $R_2b$ are hydrogen.

In another embodiment are provided compounds of formula (I) in which the group C is a group selected from D, E, F, G, H, I and J as herein defined.

In another embodiment are provided compounds of formula (I) in which the group C is a group selected from D, E, F, G, H, K and L as herein defined.

In another embodiment are provided compounds of formula (I) in which the group C is a group selected from D, E, F, G and H as herein defined.

In a further embodiment are provided compounds of formula (I) in which the group C is a group selected from D, E, G and I as herein defined.

In a further embodiment are provided compounds of formula (I) in which the group C is a group selected from D, E, J and I as herein defined. Preferably C is D or E.

In one embodiment, preferably both A and B are oxazolidinone rings.

In another embodiment, preferably either A or B is an oxazolidinone ring and the other is an isoxazoline ring.

In another embodiment, preferably both A and B are isoxazoline rings.

Preferably $R_2a$ and $R_2b$ are hydrogen and one of $R_3a$ or $R_3b$ is hydrogen and the other is fluorine. More preferably $R_2a$ and $R_2b$ are hydrogen and both $R_3a$ and $R_3b$ are fluorine.

In another embodiment $R_2a$ and $R_3a$ are both fluorine, $R_2b$ and $R_3b$ are both hydrogen.

In a further embodiment $R_2a$, $R_2b$, $R_3a$ and $R_3b$ are selected so as to provide compounds with three fluorine atoms present on the central phenyl rings.

In one embodiment, when C is E, F, G, H, I, J or L, $R_2a$, $R_2b$, $R_3a$ and $R_3b$ are all hydrogen.

In one aspect, when group C is group I or group J and both A and B are oxazolidinones then the oxazolidinone linked to the phenyl group in C is not substituted by methyl acetamide. In a further aspect, when group C is group I or group J and both A and B are oxazolidinones and the oxazolidinone (B or A) linked to the phenyl group in C is substituted by an acetamidomethyl group ($R_1b\text{-}CH_2$ or $R_1a\text{-}CH_2$ respectively) then the oxazolidinone (A or B) that is linked to the pyridyl group in C bears a substitutuent ($R_1a\text{-}CH_2$ or $R_1b\text{-}CH_2$ respectively) that is selected from

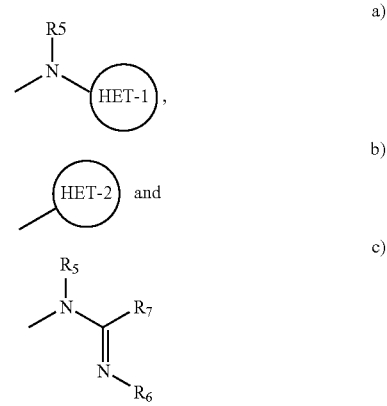

as hereinbefore defined.

In one embodiment, $R_1a$ and $R_1b$ are independently selected from hydroxy, —NHC(=W)$R_4$, —OC(=O)$R_4$, and

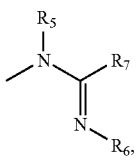

wherein W, R₅ and R₆ are as defined hereinbefore, R₄ is selected from hydrogen, amino, (1-4C)alkyl, —NH(1-4C)alkyl, —N(di-(1-4C)alkyl), —O(1-4C)alkyl, —S(1-4C)alkyl, (2-4C)alkenyl, —(CH₂)$_p$(3-6C)cycloalkyl and —(CH₂)$_p$(3-6C)cycloalkenyl wherein p is 0, 1 or 2; and R₇ is selected from hydrogen, (1-8C)alkyl, —OR₁₂, —SR₁₂, amino, NHR₁₂, N(R₁₂)(R₁₃), (1-8C)alkylaryl and mono-, di-, tri- and per-halo(1-8C)alkyl.

In another embodiment, R₁a and R₁b are independently selected from hydroxy, —NHC(=W)R₄, —OC(=O)R₄, and

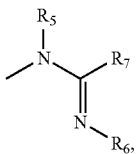

wherein W, R₄, R₅, R₆ and R₇ are as defined hereinbefore, especially wherein R₄ is (1-4C)alkyl, (1-4C)alkoxy, cycloalkyl (particularly cyclopropyl) or haloalkyl (particularly dichloromethyl).

In another embodiment, R₁a and R₁b are independently selected from hydroxy, —NHC(=W)R₄, —OC(=O)R₄, and

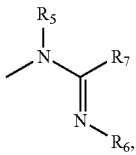

wherein W, R₄, R₅, R₆ and R₇ are as defined hereinbefore, especially wherein R₄ is (1-4C)alkyl or (1-4C)alkoxy.

Particular values for R₅ (which may be used as appropriate with any of the definitions and embodiments disclosed hereinbefore or hereinafter) are hydrogen, tert-butoxycarbonyl and benzyloxycarbonyl. More particularly, R₅ is hydrogen.

In one aspect R₁₂ and R₁₃ are independently selected from hydrogen, alkyl and aryl, or for any N(R₁₂)(R₁₃) group, R₁₂ and R₁₃ may additionally be taken together with the nitrogen atom to which they are attached to form an unsubsituted or substituted pyrrolidinyl, piperidinyl or morpholinyl group; and R₁₄ and R₁₅ are independently selected from hydrogen, phenyl and (1-4C)alkyl.

Preferably R₁a and R₁b are independently selected from hydroxy, —NHCO(1-4C)alkyl, —NHCS(1-4C)alkyl, —NHCOO(1-4C)alkyl, —OCO(1-4C)alkyl, —HN-HET-1 and HET-2.

More preferably R₁a and R₁b are independently selected from —NHCO(1-4C)alkyl, —NHCS(1-4C)alkyl, —HN-HET-1 and HET-2.

In one embodiment R₁a and R₁b are independently selected from hydroxy, —NHCOMe and —NHCOOMe.

In a further embodiment R₁a is selected from hydroxy, —NHCO(1-4C)alkyl (especially —NHCOMe), —NHCS(1-4C)alkyl (especially —NHCSMe), —NHCOO(1-4C)alkyl (especially —NHCO)Me) and —OCO(1-4C)alkyl (especially —OCOMe) and R₁b is HET-2.

In a further embodiment R₁a is selected from hydroxy, —NHCO(1-4C)alkyl (especially —NHCOMe), —NHCS(1-4C)alkyl (especially —NHCSMe), —NHCOO(1-4C)alkyl (especially —NHCO)Me) and —OCO(1-4C)alkyl (especially—OCOMe) and R₁b is —HN-HET-1.

In another embodiment R₁a and R₁b are both —NHCO(1-4C)alkyl (especially —NHCOMe) or HET-2 (especially 1,2,3-triazol-1-yl or tetrazol-2-yl).

In a further embodiment R₁a is —NHCO(1-4C)alkyl (especially —NHCOMe) and R₁b is HET-2 (especially 1,2,3-triazol-1-yl or tetrazol-2-yl).

In a further embodiment, R₁a and R₁b are independently selected from hydroxy, acetamido, 1,2,3-triazol-1-yl, methyl-1,2,3-triazol-1-yl and isoxazolylamino.

In one embodiment HET-1 and HET-2 are unsubsituted. When substituted, preferred substituents are selected from (1-4C)alkyl, especially methyl, and trifluoromethyl.

Preferred are HET-1 and HET-2 as 5-membered rings, in particular HET-1 as isoxazolyl, 1,2,5-thiadiazolyl or isothiazolyl and HET-2 as 1,2,3-triazol-1-yl or tetrazol-2-yl.

In one aspect, HET-2 as 1,2,3-triazol-1-yl is substituted, preferably by methyl or trifluoromethyl.

A preferred class of compounds is of the formula (I) with two central phenyl rings wherein A and B are both oxazolidinone rings;
R₂a and R₂b are both hydrogen; either R₃a and R₃b are both hydrogen or both are fluorine;
R₁a and R₁b are independently selected from hydroxy, —NHCOMe and —NHCOOMe.

Another preferred class of compounds is of the formula (I) with two central phenyl rings wherein A and B are both oxazolidinone rings;
R₂a and R₂b are both hydrogen; either R₃a and R₃b are both hydrogen or both are fluorine;
R₁a is hydroxy and R₁b is HET-2, particularly 1,2,3-triazol-1-yl (optionally substituted).

Another preferred class of compounds is of the formula (I) with two central phenyl rings wherein A and B are both oxazolidinone rings;
R₂a and R₂b are both hydrogen; either R₃a and R₃b are both hydrogen or both are fluorine;
R₁a is acetamido and R₁b is HET-2, particularly 1,2,3-triazol-1-yl (optionally substituted).

Another preferred class of compounds is of the formula (I) with two central phenyl rings wherein A and B are both oxazolidinone rings;
R₂a and R₂b are both hydrogen; either R₃a and R₃b are both hydrogen or both are fluorine;
R₁a and R₁b are independently selected from —NH-HET-1 and HET-2, in particular HET-1 as isoxazolyl, 1,2,5-thiadiazolyl or isothiazolyl and HET-2 as 1,2,3-triazol-1-yl (optionally substituted) or tetrazol-2-yl.

Another preferred class of compounds is of the formula (I) wherein one of A and B is an oxazolidinone ring and the other is an isoxazoline ring;
R₂a and R₂b are both hydrogen; either R₃a and R₃b are both hydrogen or one is fluorine;
R₁a and R₁b are independently selected from hydroxy, —NHCOMe, —NHCOOMe, —NH-HET-1 and HET-2, in particular HET-1 as isoxazolyl, 1,2,5-thiadiazolyl or isothiazolyl and HET-2 as 1,2,3-triazol-1-yl (optionally substituted) or tetrazol-2-yl.

Another preferred class of compounds is of the formula (I) wherein one of A and B is an oxazolidinone ring and the other is an isoxazoline ring;

$R_2a$ and $R_2b$ are both hydrogen; either $R_3a$ and $R_3b$ are both hydrogen or fluorine;

$R_1a$ and $R_1b$ are independently selected from hydroxy, —NHCOMe, —NHCOOMe, —NH-HET-1 and HET-2, in particular HET-1 as isoxazolyl, 1,2,5-thiadiazolyl or isothiazolyl and HET-2 as 1,2,3-triazol-1-yl (optionally substituted) or tetrazol-2-yl.

Another preferred class of compounds is of the formula (I) with two central phenyl rings wherein A and B are both oxazolidinone rings;

one of $R_2a$, $R_2b$, $R_3a$ and $R_3b$ is fluorine and the others are hydrogen;

$R_1a$ and $R_1b$ are independently selected from hydroxy, —NHCOMe and —NHCOOMe.

Another preferred class of compounds is of the formula (I) with two central phenyl rings wherein A and B are both oxazolidinone rings;

one of $R_2a$, $R_2b$, $R_3a$ and $R_3b$ is fluorine and the others are hydrogen;

$R_1a$ is hydroxy and $R_1b$ is HET-2, particularly 1,2,3-triazol-1-yl (optionally substituted).

Another preferred class of compounds is of the formula (I) with two central phenyl rings wherein A and B are both oxazolidinone rings;

one of $R_2a$, $R_2b$, $R_3a$ and $R_3b$ is fluorine and the others are hydrogen;

$R_1a$ is acetamido and $R_1b$ is HET-2, particularly 1,2,3-triazol-1-yl (optionally substituted).

Another preferred class of compounds is of the formula (I) with two central phenyl rings wherein A and B are both oxazolidinone rings;

one of $R_2a$, $R_2b$, $R_3a$ and $R_3b$ is fluorine and the others are hydrogen;

$R_1a$ and $R_1b$ are independently selected from —NH-HET-1 and HET-2, in particular HET-1 as isoxazolyl, 1,2,5-thiadiazolyl or isothiazolyl and HET-2 as 1,2,3-triazol-1-yl (optionally substituted) or tetrazol-2-yl.

Another preferred class of compounds is of the formula (I) wherein one of A and B is an oxazolidinone ring and the other is an isoxazoline ring; one of $R_2a$, $R_2b$, $R_3a$ and $R_3b$ is fluorine and the others are hydrogen;

$R_1a$ and $R_1b$ are independently selected from hydroxy, —NHCOMe, —NHCOOMe, —NH-HET-1 and HET-2, in particular HET-1 as isoxazolyl, 1,2,5-thiadiazolyl or isothiazolyl and HET-2 as 1,2,3-triazol-1-yl (optionally substituted) or tetrazol-2-yl.

Particular compounds of the present invention include each individual compound described in the Examples, especially (5S,5S')-N-(3-{4'-[5-(acetylamino-methyl)-2-oxo-oxazolidin-3-yl]-2,2'-difluoro-biphenyl-4-yl}-2-oxo-oxazolidin-5-ylmethyl)-acetamide;

N-[((5S,5'RS)-3-{4'-[5-(hydroxymethyl)-4,5-dihydroisoxazol-3-yl]-1,1'-biphenyl-4-yl}-2-oxo-1,3-oxazolidin-5-yl)methyl]acetamide;

(5R,5RS')-3-{2-Fluoro-4'-[5-(hydroxymethyl)-4,5-dihydroisoxazol-3-yl]-1,1'biphenyl-4-yl}-5-(1H-1,2,3-triazol-1-ylmethyl)-1,3-oxazolidin-2-one;

N-[((5S)-3-{4'-[(5R)-5-(Hydroxymethyl)4,5-dihydroisoxazol-3-yl]-1,1'-biphenyl-4-yl}-2-oxo-1,3-oxazolidin-5-yl)methyl]acetamide;

N-[((5S)-3-{4'-[(5S)-5-(Hydroxymethyl)4,5-dihydroisoxazol-3-yl]-1,1'-biphenyl-4-yl}-2-oxo-1,3-oxazolidin-5-yl)methyl]acetamide; and (5R)-3-(3-Fluoro-4-{5-[5-(hydroxymethyl)-4,5-dihydroisoxazol-3-yl]thien-2-yl}phenyl)-5-(1H-1,2,3-triazol-1-ylmethyl)-1,3-oxazolidin-2-one.

Process Section:

In a further aspect the present invention provides a process for preparing a compound of invention or a pharmaceutically-acceptable salt or an in-vivo hydrolysable ester thereof. It will be appreciated that during certain of the following processes certain substituents may require protection to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Thus, if reactants include, for example, groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The protecting groups may be removed at any convenient stage in the synthesis using conventional techniques well known in the chemical art.

A compound of the invention, or a pharmaceutically-acceptable salt or an in vivo hydrolysable ester thereof, may be prepared by any process known to be applicable to the preparation of chemically-related compounds. Such processes, when used to prepare a compound of the invention, or a pharmaceutically-acceptable salt or an in vivo hydrolysable ester thereof, are provided as a further feature of the invention and are illustrated by the following representative examples. Necessary starting materials may be obtained by standard procedures of organic chemistry (see, for example, Advanced Organic Chemistry (Wiley-Interscience), Jerry March). The preparation of such starting materials is described within the accompanying non-limiting Examples. Alternatively, necessary starting materials are obtainable by analogous procedures to those illustrated which are within the ordinary skill of an organic chemist. Information on the preparation of necessary starting materials or related compounds (which may be adapted to form necessary starting materials) may also be found in the certain Patent Application Publications, the contents of the relevant process sections of which are hereby incorporated herein by reference; for example WO 94-13649; WO 98-54161; WO 99-64416; WO 99-64417; WO 00-21960; WO 01-40222.

The skilled organic chemist will be able to use and adapt the information contained and referenced within the above references, and accompanying Examples therein and also the Examples herein, to obtain necessary starting materials, and products. For example, the skilled chemist will be able to apply the teaching herein for compounds of formula (I) in which two central phenyl groups are present (that is when group C is group D) to prepare compounds in which group C is any of groups E to L as hereinbefore defined. Similarly, in the processes illustrated below the skilled chemist will be able to apply the teaching as necessary to prepare compounds in which both rings A and B are isoxazoline and those compounds in which one of rings A and B is isoxazoline and the other oxazolidinone.

Thus, the present invention also provides that the compounds of the invention and pharmaceutically-acceptable salts and in vivo hydrolysable esters thereof, can be prepared by a process (a) to (d) as follows (wherein the variables are as defined above unless otherwise stated):

a) by modifying a substituent in, or introducing a substituent into another compound of the invention by using standard chemistry (see for example, Comprehensive Organic Functional Group Transformations (Pergamon), Katritzky, Meth-Cohn & Rees); for example:

a hydroxy group may be converted into a silyloxy group; an acylamino or thioacylamino group, for instance an acetamide group (optionally substituted or protected on the amido-nitrogen atom); into an acyloxy group, for instance an acetoxy group; a heterocyclylamino group (optionally substituted or protected on the amino-nitrogen atom), for instance an isoxazol-3-ylamino group or a 1,2,5-thiadiazol-3-ylamino group; a heterocyclyl group linked through nitrogen (optionally substituted on a carbon other than a carbon atom adjacent to the linking nitrogen ring atom), for instance an optionally 4-substituted 1,2,3-triazol-1-yl group; or an amidino group, for instance an 1-(N-cyanoimino)ethylamino group; such conversions of the hydroxy group taking place directly (for instance by acylation or Mitsunobu reaction) or through the intermediacy of one or more derivatives (for instance a mesylate or an azide);

an acyloxy group may be converted into a hydroxy group or into the groups that may be obtained from a hydroxy group (either directly or through the intermediacy of a hydroxy group);

a silyloxy group may be converted into a hydroxy group or into the groups that may be obtained from a hydroxy group (either directly or through the intermediacy of a hydroxy group);

an acylamino group or thioacylamino group may be converted into another acylamino group or thioacylamino group; into a heterocyclylamino group (optionally substituted or protected on the amino-nitrogen atom); a heterocyclyl group linked through nitrogen (optionally substituted on a carbon other than a carbon adjacent to the linking nitrogen atom), for instance an optionally 4-substituted 1,2,3-triazol-1-yl group; or an amidino group; such conversions of the acylamino group taking place either directly or through through the intermediacy of one or more derivatives such as an amino group;

a heterocyclylamino group (optionally substituted or protected on the amino-nitrogen atom) may be converted into another heterocyclyl amino group (optionally substituted or protected on the amino-nitrogen atom) by refunctionalisation, for instance by protection or deprotection, of the amino-nitrogen atom, by introduction of a new ring substituent, or by refunctionalisation of an existing ring substituent; or a heterocyclyl group linked through nitrogen (optionally substituted on a carbon other than a carbon atom adjacent to the linking nitrogen ring atom) may be converted into another heterocyclyl group linked through nitrogen (optionally substituted on a carbon other than a carbon atom adjacent to the linking nitrogen ring atom) by introduction of a new ring substituent or by refunctionalisation of an existing ring substituent, for instance by modifying the 4-substituent of a 4-substituted 1,2,3-triazol-1-yl group. For instance, examples drawn from the methods for conversion of a hydroxy group into an optionally substituted triazole group are illustrated by the scheme:

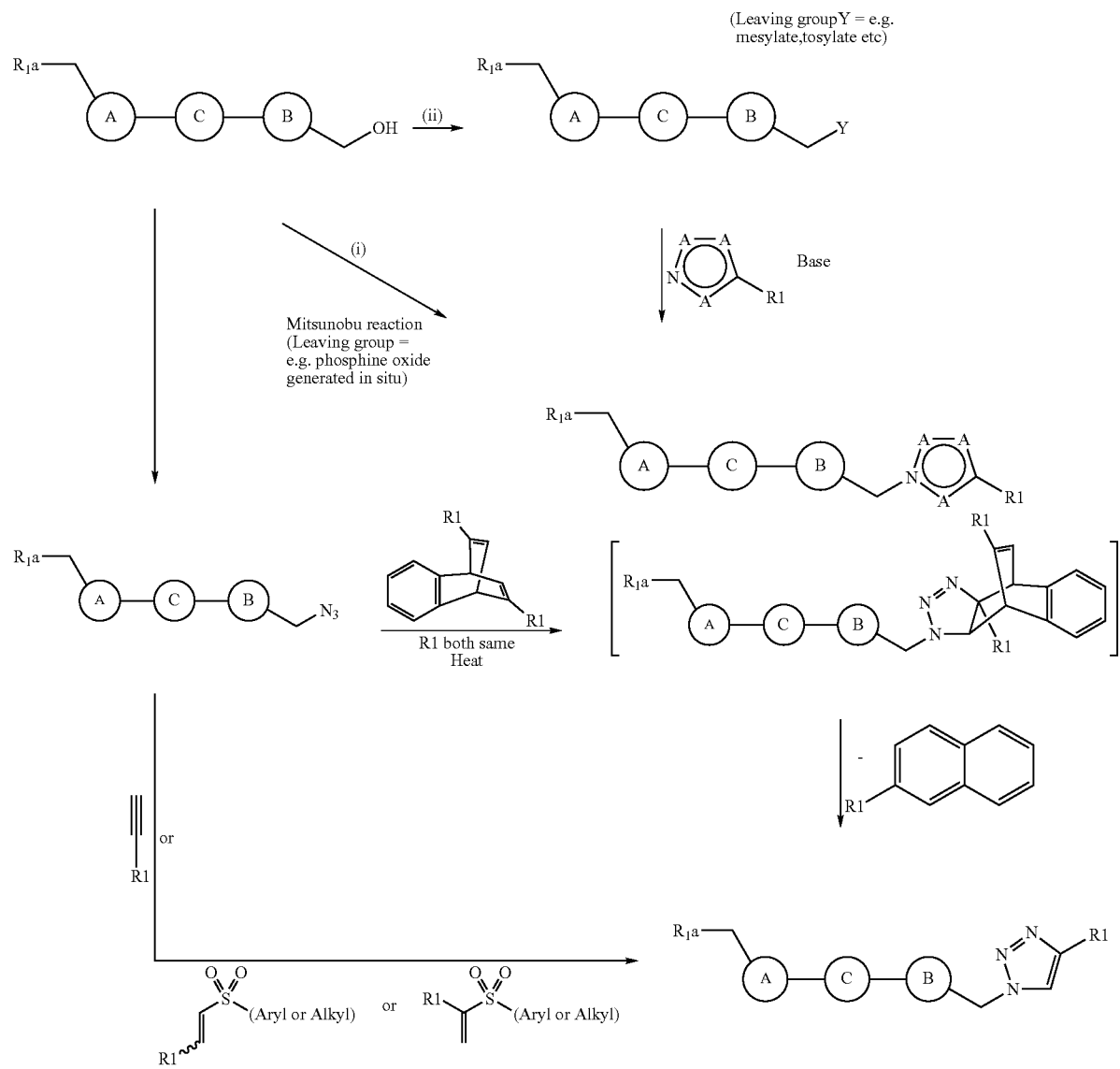

and an example drawn from the range of regioselective methods that proceed under very mild conditions is illustrated by the following scheme showing the Cu(I)-catalysed cycloaddition in aqueous alcoholic solution at ambient temperatures of azides and terminal alkynes to give 4-substituted 1,2,3-triazoles (V. V. Rostovtsev, L. G. Green, V. V. Fokin, and K. B. Sharpless, Angew. Chem. Int. Ed., 2002, 41, 2596-2599):

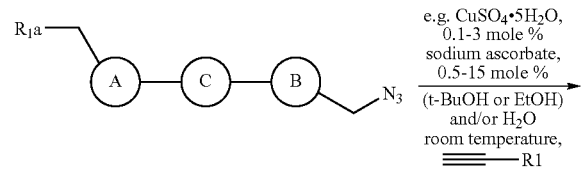

-continued

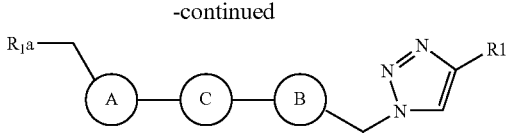

b) by reaction of two molecules of a compound of formula (II) (wherein X is a leaving group useful in palladium coupling, for example boronate, trimethyl tin, iodo and bromo) such that an aryl-aryl, heteroaryl-aryl, or heteroaryl-heteroaryl bond replaces the two aryl-X or heteroaryl-X bonds. Such methods are now well known, see for instance S. P. Stanforth, Catalytic Cross-Coupling Reactions in Biaryl Synthesis, *Tetrahedron*, 54 1998, 263-303.

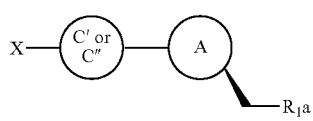

(II)

The leaving group X may be the same or different in the two molecules of formula (II).

For example

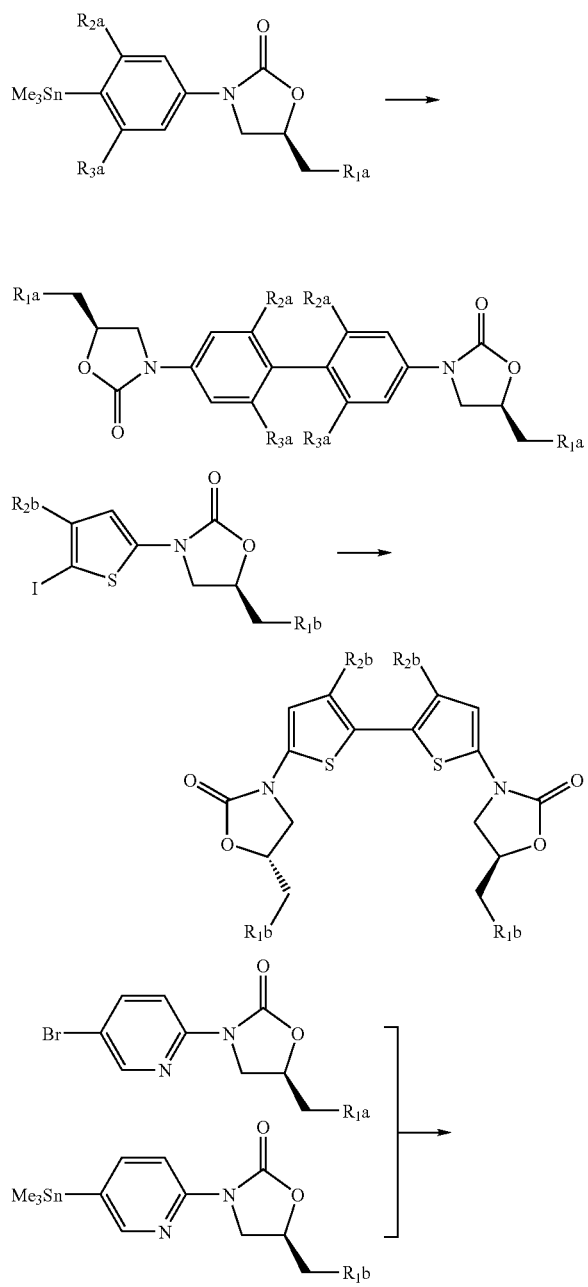

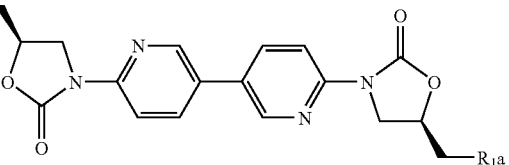

Similarly, this chemistry may be applied to two dissimilar molecules of formula (II), for example those in which ring A is not the same as ring B, wherein X is suitably selected to enable unsymmetrical coupling so that an aryl-aryl, heteroaryl-aryl, or heteroaryl-heteroaryl bond replaces two different aryl-X or heteroaryl-X bonds.

For example

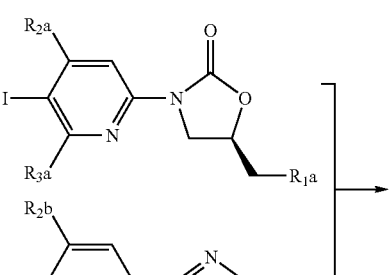

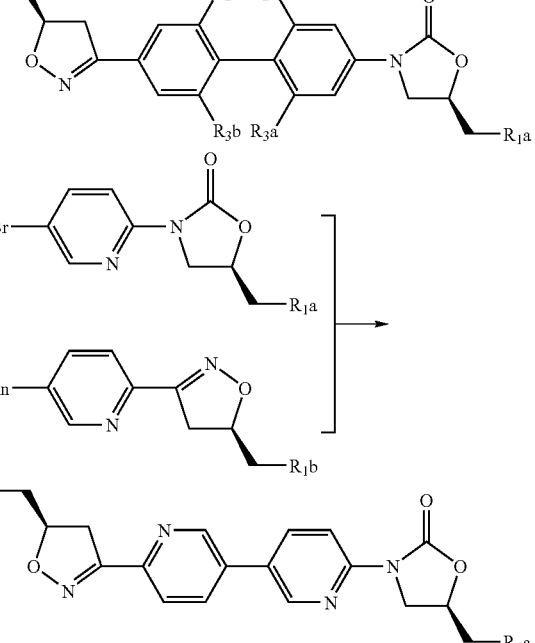

Furthermore, this chemistry may also be applied to two dissimilar molecules of formula (II), for example those in which ring C' is not the same as ring C", wherein X is suitably selected to enable unsymmetrical coupling so that an aryl-aryl, heteroaryl-aryl, or heteroaryl-heteroaryl bond replaces two different aryl-X or heteroaryl-X bonds.

For example

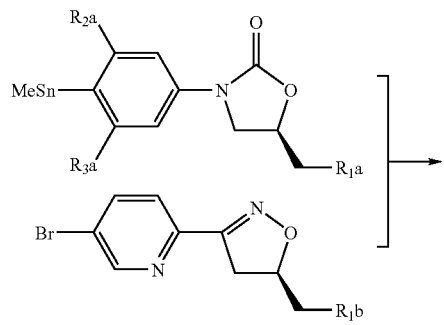

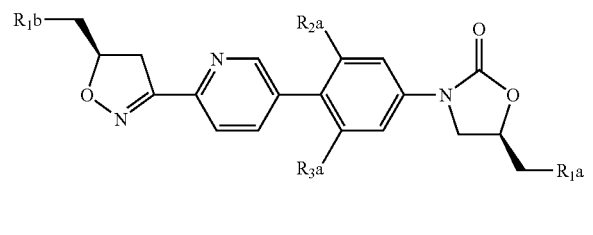

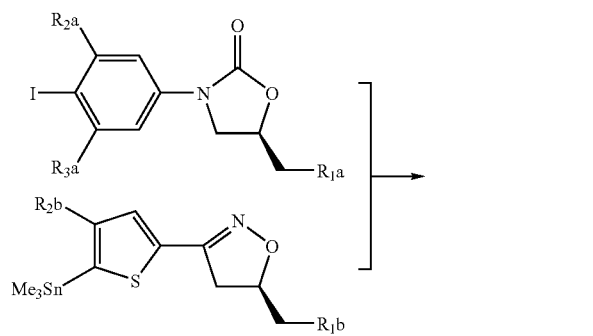

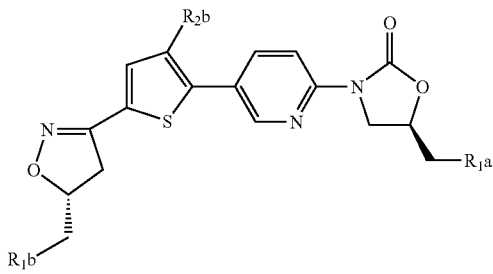

c) by reaction of a (hetero)biaryl derivative (III) carbamate with an appropriately substituted oxirane to form an oxazolidinone ring at the undeveloped aryl position.

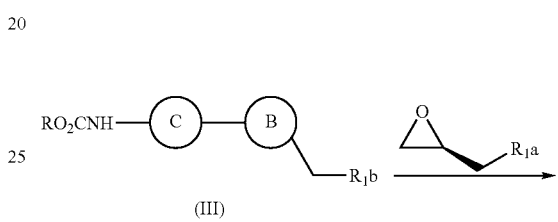

Variations on this process in which the carbamate is replaced by an isocyanate or by an amine or/and in which the oxirane is replaced by an equivalent reagent X—CH$_2$CH(O-optionally protected)CH$_2$R$_1$a where X is a displaceable group are also well known in the art.

For example,

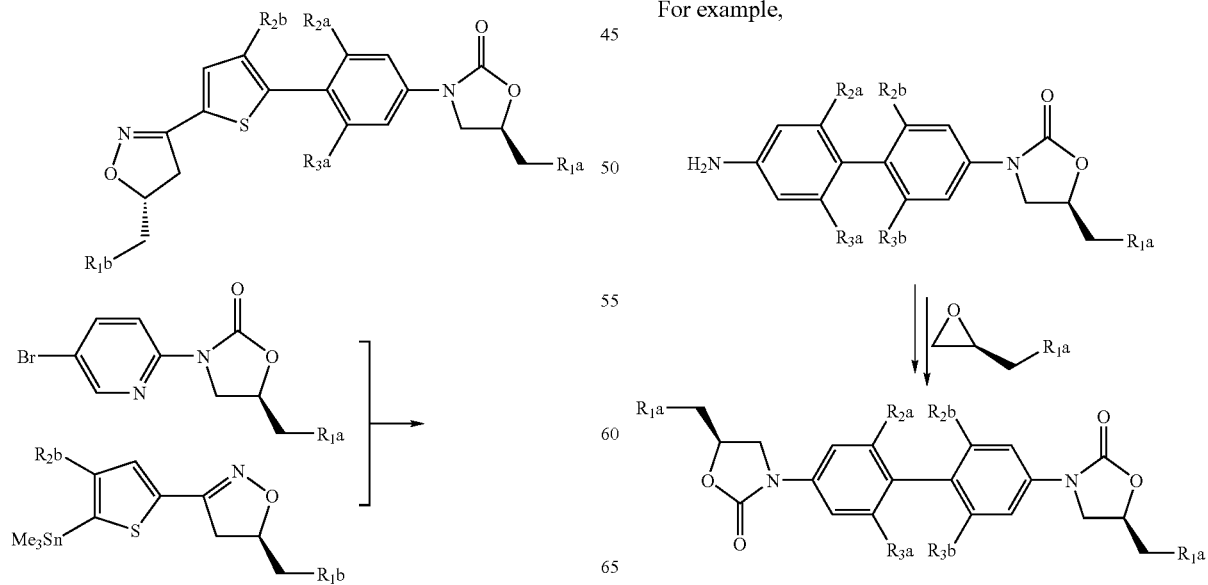

d) by reaction of a (hetero)biaryl derivative (IV) to form an isoxazoline ring at the undeveloped aryl position.

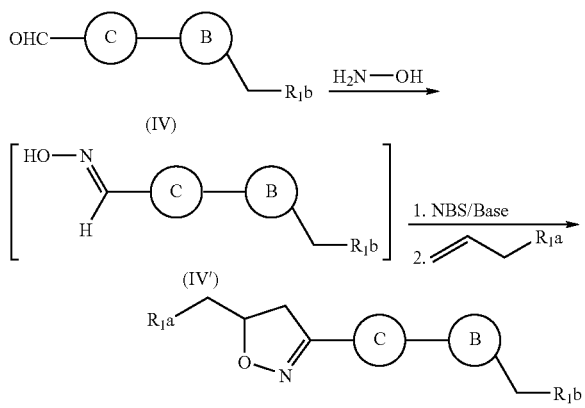

Variations on this process in which the reactive intermediate (a nitrile oxide IV''') is obtained other than by oxidation of an oxime (IV') are well known in the art.

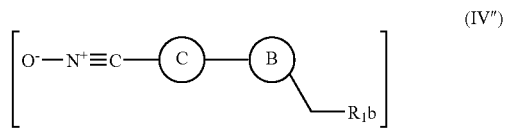

For example, oxidation of an appropriately substituted biphenylcarboxaldehyde oxime in the presence of an appropriately substituted allyl derivative gives an isoxazoline of the required structure.

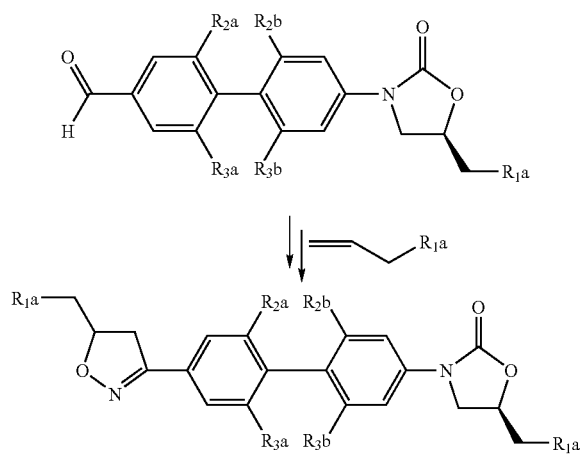

The removal of any protecting groups, the formation of a pharmaceutically-acceptable salt and/or the formation of an in vivo hydrolysable ester are within the skill of an ordinary organic chemist using standard techniques. Furthermore, details on the these steps, for example the preparation of in-vivo hydrolysable ester prodrugs has been provided, for example, in the section above on such esters.

When an optically active form of a compound of the invention is required, it may be obtained by carrying out one of the above procedures using an optically active starting material (formed, for example, by asymmetric induction of a suitable reaction step), or by resolution of a racemic form of the compound or intermediate using a standard procedure, or by chromatographic separation of diastereoisomers (when produced). Enzymatic techniques may also be useful for the preparation of optically active compounds and/or intermediates.

Similarly, when a pure regioisomer of a compound of the invention is required, it may be obtained by carrying out one of the above procedures using a pure regioisomer as a starting material, or by resolution of a mixture of the regioisomers or intermediates using a standard procedure.

According to a further feature of the invention there is provided a compound of the invention, or a pharmaceutically-acceptable salt, or in-vivo hydrolysable ester thereof for use in a method of treatment of the human or animal body by therapy.

According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt, or in-vivo hydrolysable ester thereof.

The invention also provides a compound of the invention, or a pharmaceutically-acceptable salt, or in-vivo hydrolysable ester thereof, for use as a medicament; and the use of a compound of the invention of the present invention, or a pharmaceutically-acceptable salt, or in-vivo hydrolysable ester thereof, in the manufacture of a medicament for use in the production of an antibacterial effect in a warm blooded animal, such as man.

In order to use a compound of the invention, an in-vivo hydrolysable ester or a pharmaceutically-acceptable salt thereof, including a pharmaceutically-acceptable salt of an in-vivo hydrolysable ester, (hereinafter in this section relating to pharmaceutical composition "a compound of this invention") for the therapeutic (including prophylactic) treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the invention, an in-vivo hydrolysable ester or a pharmaceutically-acceptable salt thereof, including a pharmaceutically-acceptable salt of an in-vivo hydrolysable ester, and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, aerosols (or sprays), drops and sterile injectable aqueous or oily solutions or suspensions.

In addition to the compounds of the present invention the pharmaceutical composition of this invention may also contain or be co-administered (simultaneously, sequentially or separately) with one or more known drugs selected from other clinically useful antibacterial agents (for example, β-lactams or aminoglycosides) and/or other anti-infective agents (for example, an antifungal triazole or amphotericin). These may include carbapenems, for example meropenem or imipenem, to broaden the therapeutic effectiveness. Compounds of this invention may also contain or be co-administered with bactericidal/permeability-increasing protein (BPI) products or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 1 mg and 1 g of a compound of this invention, preferably between 100 mg and 1 g of a compound. Especially preferred is a tablet or capsule which contains between 50 mg and 800 mg of a compound of this invention, particularly in the range 100 mg to 500 mg.

In another aspect a pharmaceutical composition of the invention is one suitable for intravenous, subcutaneous or intramuscular injection, for example an injection which contains between 0.1% w/v and 50% w/v (between 1 mg/ml and 500 mg/ml) of a compound of this invention.

Each patient may receive, for example, a daily intravenous, subcutaneous or intramuscular dose of 0.5 $mgkg^{-1}$ to 20 $mgkg^{-1}$ of a compound of this invention, the composition being administered 1 to 4 times per day. In another embodiment a daily dose of 5 $mgkg^{-1}$ to 20 $mgkg^{-1}$ of a compound of this invention is administered. The intravenous, subcutaneous and intramuscular dose may be given by means of a bolus injection. Alternatively the intravenous dose may be given by continuous infusion over a period of time. Alternatively each patient may receive a daily oral dose which may be approximately equivalent to the daily parenteral dose, the composition being administered 1 to 4 times per day.

A pharmaceutical composition to be dosed intravenously may contain advantageously (for example to enhance stability) a suitable bactericide, antioxidant or reducing agent, or a suitable sequestering agent.

In the above other, pharmaceutical composition, process, method, use and medicament manufacture features, the alternative and preferred embodiments of the compounds of the invention described herein also apply.

Antibacterial Activity:

The pharmaceutically-acceptable compounds of the present invention are useful antibacterial agents having a good spectrum of activity in vitro against standard Gram-positive organisms, which are used to screen for activity against pathogenic bacteria. Notably, the pharmaceutically-acceptable compounds of the present invention show activity against enterococci, pneumococci and methicillin resistant strains of S. aureus and coagulase negative staphylococci, together with haemophilus and moraxella strains. The antibacterial spectrum and potency of a particular compound may be determined in a standard test system.

The (antibacterial) properties of the compounds of the invention may also be demonstrated and assessed in-vivo in conventional tests, for example by oral and/or intravenous dosing of a compound to a warm-blooded mammal using standard techniques.

The following results were obtained on a standard in-vitro test system. The activity is described in terms of the minimum inhibitory concentration (MIC) determined by the agar-dilution technique with an inoculum size of $10^4$ CFU/spot. Typically, compounds are active in the range 0.01 to 256 μg/ml.

Staphylococci were tested on agar, using an inoculum of $10^4$ CFU/spot and an incubation temperature of 37° C. for 24 hours—standard test conditions for the expression of methicillin resistance.

Streptococci and enterococci were tested on agar supplemented with 5% defibrinated horse blood, an inoculum of $10^4$ CFU/spot and an incubation temperature of 37° C. in an atmosphere of 5% carbon dioxide for 48 hours—blood is required for the growth of some of the test organisms. Fastidious Gram negative organisms were tested in Mueller-Hinton broth, supplemented with hemin and NAD, grown aerobically for 24 hours at 37° C., and with an innoculum of $5\times10^4$ CFU/well.

For example, the following results were obtained for the compound of Example 1:

| Organism | | MIC (μg/ml) |
|---|---|---|
| Staphylococcus aureus: | MSQS | 0.25 |
| | MRQR | 0.5 |
| Streptococcus pneumoniae | | 0.06 |
| Streptococcus pyogenes | | 0.13 |
| Haemophilus influenzae | | 2.0 |
| Moraxella catarrhalis | | 0.5 |

MSQS = methicillin sensitive and quinolone sensitive
MRQR = methicillin resistant and quinolone resistant Certain intermediates and/or Reference Examples described hereinafter are within the scope of the invention and may also possess useful activity, and are provided as a further feature of the invention.

The invention is now illustrated but not limited by the following Examples in which unless otherwise stated:

(i) evaporations were carried out by rotary evaporation in vacuo and work-up procedures were carried out after removal of residual solids by filtration;

(ii) operations were carried out at ambient temperature, that is typically in the range 18-26° C. and without exclusion of air unless otherwise stated, or unless the skilled person would otherwise work under an inert atmosphere;

(iii) column chromatography (by the flash procedure) was used to purify compounds and was performed on Merck Kieselgel silica (Art. 9385) unless otherwise stated;

(iv) yields are given for illustration only and are not necessarily the maximum attainable;

(v) the structure of the end-products of the invention were generally confirmed by NMR and mass spectral techniques [proton magnetic resonance spectra were generally determined in DMSO-$d_6$ unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δscale) and peak multiplicities are shown thus: s, singlet; d, doublet; AB or dd, doublet of doublets; dt, doublet of triplets; dm, doublet of multiplets; t, triplet, m, multiplet; br, broad; fast-atom bombardment (FAB) mass spectral data were generally obtained using a Platform spectrometer (supplied by Micromass) run in electrospray and, where appropriate, either positive ion data or negative ion data were collected]; optical rotations were determined at 589 nm at 20° C. for 0.1M solutions in methanol using a Perkin Elmer Polarimeter 341;

(vi) each intermediate was purified to the standard required for the subsequent stage and was characterised in sufficient detail to confirm that the assigned structure was correct; purity was assessed by HPLC, TLC, or NMR and identity was determined by infra-red spectroscopy (IR), mass spectroscopy or NMR spectroscopy as appropriate;

(vii) in which the following abbreviations may be used:

DMF is N,N-dimethylformamide; DMA is N,N-dimethylacetamide; TLC is thin layer chromatography; HPLC is high pressure liquid chromatography; MPLC is medium pressure liquid chromatography; DMSO is dimethylsulfoxide; $CDCl_3$ is deuterated chloroform; MS is mass spectroscopy; ESP is electrospray; EI is electron impact; CI is chemical ionisation; APCI is atmospheric pressure chemical ionisation; EtOAc is ethyl acetate; MeOH is methanol; phosphoryl is $(HO)_2$—P(O)—O—; phosphiryl is $(HO)_2$—P—O—; Bleach is "Clorox" 6.15% sodium hypochlorite;

(viii) temperatures are quoted as ° C.

Synthesis of some frequently used intermediates will now be described, followed by the Examples.

[3-(4-Bromo-phenyl)-4,5-dihydro-isoxazol-5-yl]-methanol

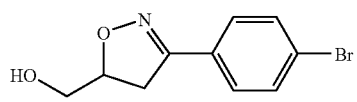

4-Bromo-benzaldehyde oxime (162 g, 789.9 mmol) and allyl alcohol (130.5 ml) were added to tetrahydrofuran (1000 ml) and then bleach (5305 ml) was added. The reaction was cooled to 0° C. and stirred for 3 hrs. The precipitate was collected and washed with water (2×300 ml) to give the desired product (137 g).

NMR (DMSO-$d_6$) δ: 3.12 (dd, 1H); 3.32 (dd, 1H); 3.49 (m, 2H); 4.64 (m, 1H); 4.92 (t, 1H); 7.57 (d, 2H); 7.62 (d, 2H).

Methansulfonic acid 3-(4-bromo-phenyl)-4,5-dihydro-isoxazol-5-ylmethyl ester

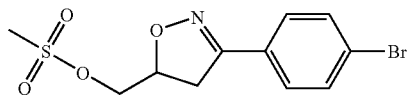

[3-(4-Bromo-phenyl)-4,5-dihydro-isoxazol-5-yl]-methanol (84.3 g, 328 mmol) was added to anhydrous dichloromethane (500 ml) followed by addition of triethylamine (64.1 ml, 459.2 mmol). The solution was allowed to cool to 0° C. followed by dropwise addition of methane sulfonyl chloride (30.65 ml, 396 mmol). The reaction was stirred for 2 hours at 0° C. and then aqueous sodium bicarbonate (200 ml) was added. After further extraction with dichloromethane (2×200 ml), the organic layers were combined, dried over sodium sulfate, and concentrated in vacuo to give the desired product (110 g).

NMR (DMSO-$d_6$) δ: 3.08 (s, 3H); 3.27 (dd, 1H); 3.47 (dd, 1H); 4.37 (m, 2H); 5.02 (m, 1H); 7.53 (m, 4H).

5-Azidomethyl-3-(4-bromo-phenyl)-4,5-dihydro-isoxazole

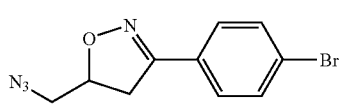

Methanesulfonic acid 3-(4-bromo-phenyl)-4,5-dihydro-isoxazol-5-ylmethyl ester (55 g, 164.2 mmol) was added to dimethyl formamide (200 ml) followed by addition of sodium azide (21.4 g, 328.4 mmol). The mixture was heated to 75° C. for six hours and then added to aqueous sodium chloride (300 ml) followed by extraction with gethyl acetate (3×300 ml). The organic layers were combined, dried over sodium sulfate, and concentrated in vacuo to yield the desired product (52 g).

NMR (DMSO-$d_6$) δ: 3.25 (dd, 1H); 3.53 (dd, 1H); 3.61 (m, 2H); 4.96 (m, 1H); 7.65 (d, 2H); 7.71 (d, 2H).

[3-(4-Bromo-phenyl)-4,5-dihydro-isoxazol-5-yl]-methylamine

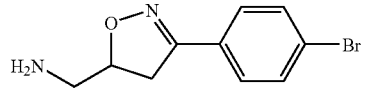

5-Azidomethyl-3-(4-bromo-phenyl)-4,5-dihydro-isoxazole (52 g, 184.4 mmol) was dissolved in dichloromethane:methanol:water 16:5:1 (440 ml) followed by addition of 200 grams of polystyrene-bound triphenylphosphine resin (1.6 mmol per gram). The mixture was stirred for 16 hours and filtered. The resin was washed with dichloromethane (200 ml) and methanol (100 ml) and then the solvents were concentrated in vacuo to give the desired product (47 g).

NMR (DMSO-$d_6$) δ: 3.75 (m, 2H); 3.25 (dd, 1H); 3.44 (dd, 1H); 4.69 (m, 1H); 7.62 (d, 2H); 7.68 (d, 2H).

N-[3-(4-Bromo-phenyl)-4,5-dihydro-isoxazol-5-ylmethyl]-acetamide

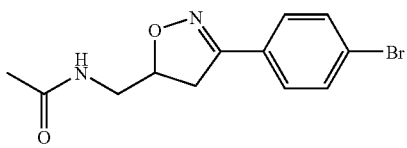

[3-(4-Bromo-phenyl)-4,5-dihydro-isoxazol-5-yl]-methylamine (10 g, 39.1 mmol) and triethylamine (8.2 ml, 58.6 mmol) were added to anhydrous dichloromethane (100 ml) and cooled to 0° C. Acetyl chloride (3.0 ml, 43.6 mmol) was then added dropwise and the reaction was stirred for 3 hours followed by addition of ethyl acetate (200 ml). The precipitate was collected, washed with water (2×100 ml), and finally with ethyl ether (2×50 ml) to give the desired product (6.9 g).

NMR (DMSO-$d_6$): δ: 1.84 (s, 3H); 3.13 (dd, 1H); 3.28 (m, 2H); 3.47 (dd, 1H); 4.76 (m, 1H); 7.6 (d, 2H); 7.67 (d, 2H); 8.16 (t, 1H).

1-[3-(4-Bromo-phenyl)-4,5-dihydro-isoxazol-5-ylmethyl]-1H-[1,2,3]triazole

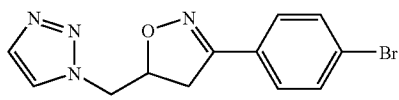

5-Azidomethyl-3-(4-bromo-phenyl)-4,5-dihydro-isoxazol (12.3 g, 43.6 mmol) and bicyclo[2.2.1]hepta-2,5-diene (23.6 ml, 218.1 mmol) were added to dioxane (200 ml), heated to 100° C. and stirred for six hours. The reaction mixture was concentrated in vacuo followed by addition of ethyl ether (200 ml). The precipitate was collected and washed with ethyl ether (3×20 ml) and dried under nitrogen to give the desired product (8.8 g).

NMR (DMSO-$d_6$) δ: 3.31 (dd, 1H); 3.62 (dd, 1H); 4.68 (m, 2H); 5.19 (m, 1H); 7.59 (d, 2H); 7.69 (d, 2H); 7.76 (d, 1H); 8.17 (d, 1H).

1-[3-(4-Bromo-phenyl)-4,5-dihydro-isoxazol-5-ylmethyl]-4-methyl-1H-[1,2,3]triazole

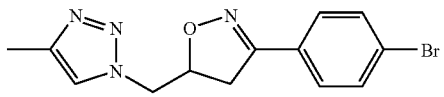

[3-(4-Bromo-phenyl)-4,5-dihydro-isoxazol-5-yl]-methylamine (10 g, 39.1 mmol) and diisopropylethylamine (33.9 ml, 195.3 mmol) were added to anhydrous methanol (100 ml) followed by addition of N'-[2,2-dichloro-1-methylethylidene]-4-methylbenzenesulfonylhydrazide (14.9 g, 50.8 mmol). The reaction mixture was stirred at room temperature for four hours and then ethyl acetate was added. The precipitate was collected and washed with water (2×50 ml) to give the desired product (4.49 g).

NMR (DMSO-$d_6$) δ: 2.23 (s, 3H); 3.28 (dd, 1H); 3.59 (dd, 1H); 4.58 (m, 2H); 5.14 (m, 1H); 7.59 (d, 2H); 7.67 (d, 2H); 7.86 (s, 1H).

[3-(4-Bromo-3-fluoro-phenyl)-4,5-dihydro-isoxazol-5-yl]-methanol

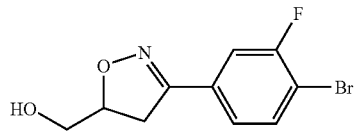

4-Bromo-3-fluoro-benzaldehyde oxime (55.7 g, 265.3 mmol) and allyl alcohol (44 ml) were added to tetrahydrofuran (300 ml) and then bleach (1791 ml) was added. The reaction was stirred for four hours followed by extraction with tetrahydrofuran (2×200 ml). The organic layers were combined, dried over sodium sulfate, and concentrated in vacuo to give the desired product (66 g).

NMR (DMSO-$d_6$) δ: 3.23 (dd, 1H); 3.41 (dd, 1H); 3.55 (m, 2H); 4.77 (m, 1H); 5.05 (d, 1H); 7.47 (d, 1H); 7.6 (d, 1H); 7.81 (t, 1H).

Methanesulfonic acid 3-(4-bromo-3-fluoro-phenyl)4,5-dihydro-isoxazol-5ylmethyl ester

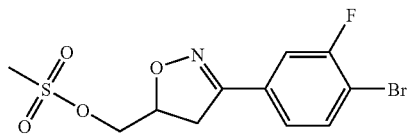

[3-(4-Bromo-3-fluoro-phenyl)-4,5-dihydro-isoxazol-5-yl]-methanol (30 g, 112.4 mmol) was added to anhydrous dichloromethane (300 ml) followed by addition of triethylamine (21.8 ml, 157.3 mmol). The solution was cooled to 0° C. followed by drop wise addition of methane sulfonyl chloride (10.4 ml, 134.8 mmol). The reaction was stirred for 2 hours at 0° C. and then aqueous sodium bicarbonate (100 ml) was added. After further extraction with dichloromethane (2×100 ml), the organic layers were combined, dried over sodium sulfate, and concentrated in vacuo to give the desired product (38.7 g).

NMR (DMSO-$d_6$) δ: 3.15 (s, 3H); 3.18 (dd, 1H); 3.52 (dd, 1H); 4.29 (m, 2H); 4.99 (m, 1H); 7.40 (d, 1H); 7.59 (d, 1H); 7.76 (t, 1H).

5-Azidomethyl-3-(4-bromo-3-fluoro-phenyl)-4,5-dihydro-isoxazole

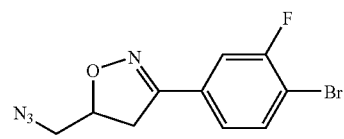

Methanesulfonic acid 3-(4-bromo-3-fluoro-phenyl)-4,5-dihydro-isoxazol-5-ylmethyl ester (38.6 g, 111.9 mmol) was added to dimethyl formamide (100 ml) followed by addition of sodium azide (14.5 g, 223.8 mmol). The mixture was heated to 75° C. for five hours and then added to aqueous sodium chloride (200 ml) followed by extraction with ethyl acetate (3×200 ml). The organic layers were combined, dried over sodium sulfate, and concentrated in vacuo to yield the desired product (31 g).

NMR (DMSO-$d_6$) δ: 3.23 (dd, 1H); 3.52 (dd, 1H); 3.6 (m, 2H); 4.99 (m, 1H); 7.48 (d, 1H); 7.66 (d, 1H); 7.82 (t, 1H).

[3-(4-Bromo-3-fluoro-phenyl)-4,5-dihydro-isoxazol-5-yl]-methylamine

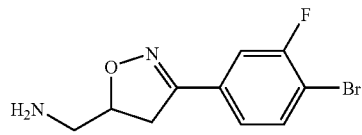

5-Azidomethyl-3-(4-bromo-3-fluoro-phenyl)-4,5-dihydro-isoxazole (31 g, 106.2 mmol) was dissolved in dichloromethane:methanol:water 16:5:1 (215 ml) followed by addition of 100 grams of polystyrene bound triphenylphosphine resin (1.6 mmol per gram). The mixture was stirred for 16 hours and filtered. The resin was washed with dichloromethane (100 ml) and methanol (50 ml) and then the solvents were concentrated in vacuo to give the desired product (27.9 g).

NMR (DMSO-$d_6$) δ: 2.73 (m, 2H); 3.26 (dd, 1H); 3.41 (dd, 1H); 4.74 (m, 1H); 7.47 (d, 1H); 7.63 (d, 1H); 7.82 (t, 1H).

N-[3-(4-Bromo-3-fluoro-phenyl)-4,5-dihydro-isoxazol-5-ylmethyl]-acetamide

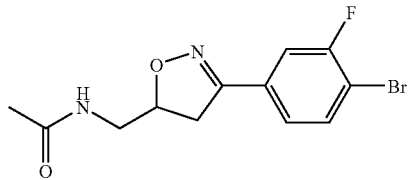

[3-(4-Bromo-3-fluoro-phenyl)-4,5-dihydro-isoxazol-5-yl]-methylamine (9 g, 33.8 mmol) and triethylamine (7 ml, 50.8 mmol) were added to anhydrous dichloromethane (100 ml) and cooled to 0° C. Acetyl chloride (2.8 ml, 40.6 mmol) was then added dropwise and the reaction was stirred for 3 hours followed by addition of ethyl acetate (200 ml). The precipitate was collected and washed with water (2×50 ml) to give the desired product (5 g).

NMR (DMSO-$d_6$) δ: 1.83 (s, 3H); 3.15 (dd, 1H); 3.28 (m, 2H); 3.48 (dd, 1H); 4.81 (m, 1H); 7.45 (d, 1H); 7.62 (d, 1H); 7.82 (t, 1H), 8.16 (m, 1H).

1-[3-(4-Bromo-3-fluoro-phenyl)-4,5-dihydro-isoxazol-5-ylmethyl]-4-methyl-1H-[1,2,3]triazole

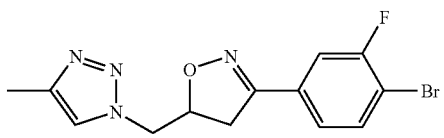

[3-(4-Bromo-3-fluoro-phenyl)-4,5-dihydro-isoxazol-5-yl]-methylamine (9 g, 33.8 mmol) and diisopropylethylamine (21.8 ml, 169.5 mmol) were added to anhydrous methanol (100 ml) followed by addition of N'-[2,2-dichloro-1-methyl-ethylidene]-4-methylbenzenesulfonylhydrazide (12.9 g, 43.9 mmol). The reaction was stirred at room temperature for four hours and then ethyl acetate was added. The precipitate was collected and washed with water (2×50 ml) to give the desired product (3.89 g).

NMR (DMSO-$d_6$) δ: 2.05 (s, 3H); 3.07 (dd, 1H); 3.4 (dd, 1H); 4.38 (m, 2H); 4.97 (m, 1H); 7.25 (d, 1H); 7.44 (d, 1H); 7.62 (t, 1H), 7.67 (s, 1H).

5-Bromo-pyridine-2-carbaldehyde oxime

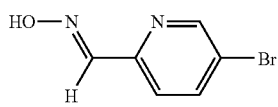

5-Bromo-pyridine-2-carbaldehyde (60 g, 322 mmol) was added to methanol (700 ml) and then water was added (700 ml) followed by addition of hydroxylamine hydrochloride (28 g, 403 mmol). Sodium carbonate (20.5 g, 193.2 mmol) in water (200 ml) was added and the reaction was stirred for 30 minutes. Water (500 ml) was then added and the precipitate was filtered and washed with water (2×300 ml) to give the desired product (60 g).

NMR (DMSO-$d_6$) δ: 7.75 (d, 1H); 8.09 (t, 2H), 8.72 (s, 1H); 11.84 (s, 1H).

[3-(5-Bromo-pyridin-2-yl)-4,5-dihydro-isoxazol-5-yl]-methanol

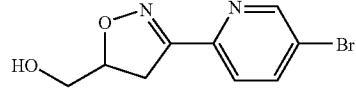

5-Bromo-pyridine-2-carbaldehyde oxime (60 g, 298.5 mmol) and allyl alcohol (49.7 ml) were added to tetrahydrofuran (200 ml) and then bleach (2016 ml) was added. The reaction was stirred for four hours followed by extraction with tetrahydrofuran (2×200 ml). The organic layers were combined, dried over sodium sulfate, and concentrated in vacuo to give the desired product (38.8 g).

NMR (DMSO-$d_6$) δ: 3.2 (dd, 1H); 3.41 (dd, 1H); 3.55 (m, 2H); 4.8 (m, 1H); 5.02 (d, 1H); 7.84 (d, 1H); 8.16 (d, 1H); 8.8 (s, 1H).

Methanesulfonic acid 3-(5-bromo-pyridin-2-yl)-4,5-dihydro-isoxazol-5-ylmethyl ester

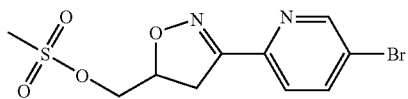

[3-(5-Bromo-pyridin-2-yl)-4,5-dihydro-isoxazol-5-yl]-methanol (38.8 g, 150.5 mmol) was added to anhydrous dichloromethane (200 ml) followed by addition of triethylamine (29.2 ml, 210.7 mmol). The solution was cooled to 0° C. followed by dropwise addition of methane sulfonyl chloride (12.3 ml, 180.6 mmol). The reaction was stirred for 2 hours at 0° C. and then aqueous sodium bicarbonate (100 ml) was added. After further extraction with dichloromethane (2×100 ml), the organic layers were combined, dried over sodium sulfate, and concentrated in vacuo to give the desired product (30.5 g).

NMR (DMSO-$d_6$) δ: 3.24 (dd, 1H); 3.55 (dd, 1H); 3.55 (m, 2H); 5.04 (m, 1H); 7.85 (d, 1H); 8.18 (d, 1H); 8.82 (s, 1H).

5-Azidomethyl-3-(5-bromo-pyridin-2-yl)-4,5-dihydro-isoxazole

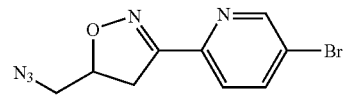

Methanesulfonic acid 3-(5-bromo-pyridin-2-yl)-4,5-dihydro-isoxazol-5-ylmethyl ester (30.5 g, 90.77 mmol) was added to dimethyl formamide (50 ml) followed by addition of sodium azide (11.8 g, 181.5 mmol). The mixture was heated to 75° C. for five hours and then added to aqueous sodium chloride (100 ml) followed by extraction with ethyl acetate (3×200 ml). The organic layers were combined, dried over sodium sulfate, and concentrated in vacuo to yield the desired product (15 g).

NMR (DMSO-d$_6$) δ: 3.24 (dd, 1H); 3.55 (dd, 1H); 3.55 (m, 2H); 5.04 (m, 1H); 7.85 (d, 1H); 8.18 (d, 1H); 8.82 (s, 1H).

[3-(5-Bromo-pyridin-2-yl)-4,5-dihydro-isoxazol-5-yl]-methylamine

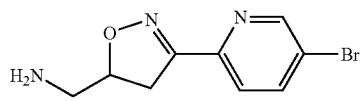

5-Azidomethyl-3-(5-bromo-pyridin-2-yl)-4,5-dihydro-isoxazole (4.4 g, 115.6 mmol) was dissolved in dichloromethane:methanol:water 16:5:1 (88 ml) followed by addition of 25 grams of polystyrene bound triphenylphosphine resin (1.6 mmol per gram). The mixture was stirred for 16 hours and filtered. The resin was washed with dichloromethane (50 ml) and methanol (25 ml) and then the solvents were concentrated in vacuo to give the desired product (3 g).

NMR (DMSO-d$_6$) δ: 1.55 (s, 2H); 2.76 (m, 2H); 3.29 (dd, 1H); 3.43 (dd, 1H); 4.72 (m, 1H); 7.88 (d, 1H); 8.16 (d, 1H); 8.82 (s, 1H).

N-[3-(5-Bromo-pyridin-2-yl)-4,5-dihydro-isoxazol-5-ylmethyl]-acetamide

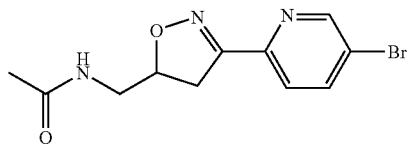

5-Azidomethyl-3-(5-bromo-pyridin-2-yl)-4,5-dihydro-isoxazole (3 g, 10.6 mmol) and thioacetic acid (10 ml) were combined and stirred for 52 hours. The reaction mixture was concentrated in vacuo and then ethyl acetate (20 ml) was added. The resulting precipitate was filtered and washed with ethyl acetate (2×20 ml) to give the desired product (1.8 g).

NMR (DMSO-d$_6$) δ: 1.25 (s, 3H); 3.12 (dd, 1H); 3.22 (t, 2H); 3.41 (dd, 1H); 4.53 (m, 1H); 7.79 (d, 1H); 8.09 (dd, 2H); 8.82 (s, 1H).

1-[3-(5-Bromo-pyridin-2-yl)-4,5-dihydro-isoxazol-5-ylmethyl]-1H-1,2,3-triazole

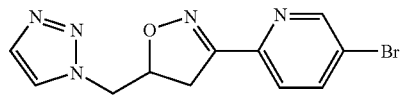

5-Azidomethyl-3-(5-bromo-pyridin-2-yl)-4,5-dihydro-isoxazole (1 g, 3.5 mmol) and bicyclo[2.2.1]hepta-2,5-diene (1 ml) were combined with dioxane (2 ml) and subjected to microwave radiation in a Smith Personal Synthesizer for 900 seconds at 125° C. The reaction mixture was concentrated in vacuo and ethyl acetate (5 ml) was added. The precipitate was filtered and washed with ethyl acetate (2×5 ml) to give the desired product (417 mg).

NMR (DMSO-d$_6$) δ: 3.36 (dd, 1H); 3.62 (dd, 1H); 4.6 (m, 2H); 5.25 (m, 1H); 7.75 (s, 1H); 7.83 (d, 1H); 8.14 (d, 1H); 8.16 (s, 1H); 8.8 (s, 1H).

1-[3-(5-Bromo-pyridin-2-yl)-4,5-dihydro-isoxazol-5-ylmethyl]-4-methyl-1H-1,2,3-triazole

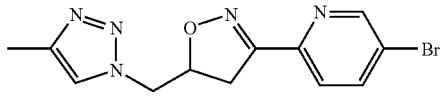

[3-(5-Bromo-pyridin-2-yl)-4,5-dihydro-isoxazol-5-yl]-methylamine (3.4 g, 13.3 mmol) and diisopropylethylamine (11.8 ml, 66.3 mmol) were added to anhydrous methanol (25 ml) followed by addition of N'-[2,2-dichloro-1-methylethylidene]-4-methylbenzenesulfonylhydrazide (5.1 g, 17.3 mmol). The reaction was stirred at room temperature for four hours and then ethyl acetate was added. The precipitate was collected and washed with water (2×25 ml) to give the desired product (793 mg).

NMR (DMSO-d$_6$) δ: 1.98 (s, 3H); 3.10 (dd, 1H); 3.36 (dd, 1H); 4.37 (m, 2H); 4.95 (m, 1H); 7.60 (d, 2H); 7.92 (d, 1H); 8.55 (d, 1H).

[3-(5-Bromo-thien-2-yl)-4,5-dihydro-isoxazol-5-yl]-methanol

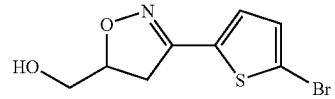

5-Bromo-thiophene-2-carbaldehyde oxime (40.2 g, 195.2 mmol) and allyl alcohol (32.4 ml) were added to tetrahydrofuran (200 ml) and then bleach (1318 ml) was added. The reaction was stirred for four hours followed by extraction with tetrahydrofuran (2×200 ml). The organic layers were combined, dried over sodium sulfate, and concentrated in vacuo to give the desired product (19 g).

NMR (DMSO-d$_6$) δ: 2.95 (dd, 1H); 3.15 (dd, 1H); 3.27 (m, 2H); 4.5 (m, 1H); 4.85 (t, 1H); 7.00 (d, 1H); 7.08 (d, 1H).

Methanesulfonic acid 3-(5-bromo-thien-2-yl)-4,5-dihydro-isoxazol-5-ylmethyl ester

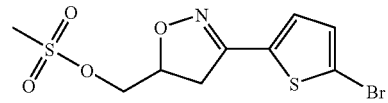

[3-(5-Bromo-thien-2-yl)-4,5-dihydro-isoxazol-5-yl]-methanol (10.7 g, 40.6 mmol) was added to anhydrous dichloromethane (200 ml) followed by addition of triethylamine (7.9 ml, 56.9 mmol). The solution was cooled to 0° C. followed by dropwise addition of methane sulfonyl chloride (3.8 ml, 48.7 mmol). The reaction was stirred for 2 hours at 0° C. and then aqueous sodium bicarbonate (100 ml) was added. After further extraction with dichloromethane (2×100 ml), the organic layers were combined, dried over sodium sulfate, and concentrated in vacuo to give the desired product (9 g).

NMR (DMSO-d$_6$) δ: 3.25 (s, 3H), 3.28 (dd, 1H); 3.57 (dd, 1H); 4.36 (m, 2H); 5.05 (m, 1H); 7.27 (d, 1H); 7.32 (d, 1H).

5-Azidomethyl-3-(5-bromo-thien-2-yl)-4,5-dihydro-isoxazole

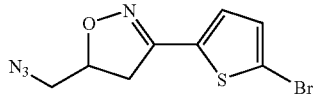

Methanesulfonic acid 3-(5-bromo-thien-2-yl)-4,5-dihydro-isoxazol-5-ylmethyl ester (9 g, 26.4 mmol) was added to dimethyl formamide (25 ml) followed by addition of sodium azide (3.4 g, 52.8 mmol). The mixture was heated to 75° C. for five hours and then added to aqueous sodium chloride (100 ml) followed by extraction with ethyl acetate (3×200 ml). The organic layers were combined, dried over sodium sulfate, and concentrated in vacuo to yield the desired product (7.4 g).

NMR (DMSO-$d_6$) δ: 3.01 (dd, 1H); 3.3 (dd, 1H); 3.42 (d, 1H); 4.75 (m, 1H); 7.07 (d, 1H); 7.14 (d, 1H); 7.78 (s, 1H).

[3-(5-Bromo-thien-2-yl)-4,5-dihydro-isoxazol-5-yl]-methylamine

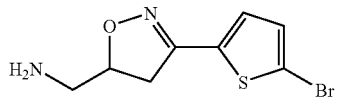

5-Azidomethyl-3-(5-bromo-thien-2-yl)-4,5-dihydro-isoxazole (5 g, 17.4 mmol) was dissolved in dichloromethane:methanol:water 16:5:1 (88 ml) followed by addition of 20 grams of polystyrene bound triphenylphosphine resin (1.6 mmol per gram). The mixture was stirred for 16 hours and filtered. The resin was washed with dichloromethane (50 ml) and methanol (25 ml) and then the solvents were concentrated in vacuo to give the desired product (4.3 g).

NMR (DMSO-$d_6$) δ: 2.55 (m, 2H), 3.01 (dd, 1H); 3.2 (dd, 1H); 4.46 (m, 1H); 6.99 (d, 1H); 7.12 (d, 1H).

N-[3-(5-Bromo-thien-2-yl)-4,5-dihydro-isoxazol-5-ylmethyl]-acetamide

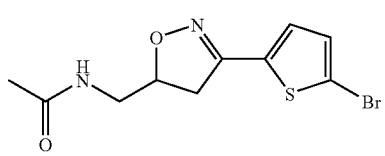

[3-(5-Bromo-thien-2-yl)-4,5-dihydro-isoxazol-5-yl]-methylamine (2.1 g, 8 mmol) and triethylamine (1.7 ml, 12 mmol) were added to anhydrous dichloromethane (50 ml) and cooled to 0° C. Acetyl chloride (0.670 ml, 9.6 mmol) was then added dropwise and the reaction was stirred for 3 hours followed by addition of ethyl acetate (100 ml). The precipitate was collected and washed with water (2×25 ml) to give the desired product (1.2 g).

NMR (DMSO-$d_6$) δ: 1.86 (s, 3H), 3.15 (dd, 1H); 3.3 (m, 2H); 3.55 (dd, 1H); 4.8 (m, 1H); 7.2 (d, 1H); 7.35 (d, 1H), 8.2 (t, 1H).

1-[3-(5-Bromo-thien-2-yl)-4,5-dihydro-isoxazol-5-ylmethyl]-1H-1,2,3-triazole

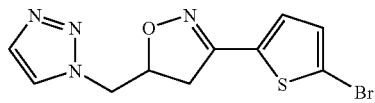

5-Azidomethyl-3-(5-bromo-thien-2-yl)-4,5-dihydro-isoxazole (500 mg, 1.74 mmol) and bicyclo[2.2.1]hepta-2,5-diene (1 ml) were combined with dioxane (2 ml) and subjected to microwave radiation in a Smith Personal Synthesizer for 900 seconds at 125° C. The reaction mixture was concentrated in vacuo and ethyl acetate (5 ml) was added. The precipitate was filtered and washed with ethyl acetate (2×5 ml) to give the desired product (234 mg).

NMR (DMSO-$d_6$) δ: 3.28 (dd, 1H); 3.59 (dd, 1H); 4.66 (m, 2H); 5.18 (m, 1H); 7.24 (d, 1H); 7.35 (d, 1H), 7.78 (d, 1H), 8.17 (s, 1H).

1-[3-(5-Bromo-thien-2-yl)-4,5-dihydro-isoxazol-5-ylmethyl]-4-methyl-1H-1,2,3-triazole

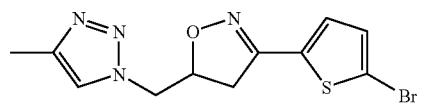

[3-(5-Bromo-thien-2-yl)-4,5-dihydro-isoxazol-5-yl]-methylamine (2.2 g, 8.4 mmol) and diisopropylethylamine (7.3 ml, 42 mmol) were added to anhydrous methanol (50 ml) followed by addition of N'-[2,2-dichloro-1-methylethylidene]-4-methylbenzenesulfonohydrazide (3.2 g, 10.9 mmol). The reaction was stirred at room temperature for four hours and then ethyl acetate was added. The precipitate was collected and washed with water (2×25 ml) to give the desired product (793 mg).

NMR (DMSO-$d_6$) δ: 2.23 (s, 3H); 3.23 (dd, 1H); 3.55 (dd, 1H); 4.55 (m, 2H); 5.16 (m, 1H); 7.23 (d, 1H); 7.33 (d, 1H), 7.83 (s, 1H).

(5R)-3-(5-Bromopyrid-2-yl)-2-oxo-1,3-oxazolidin-5-yl]methyl methanesulfonate

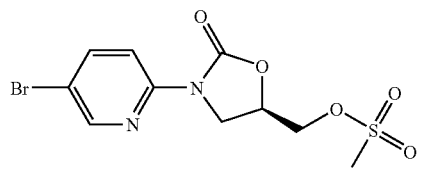

(5R)-3-(5-Bromopyrid-2-yl)-5-(hydroxymethyl)-1,3-oxazolidin-2-one (15.4 g, 56.4 mM) was dissolved in methylene chloride (150 ml). Triethylamine (8.00 g, 78.9 mM) was added and the solution was degassed. Methanesulfonyl chloride (7.75 g, 67.7 mM) was added dropwise and the reaction was stirred at 0° for 4 hours. The mixture was diluted with aqueous sodium bicarbonate and the compound was extracted using methylene chloride. The organic layer was washed with brine, dried (magnesium sulfate) and evaporated to give a light orange solid (21.24 g).

MS (ESP): 352 (MH$^+$) for $C_{10}H_{11}BrN_2O_5S$

NMR (DMSO-d$_6$) δ: 3.27 (s, 3H); 3.94 (dd, 1H); 4.28 (t, 1H); 4.54 (dq, 2H); 5.05 (m, 1H); 8.07-8.09 (m, 2H); 8.53 (s, 1H).

(5R)-5-(Azidomethyl)-3-(5-bromopyrid-2-yl)-1,3-oxazolidin-2-one

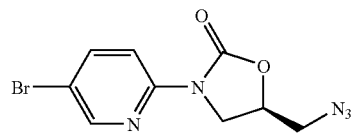

(5R)-3-(5-Bromopyrid-2-yl)-2-oxo-1,3-oxazolidin-5-yl] methyl methanesulfonate (21.24 g, 56.4 mM) was dissolved in N,N-dimethylformamide (200 ml). Sodium azide (7.33 g, 113 mM) was added and the reaction was heated at 75° for 16.5 hours. The mixture was cooled, diluted with ethyl acetate, washed with sodium bicarbonate followed by water, dried (magnesium sulfate), and evaporated in vacuo to give a light yellow solid (16.8 g).

NMR (DMSO-d$_6$) δ: 3.78 (dq, 2H); 3.88 (dd, 1H); 4.25 (t, 1H); 4.93 (m, 1H); 8.08 (m, 2H); 8.51 (s, 1H).

(5R)-3-(5-Bromopyrid-2-yl)-5-(1H-1,2,3-triazol-1-ylmethyl)-1,3-oxazolidin-2-one

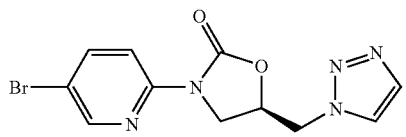

(5R)-5-(Azidomethyl)-3-(5-bromopyrid-2-yl)-1,3-oxazolidin-2-one (5.60 g, 18.7 mM) was dissolved in 1,4-dioxane (12 ml). Bicyclo[2.2.1]hepta-2,5-diene (10.3 g, 112 mM) was added and the yellow solution was stirred at 100° for 16 hours. The brown solution was concentrated and the residue was purified by flash chromatography eluting with ethyl acetate. Relevant fractions were combined to give the desired product (4.36 g) as a beige solid.

MS (ESP): 324 (MH$^+$) for $C_{11}H_{10}BrN_5O_2$

NMR (DMSO-d$_6$) δ: 4.23 (m, 1H); 4.53 (dd, 1H); 5.09-5.11 (m, 2H); 5.40 (m, 1H); 8.00 (s, 1H); 8.21 (d, 1H); 8.30 (dd, 1H); 8.40 (s, 1H); 8.74 (d, 1H).

N-{[(5S)-3-(5-Bromopyrid-2-yl)-2-oxo-1,3-oxazolidin-5-yl]methyl}acetamide

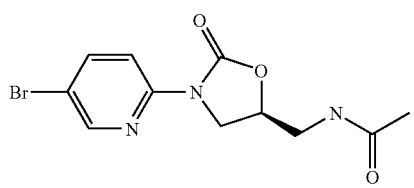

(5R)-5-(Azidomethyl)-3-(5-bromopyrid-2-yl)-1,3-oxazolidin-2-one (5.60 g, 18.7 mM) was dissolved in thioacetic acid (10 ml) to give a yellow solution. The solution was degassed and stirred at room temperature for 20 hours. The thick slurry was concentrated and the desired product was crystallized from acetone (100 ml) to give the product as a light yellow solid (3.25 g).

MS (ESP): 315 (MH$^+$) for $C_{11}H_{12}BrN_3O_3$

NMR (DMSO-d$_6$) δ: 1.84 (s, 3H); 3.453-3.46 (m, 2H); 3.86 (dd, 1H); 4.20 (t, 1H); 4.76 (m, 1H); 8.08 (s, 2H); 8.25 (t, 1H); 8.52 (s, 1H).

(5S)-5-(Aminomethyl)-3-(5-bromopyrid-2-yl)-1,3-oxazolidin-2-one

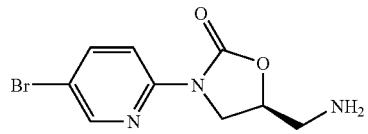

(5R)-5-(Azidomethyl)-3-(5-bromopyrid-2-yl)-1,3-oxazolidin-2-one (5.60 g, 18.7 mM) was dissolved in acetonitrile:water (100:10 ml). Triphenylphosphine (5.42 g, 20.7 mM) was added. The reaction mixture was degassed and stirred at room temperature for 48 hours. The light yellow liquid was concentrated and the residue was purified by flash chromatography eluting with ethyl acetate then 6% methanol in ethyl acetate. Relevant fractions were combined to give the desired product as a light yellow solid (4.54 g).

MS (ESP): 272 (MH$^+$) for $C_9H_{10}BrN_3O_2$.

NMR (DMSO-d$_6$) δ: 1.7 (s, 2H); 2.85 (dq, 2H); 3.95 (m, 1H); 4.16 (t, 1H); 4.65 (m, 1H); 8.05-8.10 (m, 2H); 8.51 (m, 1H).

(5R)-3-(5-Bromopyrid-2-yl)-5-[(4-methyl-1H-1,2,3-triazol-1-yl)methyl]-1,3-oxazolidin-2-one

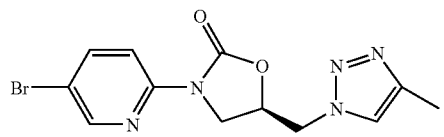

(5S)-5-(Aminomethyl)-3-(5-bromopyrid-2-yl)-1,3-oxazolidin-2-one (4.54 g, 16.7 mM) was dissolved in methanol (100 ml). Diisopropylethylamine (5.86 g, 20.9 mM) was added and the reaction was cooled to 0° in an ice bath. Toluenesulfonic acid 2-(2,2-dichloro-1-methylethylidene)hydrazide (5.86 g, 20.9 mM) was added to give an orange solution. The reaction was stirred overnight while slowly warming to room temperature. The desired product precipitated as a yellow solid (4.10 g) and was filtered.

MS (ESP): 338 (MH$^+$) for $C_{12}H_{12}BrN_5O_2$

NMR (DMSO-d$_6$) δ: 2.24 (s, 3H); 3.99 (dd, 1H); 4.29 (t, 1H); 4.78-4.80 (m, 2H); 5.13 (m, 1H); 7.87 (s, 1H); 8.00 (d, 1H); 8.08 (dd, 1H); 8.52 (d, 1H).

(5R)-3-(4-Iodophenyl)-5-(1H-1,2,3-triazol-1-ylmethyl)-1,3-oxazolidin-2-one

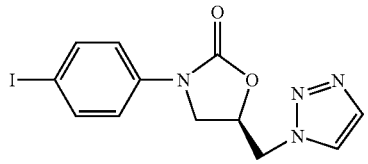

(5R)-5-(Azidomethyl)-3-(4-iodophenyl)-1,3-oxazolidin-2-one (10.0 g, 29.1 mmol) was dissolved in 1,4-dioxane (100 ml). Bicyclo[2.2.1]hepta-2,5-diene (9.4 ml, 87.2 mmol) was added and the mixture heated to 100° C. for 24 h. The solution was cooled and purified by silica flash chromatography with 1-10% methanol in dichloromethane as eluent giving 7.2 g of the desired product.

MS (ESP) 370.96 (MH+) for $C_{12}H_{11}IN_4O_2$.

$^1$H-NMR (DMSO-d$_6$) δ: 3.88 (dd, 1H); 4.22 (t, 1H); 4.84 (d, 2H); 5.13 (m, 1H); 7.31 (d, 2H); 7.70 (s, 1H); 7.75 (d, 2H); 8.16 (s, 1H).

(5S)-5-(Aminomethyl)-3-(4-iodophenyl)-1,3-oxazolidin-2-one

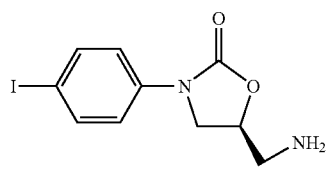

(5R)-5-(Azidomethyl)-3-(4-iodophenyl)-1,3-oxazolidin-2-one (8.0 g, 23.2 mmol) was dissolved in acetonitrile (160 ml) and water (16 ml). Triphenylphosphine (7.3 g, 27.9 mmol) was added and the mixture stirred at room temperature overnight. The volatiles were removed by concentration in vacuo, and the resulting residue partitioned between water (200 ml) and dichloromethane (200 ml). The aqueous layer was extracted with dichloromethane (2×200 ml) and dried over sodium sulfate. The crude material was purified by flash chromatography on silica gel with 0-10% methanol in dichloromethane as the eluent giving the desired product (6.0 g).

$^1$H-NMR (DMSO-d$_6$) δ: 1.73 (br s, 2H); 2.82 (m, 2H); 3.83 (dd, 1H); 4.04 (t, 1H); 4.61 (m, 1H); 7.41 (d, 2H); 7.72 (d, 2H).

(5R)-3-(4-Iodophenyl)-5-[(4-methyl-1H-1,2,3-triazol-1-yl)methyl]-1,3-oxazolidin-2-one

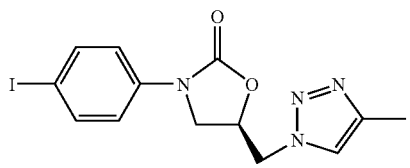

(5S)-5-(Aminomethyl)-3-(4-iodophenyl)-1,3-oxazolidin-2-one (6.0 g, 18.9 mmol) was dissolved in methanol (150 ml, c=0.1M) and cooled to 0° C. Diisopropylethylamine (13.1 ml, 75.4 mmol) was added and the reaction stirred at 0° C. for 5 min; toluenesulfonic acid 2-(2,2-dichloro-1-methylethylidene)hydrazide was then added and the reaction stirred overnight. The volatiles were concentrated in vacuo, dichloromethane was added and some product crystallized from solution; the remaining residue was purified by flash chromatography on silica gel using 0-5% methanol in dichloromethane as the eluent. The relevant fractions were combined giving 5.5 g of the desired product.

MS (ESP) 384.98 (MH+) for $C_{13}H_{13}IN_4O_2$.

$^1$H-NMR (DMSO-d$_6$) δ: 2.22 (s, 3H); 3.86 (dd, 1H); 4.20 (t, 1H); 4.75 (d, 2H); 5.09 (m, 1H); 7.33 (d, 2H); 7.72 (d, 2H); 7.86 (s, 1H).

(5R)-5-(Azidomethyl)-3-(4-iodophenyl)-1,3-oxazolidin-2-one

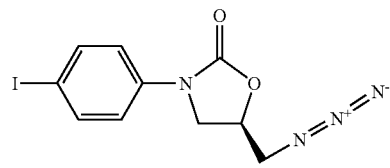

[(5R)-3-(4-Iodophenyl)-2-oxo-1,3-oxazolidin-5-yl]methyl methanesulfonate (27 g, 68 mmol) was dissolved in dimethylacetamide (300 ml). Sodium azide (13.1 g, 202 mmol) was carefully added, and the solution was heated to 80° C. for 3 h. After cooling to room temperature, the mixture was diluted with ethyl acetate (500 ml), washed with water (2×), brine, and dried over sodium sulfate. Flash chromatography with 0-1% methanol in dichloromethane as eluent gave the desired product (19 g).

MS (ESP) 344.93 (MH+) for C10H9IN4O2.

$^1$H-NMR (DMSO-d$_6$) δ: 3.74 (overlapping m, 3H); 4.12 (t, 1H); 4.89 (m, 1H); 7.41 (d, 2H); 7.74 (d, 2H).

[(5R)-3-(4-Iodophenyl)-2-oxo-1,3-oxazolidin-5-yl] methyl methanesulfonate

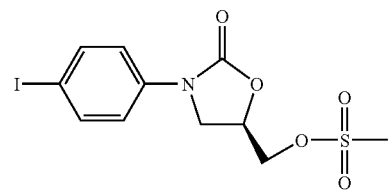

[(5R)-3-phenyl-2-oxo-1,3-oxazolidin-5-yl]methyl methanesulfonate (41 g, 152 mmol) was dissolved in chloroform/acetonitrile (250/250 ml). Silver trifluoroacetate (50 g, 228 mmol) was added followed by portionwise addition of iodine (58 g, 228 mmol). After stirring the reaction overnight, the silver iodide was filtered off, and the filtrate was washed with solutions of 5% sodium thiosulfate (2×500 ml), saturated sodium bicarbonate (500 ml), brine, and dried over magnesium sulfate. The dried solution was evaorated to give the desired product as a yellow solid (32 g) that was used without further purification.

MS (ESP) 397.93 (MH+) for C11H12INO5S.

¹H-NMR (DMSO-d₆) δ: 3.25 (s, 3H); 3.80 (dd, 1H); 4.17 (t, 1H); 4.49 (m, 2H); 5.00 (m, 1H); 7.40 (d, 2H); 7.74 (d, 2H).

[(5R)-3-Phenyl-2-oxo-1,3-oxazolidin-5-yl]methyl methanesulfonate

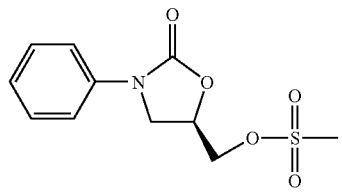

W. A. Gregory et al, J. Med. Chem., 32, 1673-1681 (1989).

[5R)-5-(Hydroxymethyl)-3-(4-iodophenyl)-1,3-oxazolidin-2-one

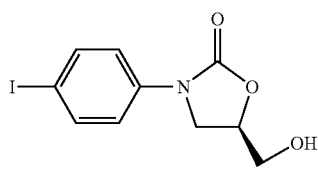

M. B. Gravestock, WO 99/64417

[(5R)-3-(4-Iodophenyl)-2-oxo-1,3-oxazolidin-5-yl] methyl acetate

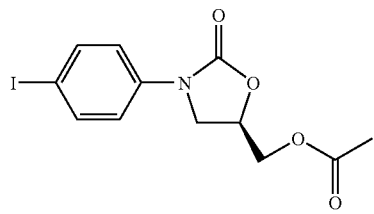

W. A. Gregory et al, J. Med. Chem., 33, 2569-2578 (1990).

[(5R)-3-Phenyl-2-oxo-1,3-oxazolidin-5-yl]methyl acetate

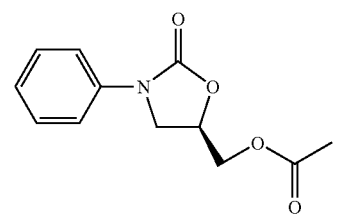

W. A. Gregory et al, J. Med. Chem., 32, 1673-1681 (1989).

EXAMPLES

Example 1

(5S,5'S)-N-(3-{4'-[5-(Acetylamino-methyl)-2-oxo-oxazolidin-3-yl]-2,2'-difluoro-biphenyl-4-yl}-2-oxo-oxazolidin-5-ylmethyl)-acetamide

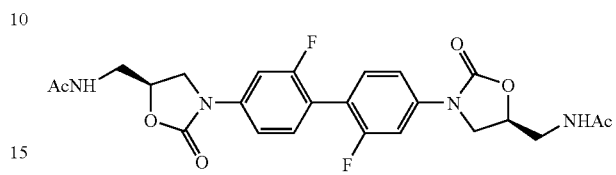

(5S)-N-[3-(3-Fluoro-4-iodo-phenyl)-2-oxo-oxazolidin-5-ylmethyl]acetamide (150 mg, 0.4 mM, see Upjohn WO 94-13649) and tetrabutylammonium bromide (129 mg, 0.4 mM) were stirred in a mixture of N,N-dimethylformamide (0.5 ml) and triethylamine (210 mg, 2 mM), and degassed by bubbling nitrogen. Palladium(II) acetate (8 mg, 0.04 mM) was added, and the whole heated at 70° for 18 hours. The mixture was cooled, diluted with ethyl acetate (50 ml), washed with saturated sodium bicarbonate (2×20 ml), dried (magnesium sulfate) and evaporated. The residue was purified by chromatography on a 10 g silica Mega Bond Elut® column, eluting with a gradient increasing in polarity from 0 to 100% ethyl acetate in dichloromethane, then 0 to 20% methanol in dichloromethane. Relevant fractions were combined to give the desired product (47 mg), after trituration with a little methanol.

MS (ESP): 503 (MH⁺) for $C_{24}H_{24}F_2N_4O_6$

NMR (DMSO-d₆) δ: 1.84 (s, 6H); 3.43 (t, 4H); 3.79 (dd, 2H); 4.18 (t, 2H); 4.76 (m, 2H); 7.44 (overlapping m, 4H); 7.59 (m, 2H); 8.22 (t, 2H).

Example 2

Acetic acid (5R,5'R)-3-[4'-(5-acetoxymethyl-2-oxo-oxazolidin-3-yl)-2,2'-difluoro-biphenyl-4-yl]-2-oxo-oxazolidin-5-ylmethyl ester

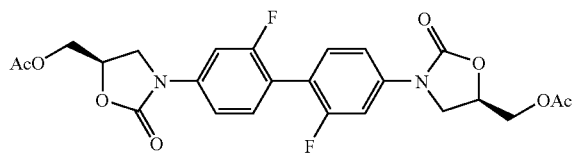

Using essentially the procedure of Example 1, but starting from acetic acid (5R)-3-(3-fluoro-4-iodo-phenyl)-2-oxo-oxazolidin-5-ylmethyl ester (3.79 g, 10 mM) gave the title compound (0.94 g) after chromatography.

MS (ESP): 505 (MH⁺) for $C_{24}H_{22}F_2N_2O_8$

NMR (DMSO-d₆) δ: 2.05 (s, 6H); 3.89 (dd, 2H); 4.21 (t, 2H); 4.28 (dd, 2H); 4.35 (dd, 2H); 4.98 (m, 2H); 7.47 (overlapping m, 4H); 7.60 (m, 2H).

The intermediates for this compound were prepared as follows:

Acetic acid (5R)-3-(3-fluoro-phenyl)-2-oxo-oxazolidin-5-ylmethyl ester (5R)-3-(3-Fluorophenyl)-5-hydroxymethyloxazolidin-2-one (40 g, 0.189 M, see Upjohn WO 94-13649) was suspended by stirring in dry dichloromethane (400 ml) under nitrogen. Triethylamine (21 g, 0.208 M) and 4-dimethylaminopyridine (0.6 g, 4.9 mM) were added, followed by dropwise addition of acetic anhydride (20.3 g, 0.199 M) over 30 minutes, and stirring continued at ambient temperature for 18 hours. Saturated aqueous sodium bicarbonate (250 ml) was added, the organic phase separated, washed with 2% sodium dihydrogen phosphate, dried (magnesium sulfate), filtered and evaporated to give the desired product (49.6 g) as an oil.

MS (ESP): 254 (MH$^+$) for $C_{12}H_{12}FNO_4$

NMR (CDCl$_3$) δ: 2.02 (s, 3H); 3.84 (dd, 1H); 4.16 (t, 1H); 4.25 (dd, 1H); 4.32 (dd, 1H); 4.95 (m, 1H); 6.95 (td, 1H); 7.32 (d, 1H); 7.43 (t, 1H); 7.51 (d, 1H).

Acetic acid (5R)-3-(3-fluoro-4-iodo-phenyl)-2-oxo-oxazolidin-5-ylmethyl ester

Acetic acid (5R)-3-(3-fluoro-phenyl)-2-oxo-oxazolidin-5-ylmethyl ester (15.2 g, 60 mM) was dissolved in a mixture of chloroform (100 ml) and acetonitrile (100 ml) under nitrogen, and silver trifluoroacetate (16.96 g, 77 mM) added. Iodine (18.07 g, 71 mM) was added in portions over 30 minutes to the vigorously stirred solution, and stirring continued at ambient temperature for 18 hours. As reaction was not complete, a further portion of silver trifluoroacetate (2.64 g, 12 mM) was added and stirring continued for 18 hours. After filtration, the mixture was added to sodium thiosulfate solution (3%, 200 ml) and dichloromethane (200 ml), and the organic phase separated, washed with sodium thiosulfate (200 ml), saturated aqueous sodium bicarbonate (200 ml), brine (200 ml), dried (magnesium sulfate), filtered and evaporated. The crude product was suspended in isohexane (100 ml), and sufficient diethyl ether added to dissolve out the brown impurity while stirring for 1 hour. Filtration gave the desired product (24.3 g) as a cream solid.

MS (ESP): 380 (MH$^+$) for $C_{12}H_{11}FINO_4$

NMR (DMSO-d$_6$) δ: 2.03 (s, 3H); 3.82 (dd, 1H); 4.15 (t, 1H); 4.24 (dd, 1H); 4.30 (dd, 1H); 4.94 (m, 1H); 7.19 (dd, 1H); 7.55 (dd, 1H); 7.84 (t, 1H).

Example 3

(5R,5'R)-4,4'-Bis-(5-hydroxymethyl-2-oxo-oxazolidin-3-yl)-2,2'-difluoro-biphenyl

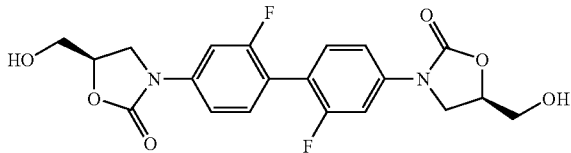

Acetic acid (5R,5'R)-3-[4'-(5-acetoxymethyl-2-oxo-oxazolidin-3-yl)-2,2'-difluoro-biphenyl-4-yl]-2-oxo-oxazolidin-5-ylmethyl ester (940 mg, 1.86 mM) was stirred in a mixture of methanol (70 ml) and dichloromethane (60 ml), potassium carbonate (600 mg, 4.34 mM) added, and stirring continued at ambient temperature for 20 minutes. After neutralisation by addition of the minimum of acetic acid, the mixture was diluted with water (50 ml), and organic solvent evaporated to give an aqueous suspension. Solid was filtered, washed with water and a little diethyl ether, and dried to give the desired product (740 mg).

MS (ESP): 421 (MH$^+$) for $C_{20}H_{18}F_2N_2O_6$

NMR (DMSO-d$_6$) δ: 3.59 (m, 2H); 3.70 (m, 2H); 3.88 (dd, 2H); 4.13 (t, 2H); 4.73 (m, 2H); 5.21 (t, 2H); 7.47 (s, 4H); 7.61 (dd, 2H).

Example 4

(5S,5'S)-4,4'-Bis-(5-isoxazol-3-ylaminomethyl-2-oxo-oxazolidin-3-yl)-2,2'-difluoro-biphenyl

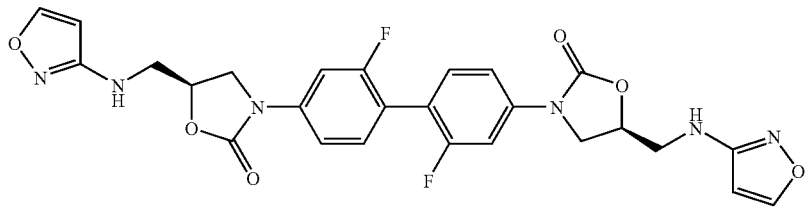

N-(5R, 5'R)-(3-{4'-[5-N-(tert-Butoxycarbonyl)isoxazol-3-ylamino-methyl)-2-oxo-oxazolidin-3-yl]-2,2'-difluoro-1,1'-biphenyl-4-yl}-2-oxo-oxazolidin-5-ylmethyl)N-isoxazol-3-yl-carbamic acid tert-butyl ester (150 mg, 0.2 mM) was dissolved in dichloromethane (5 ml), treated with trifluoroacetic acid (5 ml), stirred at ambient temperature for 1 hour, and solvent evaporated. The residue was treated with dilute aqueous ammonia, extracted with ethyl acetate (20 ml), the organic layer washed with water (10 ml), brine (10 ml), dried (magnesium sulfate), and evaporated. The residue was purified by chromatography on a 10 g silica Mega Bond Elut® column, eluting with a gradient increasing in polarity from 0 to 10% methanol in dichloromethane. Relevant fractions were combined to give the title product. (39 mg).

MS (Negative ESP): 597 (M–H$^-$) for $C_{26}H_{22}F_2N_6O_6$+ HCOOH

NMR (DMSO-d$_6$) δ: 3.46 (t, 4H); 3.86 (dd, 2H); 4.21 (t, 2H); 4.91 (m, 2H); 6.01 (d, 2H); 6.55 (t, 2H); 7.44 (overlapping m, 4H); 7.61 (dd, 2H); 8.39 (d, 2H).

The intermediates for this compound were prepared as follows:

(5R)-3-(3-Fluoro-4-iodophenyl)-5-hydroxymethyloxazolidin-2-one

Acetic acid (5R)-3-(3-fluoro-4-iodophenyl)-2-oxo-oxazolidin-5-ylmethyl ester (30 g, 79 mM) was treated with potassium carbonate (16.4 g, 0.119 mM) in a mixture of methanol (800 ml) and dichloromethane (240 ml) at ambient temperature for 25 minutes, then immediately neutralised by the addition of acetic acid (10 ml) and water (500 ml). The precipitate was filtered, washed with water, and dissolved in dichloromethane (1.2 L), the solution washed with saturated sodium bicarbonate, and dried (magnesium sulfate). Filtration and evaporation gave the desired product (23 g).

MS (ESP): 338 (MH$^+$) for $C_{10}H_9FINO_3$

NMR (DMSO-d$_6$) δ: 3.53 (m, 1H); 3.67 (m, 1H); 3.82 (dd, 1H); 4.07 (t, 1H); 4.70 (m, 1H); 5.20 (t, 1H); 7.21 (dd, 1H); 7.57 (dd, 1H); 7.81 (t, 1H).

Methanesulfonic acid (5R)-3-(3-fluoro-4-iodo-phenyl)-2-oxo-oxazolidin-5-ylmethyl ester (5R)-3-(3-Fluoro-4-iodophenyl)-5-(hydroxymethyl)oxazolidin-2-one (6.07 g, 18 mM) in dry dichloromethane (200 ml) under nitrogen was treated with triethylamine (2.54 g, 25 mM), and methanesulfonyl chloride (2.47 g, 22 mM) run in dropwise over 30 minutes at 0°. After stirring 2 hours at 0°, the mixture was diluted with water (200 ml), the organic layer separated, washed with hydrochloric acid (2N, 100 ml), sodium bicarbonate solution (5%, 100 ml), brine (100 ml) and dried (magnesium sulfate). The residue after evaporation was dissolved in the minimum of dichloromethane, and excess isohexane added to precipitate the desired product (7.05 g).

MS (ESP): 416 (MH$^+$) for $C_{11}H_{11}FINO_5S$

NMR (DMSO-d$_6$) δ: 3.26 (s, 3H); 3.81 (dd, 1H); 4.18 (t, 1H); 4.46 (dd, 1H); 4.53 (dd, 1H); 5.01 (m, 1H); 7.20 (dd, 1H); 7.57 (dd, 1H); 7.83 (t, 1H).

N-(5R)-[3-(3-Fluoro-4-iodo-phenyl)-2-oxo-oxazolidin-5-ylmethyl]N—isoxazol-3-yl-carbamic acid tert-butyl ester

To sodium hydride (60% in oil, 9.04 mM) suspended in dry N,N-dimethylformamide (10 ml) under nitrogen, N-isoxazol-3-yl-carbamic acid tert-butyl ester (1.66 g, 9.04 mM) in N,N-dimethylformamide (10 ml) was added dropwise at ambient temperature. Methanesulfonic acid (5R)-3-(3-fluoro-4-iodo-phenyl)-2-oxo-oxazolidin-5-ylmethyl ester (2.5 g, 6.02 mM) in N,N-dimethylformamide (10 ml) was added slowly, and the mixture heated to 75° for 2 hours. After cooling, the mixture was diluted with aqueous sodium bicarbonate (5%, 300 ml), and extracted with ethyl acetate (3×100 ml). The organic phase was washed with water (100 ml) and brine (100 ml), dried (magnesium sulfate), evaporated and crude product purified by chromatography on a 50 g silica Mega Bond Elut® column, eluting with dichloromethane. Relevant fractions were combined to give the title compound (1.73 g).

MS (ESP): 504 (MH$^+$) for $C_{18}H_{19}FIN_3O_5$

NMR (DMSO-d$_6$) δ: 1.47 (s, 9H); 3.84 (dd, 1H); 3.96 (dd, 1H); 4.19 (t, 1H); 4.99 (dd, 1H); 4.99 (m, 1H); 6.83 (d, 1H); 7.19 (dd, 1H); 7.53 (dd, 1H); 7.82 (dd, 1H); 8.79 (d, 1H).

N-(5R)-[3-(3-Fluoro-4-trimethylstannanyl-phenyl)-2-oxo-oxazolidin-5-ylmethyl]N—isoxazol-3-yl-carbamic acid tert-butyl ester

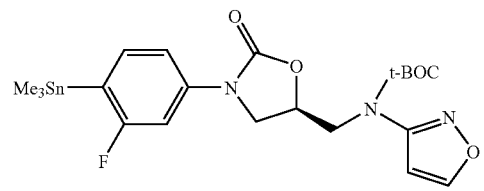

N-(5R)-[3-(3-fluoro-4-iodo-phenyl)-2-oxo-oxazoldin-5-ylmethyl]N—isoxazol-3-yl-carbamic acid tert-butyl ester (1.44 g, 2.86 mM) in anhydrous dioxan (150 ml) was degassed by bubbling nitrogen, and a solution of hexamethylditin (slight mol. equiv. excess) in dioxan (50 ml) added, followed by bis(triphenylphosphine)palladium(II) chloride (0.1 mol. equiv.). The mixture was heated at 110° for 20 hours, cooled, filtered through celite and solvent evaporated. The residue was purified by chromatography on a 50 g silica Mega Bond Elut® column eluting with a gradient from 0% to 100% dichloromethane in isohexane. Relevant fractions were combined to give the desired product (1.2 g).

NMR (DMSO-d$_6$) δ: 0.33 (s, 9H); 1.50 (s, 9H); 3.86 (dd, 1H); 4.00 (dd, 1H); 4.24 (t, 1H); 4.28 (dd, 1H); 5.02 (m, 1H); 6.87 (d, 1H); 7.10 (dd, 1H); 7.43 (overlapping m, 2H); 8.82 (d, 1H).

N-(5R,5'R)-(3-{4'-[5-N-(tert-Butoxycarbonyl)isoxazol-3-ylamino-methyl)-2-oxo-oxazolidin-3-yl]-2,2'-difluoro-biphenyl-4-yl}-2-oxo-oxazolidin-5-ylmethyl)N—isoxazol-3-yl-carbamic acid tert-butyl ester

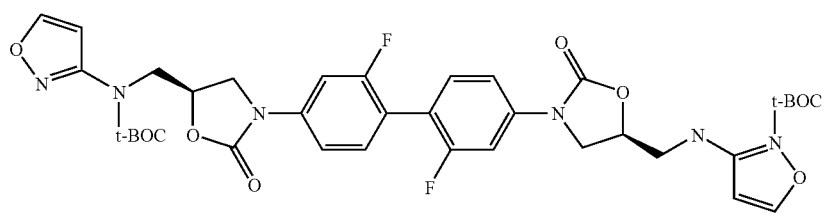

N-(5R)-[3-(3-Fluoro-4-trimethylstannyl-phenyl)-2-oxo-oxazolidin-5-ylmethyl]N—isoxazol-3-yl-carbamic acid tert-butyl ester (540 mg, 1 mM) and copper (I) iodide (0.2 mol. equiv.) were suspended in dry N,N-dimethylformamide (3 ml) and degassed by bubbling nitrogen. Tetrakis(triphenylphosphine)palladium(0) (0.05 mol. equiv.) was added, and the mixture heated under nitrogen at 70° for 18 hours. After cooling, a solution of potassium fluoride (10%, 10 ml) was added, and the mixture stirred 15 minutes. After dilution with water (50 ml), organic material was extracted with ethyl acetate (40 ml), the organic layer washed with water (2×20 ml), brine (20 ml), dried (magnesium sulfate), and evaporated. The residue was purified by chromatography on a 20 g silica Mega Bond Elut® column, eluting with a gradient increasing in polarity from 0 to 100% ethyl acetate in dichloromethane. Relevant fractions were combined to give the title product (191 mg).

NMR (DMSO-$d_6$) δ: 1.50 (s, 18H); 3.91 (dd, 2H); 4.01 (dd, 2H); 4.38 (overlapping m, 4H); 5.04 (m, 2H); 6.86 (d, 2H); 7.49 (m, 4H); 7.60 (dd, 2H); 8.81 (d, 2H).

Example 5

((5R,5'RS)-3-{2-Fluoro-4'-[5'-(hydroxymethyl)-4,5-dihydroisoxazol-3-yl]-1,1'-biphenyl-4-yl}-2-oxo-1,3-oxazolidin-5-yl)methyl acetate

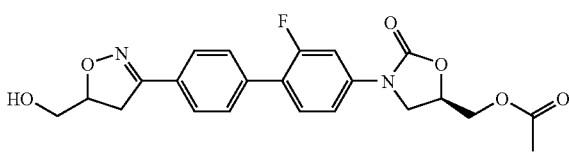

To a solution of [(5R)-3-(3-fluoro-4-iodophenyl)-2-oxo-1,3-oxazolidin-5-yl]methyl acetate (500 mg, 1.32 mM, see Upjohn WO 94-13649) and dichloro[1,1'-bis(diphenylphosphinyl)ferrocene]palladium (II) dichloromethane adduct (32 mg, 0.04 mM) in tetrahydrofuran (6 mL) was added triethylamine (0.55 mL, 3.96 mM) followed by pinacolborane (0.57 mL, 3.96 mM). The mixture was stirred under nitrogen at 65° C. After ca. 16 hours, water (600 μL), potassium carbonate (547 mg, 3.96 mM), palladium (II) acetate (15 mg, 0.07 mM), 2-(di-t-butylphosphinyl)biphenyl (79 mg, 0.26 mM) and [3-(4-bromophenyl)-4,5-dihydroisoxazol-5-yl]methanol (280 mg, 1.09 mM, see Pharmacia & Upjohn WO 98-07708),) were added and the resulting mixture was stirred at 65° C. for ca. 36 hours. The mixture was poured into water and extracted twice with ethyl acetate. The combined organics were washed with brine, dried over magnesium sulfate and evaporated. The residue was purified on silica gel with 75% ethyl acetate/hexanes to give 38 mg of the desired product.

MS (APCI): 429 (M+1) for $C_{22}H_{21}FN_2O_6$

NMR (DMSO-$d_6$) δ: 2.07 (s, 3H); 3.25 (dd 1H); 3.46 (dd, 1H); 3.53-3.56 (m, 2H); 3.91 (dd, 1H); 4.24 (t, 1H); 4.29-4.37 (m, 2H); 4.76 (m, 1H); 4.99-5.04 (m, 2H); 7.49 (dd, 1H); 7.63-7.67 (m, 4H); 7.78 (d, 2H).

Example 6

N-[((5S,5'RS)-3-{4'-{5-({[tert-Butyl(dimethyl)silyl]oxy}methyl)-4,5-dihydroisoxazol-3-yl]-1,1'-biphenyl-4-yl}-2-oxo-1,3-oxazolidin-5-yl)methyl]acetamide

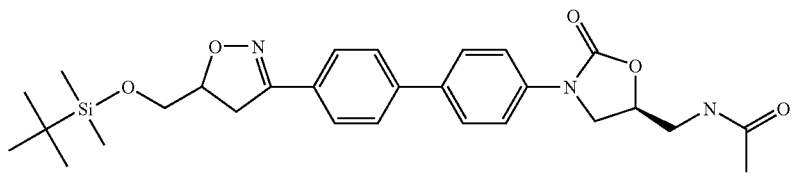

N-({(5S)-2-Oxo-3-[4-(trimethylstannyl)phenyl]-1,3-oxazolidin-5-yl}methyl)acetamide (800 mg, 2.01 mM), (5RS)-3-(4-bromophenyl)-5-({[tert-butyl(dimethyl)silyl]oxy}methyl)-4,5-dihydroisoxazole (746 mg, 2.01 mM), tris(dibenzylidineacetone)dipalladium (0) chloroform adduct (83 mg, 0.080 mM), and tri-2-furylphosphine (37 mg, 0.16 mM) were placed under nitrogen. Tetrahydrofuran (10 mL) was added and the solution was heated at 65° C. for 16 h. Additional tris(dibenzylidineacetone)dipalladium (0) chloroform adduct (42 mg, 0.04 mM) and tri-2-furylphosphine (18 mg, 0.08 mM) were added and the solution was stirred an additional 25 h at 65° C. The solution was cooled, adsorbed directly onto silica gel and chromatographed with neat ethyl acetate to give 870 mg of the desired product.

MS (APCI): 524 (M+1) for $C_{28}H_{37}N_3O_5Si$

NMR (DMSO-$d_6$) δ: 0.06 (s, 3H); 0.08 (s, 3H); 0.85 (s, 9H); 1.86(s,3H); 3.22 (dd, 1H); 3.45-3.47 (m, 3H); 3.73-3.83 (m, 3H); 4.18 (m, 1H); 4.78 (m, 2H); 7.61-7.80 (m, 8H); 8.28 (t, 1H).

The intermediates were prepared as follows:

(5RS)-3-(4-Bromophenyl)-5-({[tert-butyl(dimethyl)silyl]oxy}methyl)-4,5-dihydroisoxazole

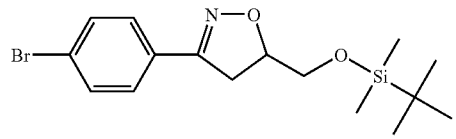

(5RS)-[3-(4-Bromophenyl)-4,5-dihydroisoxazol-5-yl]methanol (6.0 g, 0.023 M, see Pharmacia & Upjohn WO 98-07708), triethyl amine (3.9 mL, 0.028 M), and 4-(dimethylamino)pyridine (0.56 g, 4.58 mM), were combined in dichloromethane (36 mL). A solution of tert-butyldimethylsilyl chloride (1 M in dichloromethane, 26 mL, 0.028 M) was added and the resulting mixture was stirred at room temperature for 16 h. The resulting mixture was poured into water and extracted with dichloromethane. The combined organics were dried (magnesium sulfate), filtered and evaporated. The crude material was purified by chromatography on silica gel using 50% ethyl acetate/hexanes to give 8.4 g of the desired product.

MS (APCI): 371 (M+1) for $C_{10}H_{10}BrNO_2$

NMR (DMSO-d$_6$) δ: 0.04 (s, 3H); 0.06 (s, 3H); 0.83 (s, 9H); 3.18 (m, 1H); 3.39 (m, 1H); 3.72 (m, 2H); 4.80 (m, 1H); 7.60-7.68 (m, 4H).

5-({[tert-butyl(dimethyl)silyl]oxy}methyl)-3-[4-(trimethylstannyl)phenyl]-4,5-dihydroisoxazole For preparation of this compound, see Example 8.

Example 7

N-[((5S,5'RS)-3-{4'-[5-(Hydroxymethyl)4,5-dihydroisoxazol-3-yl]-1,1'-biphenyl-4-yl}-2-oxo-1,3-oxazolidin-5-yl)methyl]acetamide

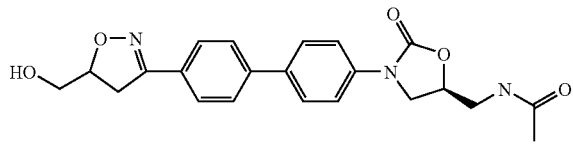

To a solution of N-[((5S,5'RS)-3-{4'-{5-({[tert-butyl(dimethyl)silyl]oxy}methyl)-4,5-dihydroisoxazol-3-yl]-1,1'-biphenyl-4-yl}-2-oxo-1,3-oxazolidin-5-yl)methyl]acetamide (790 mg, 1.51 mM) in tetrahydrofuran (20 ml) was added 1.5 ml of a 1 M tetrabutylammonium fluoride solution in tetrahydrofuran. The solution was stirred at room temperature for 45 min. Water (50 ml) was added and the solid product precipitated. The solids were recrystallized from acetone to give the title product (153 mg).

MS (APCI): 410 (M+1) for C$_{22}$H$_{23}$N$_3$O$_5$

NMR (DMSO-d$_6$) δ: 1.86 (s, 3H); 3.25 (dd, 1H); 3.43-3.49, (m, 3H); 3.53-3.56 (m, 2H); 3.81 (m, 1H); 4.18 (m, 1H); 4.72-4.80 (m, 2H); 5.02, (t, 1H); 7.63-7.85 (m, 8H); 8.27 (t, 1H).

Example 8

Tert-Butyl N-((5R,5'RS)-3-{4'-[5-({[tert-butyl(dimethyl)silyl]oxy}methyl)-4-5-dihydroisoxazol-3-yl]-2-fluoro-1,1'-biphenyl-4-yl}-2-oxo-1,3-oxazolidin-5-yl)methyl N-(isoxazol-3-yl) carbamate

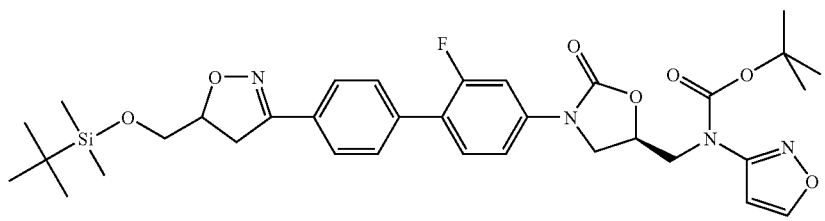

N-(5R)-[3-(3-fluoro-4-iodo-phenyl)-2-oxo-oxazolidin-5-ylmethyl]-N-isoxazol-3-yl carbamic acid tert-butyl ester (580 mg, 1.15 mM), tris(dibenzylidineacetone)dipalladium (0) (48 mg, 0.052 mM) and tri-2-furylphosphine (21 mg, 0.090 mM) were placed in a flask. The solids were degassed and placed under nitrogen. Anhydrous dioxane (6 ml) was added. The resulting purple solution was heated at 100° C. Within minutes, the solution became brown and a solution of 5-({[tert-butyl(dimethyl)silyl]oxy}methyl)-3-[4-(trimethylstannyl)phenyl]-4,5-dihydroisoxazole (733 mg, 1.61 mM) in dioxane (2 ml) was added. The solution was stirred at 100° C. for 16 hours. The reaction mixture was cooled, adsorbed onto silica gel and chromatographed eluting with 20% ethyl acetate/hexanes to give the desired product (636 mg).

MS (APCI): 567 (M+1-100) for C$_{34}$H$_{43}$FN$_4$O$_7$Si—C$_5$H$_9$O$_2$ (BOC group)

NMR (DMSO-d$_6$) δ: 0.07 (s, 3H); 0.08 (s, 3H); 0.85 (s, 9H); 1.52 (s, 9H); 3.23 (dd, 1H); 3.49 (dd, 1H); 3.75 (dq, 2H); 3.94 (dd, 1H); 4.03 (dd, 1H); 4.27-4.34 (m, 2H); 4.81 (m, 1H); 5.07 (m, 1H); 6.89 (br s, 1H); 7.48-7.78 (m, 7H); 8.65 (d, 1H).

The intermediate for this compound was prepared as follows:

(5RS)-5-({[tert-Butyl(dimethyl)silyl]oxy}methyl)-3-[4-(trimethylstannyl)phenyl]-4,5-dihydroisoxazole

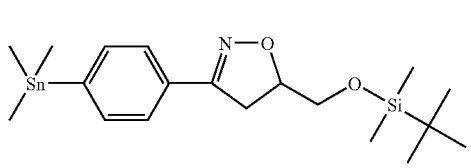

(5RS)-3-(4-Bromophenyl)-5-({[tert-butyl(dimethyl)silyl]oxy}methyl)-4,5-dihydroisoxazole (3.0 g, 8.10 mM) and bis(triphenylphosphine)palladium(II) chloride (285 mg, 0.41 mM) were placed under nitrogen. Anhydrous dioxane (30 ml) was added and the supension was heated to 90° C. Hexamethylditin (3.00 g, 9.16 mM) was added and the resulting solution was stirred at 90° C. for 16 hours. The solution was cooled and the solvent was evaporated. The residue was purified by chromatography on silica gel eluting with hexanes then 5% ethyl acetate/hexanes to give the desired product (3.4 g).

NMR (DMSO-d$_6$) δ: 0.04 (s, 3H); 0.06 (s, 3H); 0.24 (s, 9H); 0.83 (s, 9H); 3.18 (m, 1H); 3.40 (m, 1H); 3.72 (m, 2H); 4.78 (m, 1H); 7.54-7.62 (m, 4H).

Example 9

Tert-Butyl N-((5R,5'RS)-3-[2-fluoro-4'-[5-(hydroxymethyl)-4,5-dihydroisoxazol-3-yl]-1,1'-biphenyl-4-yl}-2-oxo-1,3-oxazolidin-5-yl)methyl N-(isoxazol-3-yl)carbamate

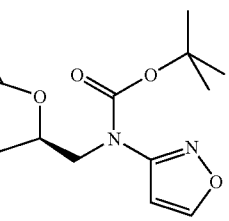

To a solution of tert-butyl N-((5R,5'RS)-3-{4'-[5-({[tert-butyl(dimethyl)silyl]oxy}methyl)-4-5-dihydroisoxazol-3- yl]-2-fluoro-1,1'-biphenyl-4-yl}-2-oxo-1,3-oxazolidin-5-yl) methyl N-(isoxazol-3-yl)carbamate (620 mg, 0.93 mM) in tetrahydrofuran (10 ml) was added a 1 M solution of tetrabutylammonium fluoride in tetrahydrofuran (1.00 ml, 1.00 mM). The solution was stirred at room temperature for 1 hour. Water (approximately. 50 ml) was added and the mixture was extracted with ethyl acetate. The organic phase was washed with brine, dried (magnesium sulfate) and evaporated. The residue was purified by chromatography on silica gel using 75% ethyl acetate/hexanes to give the desired product as a white solid (477 mg).

MS (APCI): 553 (M+1) for $C_{28}H_{29}FN_4O_7$

NMR (DMSO-$d_6$) δ: 1.52 (s, 9H); 4.99 (dd, 1H); 3.46 (dd, 1H); 3.54-3.57 (m, 2H); 3.94 (dd, 1H); 4.03 (dd, 1H); 4.27-4.34 (m, 2H); 4.76 (m, 1H); 5.01-5.08 (m, 2H); 6.90 (br s, 1H); 7.48-7.79 (m, 7H); 8.85 (d, 1H).

Example 10

(5S,5'RS)-3-{2-Fluoro-4'-[5-hydroxymethyl)-4,5-dihydroisoxazol-3-yl]-1,1'-biphenyl-4-yl}-5-[(isoxazol-3-ylamino)methyl]-1,3-oxazolidin-2-one

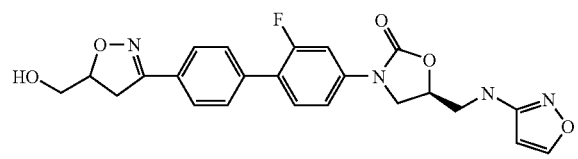

To a solution of tert-butyl N-((5R,5'RS)-3-{2-fluoro-4'-[5-(hydroxymethyl)-4,5-dihydroisoxazol-3-yl]-1,1'-biphenyl-4-yl}-2-oxo-1,3-oxazolidin-5-yl)methyl N-(isoxazol-3-yl) carbamate (474 mg, 0.86 mM) in dichloromethane (10 ml) was added trifluoroacetic acid (5 mL) and the solution was stirred at room temperature for two hours. The solvent was evaporated, and the residue was purified by chromatography on silica gel using 75% ethyl acetate/hexanes to 100% ethyl acetate to give the desired product 227 mg.

MS (APCI): 453 (M+1) for $C_{23}H_{21}FN_4O_5$

NMR (DMSO-$d_6$) δ: 3.25 (dd, 1H); 3.43-3.55 (m, 5H); 3.89 (dd, 1H); 4.24 (t, 1H); 4.76 (m, 1H); 4.92-5.02 (m, 2H); 6.03 (d, 1H); 6.59 (t, 1H); 7.46-7.78 (m, 7H); 8.42 (d, 1H).

Example 11

(5R,5'R)-4,4'-Bis-(5-(1H-1,2,3-triazol-1-yl)methyl-2-oxo-oxazolidin-3-yl)-2,2'-difluoro-biphenyl

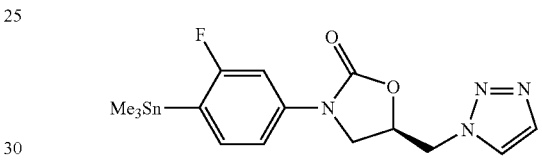

A stirred mixture of (5R)-3-(3-fluoro-4-(trimethylstannyl) phenyl)-5-(1H-1,2,3-triazol-1-ylmethyl)-1,3-oxazolidin-2-one (425 mg, 1.0 mmol), 2-bromo-5-cyano-thiazole (189 mg, 1.0 mmol), and copper(I) iodide in dimethylformamide (5 ml) was purged with a slow stream of nitrogen for 20 min and then tetrakis(triphenylphosphine)palladium(0) (58 mg, 0.05 mmol) was added. The stirred reaction mixture was maintained at 70° C. under an atmosphere of nitrogen for 5 hours. The stirred reaction mixture was treated with aqueous potassium fluoride (10%, 20 ml) and then stirred for 30 min, treated with ethyl acetate (20 ml). The precipitate was isolated by filtration to give fraction A of impure product. The organic phase was separated, dried (MgSO$_4$), treated with silica-gel (500 mg), and evaporated under reduced pressure to leave a free-running solid. The solid was applied to a silica-gel column and eluted with dichloromethane-methanol (0%-10% methanol gradient) to give a further fraction B of impure product. Fractions A and B were dissolved in DMSO (6 ml total), combined, and purified by reverse phase hplc to give the desired product (18 mg).

MS (ESP): 523 (MH$^+$) for $C_{24}H_{20}F_2N_8O_4$ $^1$H NMR (DMSO-$d_6$) δ: 3.95 (dd, 2H); 4.26 (t, 2H); 4.86 (d, 4H); 5.18 (m, 2H); 7.39 (d, 2H); 7.47 (m, 2H); 7.53 (m, 2H); 7.78 (s, 2H); 8.19 (s, 2H).

The intermediate for this compound was prepared as follows:

(5R)-3-[3-Fluoro-4-(trimethylstannyl)phenyl]-5-(1H-1,2,3-triazol-1-ylmethyl)-1,3-oxazolidin-2-one A mixture of (5R)-3-(3-fluoro-4-iodophenyl)-5-(1H-1,2,3-triazol-1-ylmethyl)-1,3-oxazolidin-2-one (5.39 g, 13.9 mmol) and hexamethylditin (5 g, 15.3 mmol) in dioxane (50 ml) under an atmosphere of nitrogen was treated with dichlorobis(triphenylphoshine)palladium (II) (487 mg, 0.69 mmol) and then stirred at 90° C. under an atmosphere of nitrogen for 90 minutes. Silica gel (5 g) was added then the solvent removed under reduced pressure. The residual powder was placed on top of a silica gel column (100 g) and eluted (1% methanol in dichloromethane to 2.5% methanol in dichloromethane gradient) to give the desired product (4.545 g).

MS (ESP) 423, 425, 427 (MH+) for $C_{15}H_{19}FN_4O_2Sn$.

$^1$H-NMR (DMSO-$d_6$) δ: 0.32 (s, 9H); 3.90 (dd, 1H); 4.25 (t, 1H); 4.85 (d, 2H); 5.16 (m, 1H); 7.26 (dd, 1H); 7.33 (dd, 1H); 7.41 (dd, 1H); 7.78 (s, 1H); 8.18 (s, 1H).

Example 12

(5R)-3-{2-Fluoro-4'-[5-(hydroxymethyl)-4,5-dihydroisoxazol-3-yl]-1,1'-biphenyl-4-yl}-5-[(4-methyl-1H-1,2,3-triazol-1-yl)methyl]-1,3-oxazolidin-2-one

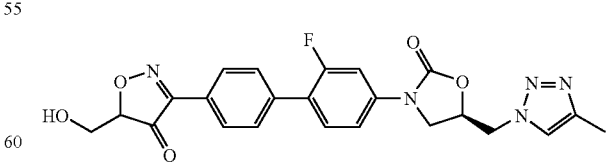

(5R)-3-{4'-[5-({[tert-Butyl(dimethyl)silyl]oxy}methyl)-4,5-dihydroisoxazol-3-yl]-2-fluoro-1,1'-biphenyl-4-yl}-5-[(4-methyl-1H-1,2,3-triazol-1-yl)methyl]-1,3-oxazolidin-2-one (283 mg, 0.5 mmol) was dissolved in tetrahydrofuran (5 ml) at room temperature. A 1M solution of tetrabutylammonium fluoride in tetrahydrofuran (0.5 ml, 0.5 mmol) was added and the reaction mixture stirred for 30 minutes. The solvent was removed in vacuo then dichloromethane (50 ml) added. This was washed with water (50 ml), separated, dried (magnesium sulfate), filtered then concentrated in vacuo onto silica (2 ml). This was then subjected to chromatography (silica gel 10 g bond elut; 0 to 6% methanol/dichloromethane) to yield 150 mg (66%) of the desired compound.

MS (ESP+): (M+H)+452.28 for $C_{23}H_{22}FN_5O_4$

NMR (DMSO-$d_6$) δ: 2.25 (s, 3H); 3.25 (dd, 1H); 3.46 (dd, 1H); 3.54 (m, 2H); 3.95 (dd, 1H); 4.30 (t, 1H); 4.76 (m, 1H); 4.79 (d, 2H); 5.03 (t, 1H); 5.17 (m, 1H); 7.42 (dd, 1H); 7.58 (dd, 1H); 7.62 to 7.66 (m, 3H); 7.77 (d, 2H); 7.90 (s, 1H). (dd, 1H); 7.58 (dd, 1H); 7.62 to 7.66 (m, 3H); 7.77 (d, 2H); 7.90 (s, 1 H).

3-(4-Bromophenyl)-5-({[tert-butyl(dimethyl)silyl] oxy}methyl)-4,5-dihydroisoxazole

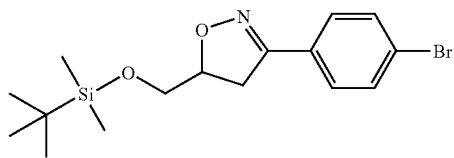

[3-(4-Bromophenyl)-4,5-dihydroisoxazol-5-yl]methanol (4.44 g, 17 mmol) was dissolved in a mixture of triethylamine (2.9 ml, 19 mmol) and dichloromethane (100 ml). The resulting solution was cooled to 0° C., then a 1 M solution of tert-butyldimethylsilylchloride (19 ml) in dichloromethane was added dropwise over 5 minutes. 4-Dimethylamino pyridine (0.423 g, 3.4 mmol) was added and the reaction mixture left to stir overnight at room temperature. A second portion of tert-butyldimethylsilylchloride (19 ml) in dichloromethane and triethylamine (2.9 ml, 19 mmol) were added and the reaction mixture left to stir overnight at room temperature. The reaction mixture was concentrated in vacuo then redissolved in dichloromethane (200 ml) and washed with water (200 ml). The dichloromethane layer was separated, dried over magnesium sulfate, filtered and concentrated in vacuo onto silica gel (5 ml). This was then subjected to column chromatography (50 g silica gel bond elut: 0% to 50% ethyl acetate/hexanes) to yield 5.405 g (84%) of the desired compound as white crystals.

MS (APCI): (M+H)+370 & 372 for $C_{16}H_{24}BrNO_2Si$

NMR (DMSO-$d_6$) δ: 0.00 (s, 3H); 0.02 (s, 3H); 0.78 (s, 9H); 3.13 (dd, 1H); 3.39 (dd, 1H); 3.64 (m, 1H); 3.66 (dd, 1H); 4.75 (m, 1H); 7.59 (dd, 4H). 1H); 3.64 (m, 1H); 3.66 (dd, 1H); 4.75 (m, 1H); 7.59 (dd, 4 H).

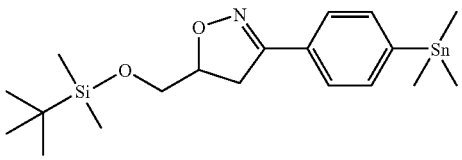

3-(4-Bromophenyl)-5-({[tert-butyl(dimethyl)silyl] oxy}methyl)-4,5-dihydroisoxazole (5.403 g, 14.6 mmol) was dissolved in dry 1,4-dioxane (50 ml). The solution was placed under an atmosphere of argon. Hexamethylditin (5.26 g, 16 mmol) was added followed by bis(triphenylphosphine)palladium(II) chloride (0.512 g, 0.73 mmol). The reaction mixture was stirred at 90° C. for 90 minutes under an atmosphere of argon. The solvent was removed in vacuo and then the crude product re-dissolved in ethyl acetate (100 ml). Silica gel (5 ml) was added and the mixture concentrated in vacuo. This was then subjected to column chromatography (50 g silica gel bond elut: 0% to 50% ethyl acetate/hexanes) to yield 4.893 g (74%) of the desired compound as a colourless oil.

MS (APCI): (M+H)+452.23, 453.24, 454.24, 455.24, 456.24, 457.24, 458.24 & 460.25 for $C_{13}H_{33}NO_2SiSn$ NMR (DMSO-$d_6$) δ: 0.05 (s, 3H); 0.07 (s, 3H); 0.30 (s, 9H); 0.84 (s, 9H); 3.17 (dd, 1H); 3.39 (dd, 1H); 3.60 to 3.77 (m, 2H); 4.76 (m, 1H); 7.59 (dd, 4H). 1H); 3.39 (dd, 1H); 3.60 to 3.77 (m, 2H); 4.76 (m, 1H); 7.59 (dd, 4 H). -2-fluoro-1,1'-biphenyl-4-yl}-5-[(4-methyl-1H-1,2,3-triazol-1-yl)methyl-1,3-oxazolidin-2-one

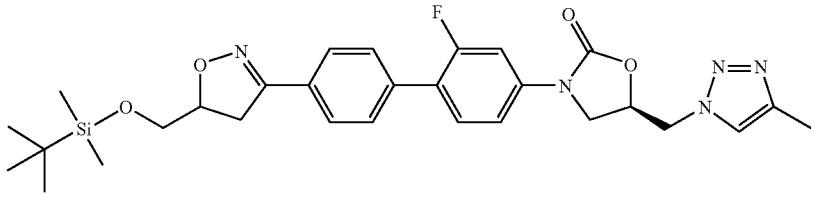

5-({[tert-Butyl(dimethyl)silyl]oxy}methyl)-3-[4-(trimethylstannyl)phenyl]-4,5-dihydroisoxazole (436 mg, 0.96 mmol), (5R)-3-(3-fluoro-4-iodophenyl)-5-[(4-methyl-1H-1,2,3-triazol-1-yl)methyl]-1,3-oxazolidin-2-one (386 mg, 0.96 mmol) and 2-trifurylphosphine (22 mg, 0.096 mmol) were dissolved in dry 1,4-dioxane (10 ml) and the reaction mixture placed under an atmosphere of argon. Tris(dibenzylidineacetone)dipalladium (0) chloroform adduct (50 mg, 0.05 mmol) was added and the reaction mixture stirred for 16 hours at 90° C. A second portion of 5-({[tert-butyl(dimethyl)silyl] oxy}methyl)-3-[4-(trimethylstannyl)phenyl]-4,5-dihydroisoxazole (436 mg, 0.96 mmol), 2-trifurylphosphine (22 mg, 0.096 mmol) and tris(dibenzylidineacetone)dipalladium (0) chloroform adduct (50 mg, 0.05 mmol) were added and the reaction mixture stirred for another 20 hours at 90° C. Silica gel (2 g) was added and the mixture concentrated in vacuo. This was purified by column chromatography (20 g silica gel bond elut: 30% to 100% ethyl acetate/hexanes) to yield 283 mg (52%) of the desired compound.

MS (ESP+): (M+H)+566.39 for $C_{29}H_{36}FN_5O_4Si$

NMR (DMSO-$d_6$) δ: 0.06 (s, 3H); 0.08 (s, 3H); 0.85 (s, 9H); 2.25 (s, 3H); 3.23 (dd, 1H); 3.48 (dd, 1H); 3.70 to 3.80

(m, 2H); 3.95 (dd, 1H); 4.30 (t, 1H); 5.05 (m, 3H); 5.16 (m, 1H); 7.42 (dd, 1H); 7.58 (dd, 1H); 7.62 to 7.66 (m, 3H); 7.77 (d, 2H); 7.90 (s, 1H). (s, 1 H).

N-[((5S)-3-{2-Fluoro-4'-[5-(hydroxymethyl)-4,5-dihydroisoxazol-3-yl]-1,1'-biphenyl-4-yl}-2-oxo-1,3-oxazolidin-5-yl)methyl]acetamide

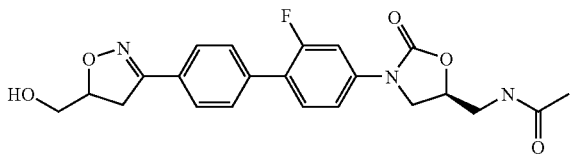

N-[((5S)-3-{4'-[5-({[tert-Butyl(dimethyl)silyl]oxy}methyl)-4,5-dihydroisoxazol-3-yl]-2-fluoro-1,1'-biphenyl-4-yl}-2-oxo-1,3-oxazolidin-5-yl)methyl]acetamide (164 mg, 0.3 mmol) was dissolved in tetrahydrofuran (5 ml) at room temperature. A solution of tetrabutylammonium fluoride in tetrahydrofuran (1M; 0.3 ml, 0.3 mmol) was added and the reaction mixture stirred for 30 minutes. The solvent was removed in vacuo then dichloromethane (2 ml) added. Purification by chromatography (SiO$_2$ 10 g bond elut; 0 to 6% methanol/dichloromethane) yielded a white solid. This was washed with water (50 ml) to yield 37.9 mg (29%) of the desired compound.

MS (ESP+): (M+H)$^+$ 428.24 for $C_{22}H_{22}FN_3O_5$

NMR (DMSO-d$_6$) δ: 1.86 (s, 3H); 3.26 (dd, 1H); 3.46 (m, 3H); 3.54 (m, 2H); 3.81 (dd, 1H); 4.20 (t, 1H); 4.78 (m, 2H); 5.03 (t, 1H); 7.45 (dd, 1H); 7.62 to 7.68 (m, 4H); 7.77 (d, 2H); 8.28 (t, 1H). 7.77 (d, 2H); 8.28 (t, 1 H).

N-[((5S)-3-{4'-[5-({[tert-Butyl(dimethyl)silyl]oxy}methyl)-4,5-dihydroisoxazol-3-yl]-2-fluoro-1,1'-biphenyl-4-yl}-2-oxo-1,3-oxazolidin-5-yl)methyl]acetamide

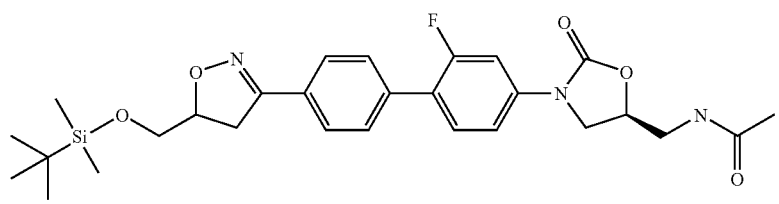

5-({[tert-Butyl(dimethyl)silyl]oxy}methyl)-3-[4-(trimethylstannyl)phenyl]4,5-dihydroisoxazole (427 mg, 0.94 mmol), N-{[(5S)-3-{3-fluoro-4-iodophenyl)-2-oxo-1,3-oxazolidin-5-yl]methyl}acetamide (355 mg, 0.96 mmol) and 2-trifurylphosphine (22 mg, 0.094 mmol) were dissolved in dry 1,4-dioxane (10 ml) and the reaction mixture placed under an atmosphere of argon. Tris(dibenzylidineacetone)dipalladium (0) chloroform adduct (49 mg, 0.05 mmol) was added and the reaction mixture stirred for 16 hours at 90° C. A second portion of 5-({[tert-butyl(dimethyl)silyl]oxy}methyl)-3-[4-(trimethylstannyl)phenyl]-4,5-dihydroisoxazole (427 mg, 0.94 mmol), 2-trifurylphosphine (22 mg, 0.094 mmol) and tris(dibenzylidineacetone)dipalladium (0) chloroform adduct (49 mg, 0.05 mmol) were added and the reaction mixture stirred for another 20 hours at 90° C. Silica gel (2 g) was added and the mixture concentrated in vacuo. Purification by column chromatography (20 g silica gel bond elut: 30% to 100% ethyl acetate/hexanes) yielded 170 mg (33%) of the desired compound.

MS (ESP+): (M+H)$^+$ 542.42 for $C_{28}H_{36}FN_3O_5Si$

NMR (DMSO-d$_6$) δ: 0.06 (s, 3H); 0.08 (s, 3H); 0.85 (s, 9H); 1.86 (s, 3H); 3.23 (dd, 1H); 3.46 (m, 2H); 3.49 (dd,1H); 3.70 to 3.83 (m, 3H); 4.20 (t, 1H); 4.80 (m, 2H); 7.45 (dd, 1H); 7.62 to 7.66 (m, 4H); 7.77 (d, 2H); 8.28 (t, 1H). 7.45 (dd, 1H); 7.62 to 7.66 (m, 4H); 7.77 (d, 2H); 8.28 (t, 1 H).

Example 14

N-[(3-{2-Fluoro-4'-[(5R)-5-(hydroxymethyl)-2-oxo-1,3-oxazolidin-3-yl]-1,1'-biphenyl-4-yl}-4,5-dihydroisoxazol-5-yl)methyl]acetamide

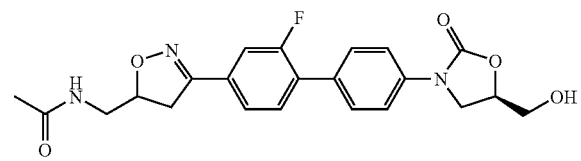

N-({3-[3-Fluoro-4-(trimethylstannyl)phenyl]-4,5-dihydroisoxazol-5-yl]methyl}acetamide (600 mg, 1.5 mmol), (5S)-5-(hydroxymethyl)-3-(4-iodophenyl)-1,3-oxazolidin-2-one (319 mg, 1.0 mmol) and 2-trifurylphosphine (23 mg, 0.1 mmol) were dissolved in dry 1,4-dioxane (10 ml) and the reaction mixture placed under an atmosphere of argon. Tris(dibenzylidineacetone)dipalladium (0) chloroform adduct (52 mg, 0.05 mmol) was added and the reaction mixture stirred for 16 hours at 90° C. Silica gel (0.5 g) was added and the mixture concentrated in vacuo. Purification by column chromatography (10 g silica gel bond elut: 0% to 5% methanoydichloromethane) yielded an off white solid. This was dissolved in dimethylsulphoxide (0.5 ml) and purified by reverse phase preparative HPLC using a gradient from 20% acetonitrile/water to 70% acetonitrile/water to give 3.7 mg of the desired compound.

MS (ESP+): (M+H)$^+$428.31 for $C_{22}H_{22}FN_3O_5$

NMR (DMSO-d$_6$) δ: 1.83 (s, 3H); 3.16 (dd, 1H); 3.28 (t, 2H); 3.49 (dd, 1H); 3.58 (dd, 1H); 3.70 (dd, 1H); 3.89 (q, 1H);

4.14 (t, 1H); 4.73 (m, 1H); 4.79 (m, 1H); 5.23 (br s, 1H); 7.53 to 7.59 (m, 2H); 7.61 to 7.67 (m, 3H); 7.70 to 7.73 (d, 2H); 8.15 (t, 18.15 (t, 1

The following examples were prepared by a similar procedure to Example 14 above:

Example 15

N-[(3-{2,2'-Difluoro-4'-{(5R)-5[(4-methyl-1H-1,2,3-triazol-1-yl)methyl]}-2-oxo-1,3-oxazolidin-3-yl]-1,1'-biphenyl-4-yl]-4,5-dihydroisoxazol-5-yl)methyl]acetamide

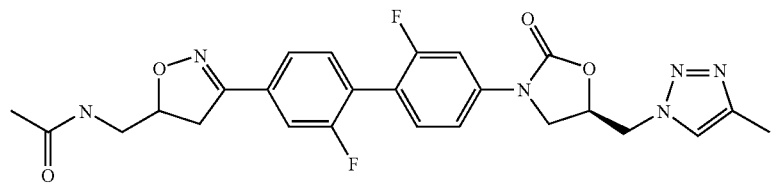

Yield=51 mg.

MS (APCI): (M+H)$^+$511.2 for $C_{25}H_{24}F_2N_6O_4$

NMR (DMSO-d$_6$) δ: 1.83 (s, 3H); 2.23 (s, 3H); 3.17 (dd, 1H); 3.29 (t, 2H); 3.50 (dd, 1H); 3.94 (q, 1H); 4.29 (t, 1H); 4.77 (d, 2H); 4.79 (m, 1H); 5.14 (m, 1H); 7.42 (dd, 1H); 7.50 to 7.62 (m, 5H); 7.89 (s, 1H); 8.15 (t, 1H).

Example 16

N-[(3-{2,2'-Difluoro-4'-{(5R,S)-5-acetamidomethyl-4,5-dihydroisoxazol-5-yl]-1,1'-biphenyl-4-yl}-4,5-dihydroisoxazol-5-yl)methyl]acetamide

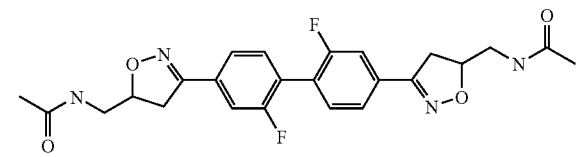

Yield=10 mg.

MS (APCI): (M+H)$^+$ 471.2 for $C_{24}H_{24}F_2N_4O_4$

NMR (DMSO-d$_6$) δ: 1.83 (s, 6H); 3.17 (dd, 2H); 3.29 (t, 4H); 3.50 (dd, 2H); 4.80 (m, 2H); 7.55 to 7.65 (m, 6H); 8.16 (t, 2H).

The intermediates for these compounds were prepared as follows.

[3-(4-Bromo-3-fluorophenyl)-4,5-dihydroisoxazol-5-yl]methane sulfonate

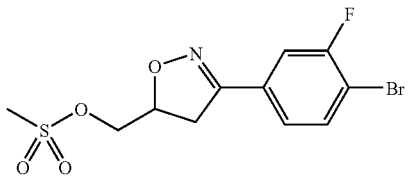

[3-(4-Bromo-3-fluorophenyl)-4,5-dihydroisoxazol-5-yl]methanol (7.668 g, 28 mmol) was dissolved in a mixture of triethylamine (4.68 ml, 35 mmol) and dichloromethane (100 ml). The resulting solution was cooled to 0° C. then methane sulfonyl chloride (2.38 ml, 31 mmol) was added. The reaction mixture was stirred at 0° C. for 20 minutes then allowed to warm to room temperature. Water (100 ml) was added and then the organic layer separated, dried over magnesium sulfate, filtered, then concentrated in vacuo to yield 9.85 g of the desired compound.

MS (APCI): (M+H)$^+$ 352.08 & 354.08 for $C_{11}H_{11}BrFNO_4S$ 5-(Azidomethyl)-3-(4-bromo-3-fluorophenyl)-4,5-dihydroisoxazole

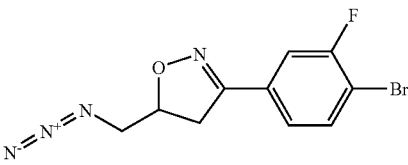

[3-(4-Bromo-3-fluorophenyl)-4,5-dihydroisoxazol-5-yl]methane sulfonate (9.85 g, 28 mmol) was dissolved in dry DMF (100 ml). Sodium azide (2.73 g, 42 mmol) was added and the reaction mixture stirred at 80° C. for 5 hours. The reaction mixture was concentrated in vacuo then azeotroped with xylene (20 ml). The crude product was dissolved in ethyl acetate (100 ml) and washed with water (100 ml). The organic layer was separated, dried over magnesium sulfate, filtered then concentrated in vacuo to yield 8.046 g of the desired compound.

MS (APCI): (M+H)$^+$ 299.0 & 301.0 for $C_{10}H_8BrFN_4O$

NMR (CDCl$_3$) δ: 3.09 to 3.14 (dd, 1H); 3.31 to 3.41 (m, 2H); 3.49 to 3.52 (dd, 1 H); 4.88 (m, 1 H); 7.26 (dd, 1H); 7.38 (dd, 1H); 7.53 (dd, 1 H).

NMR (DMSO-d$_6$) δ: 3.23 (dd,1H0; 3.49 to 3.46 (m, 3H); 4.98 (m, 1H); 7.49 (dd, 1H); 7.67 (dd, 1H); 7.83 (dd, 1 H).

61

[3-(4-Bromo-3-fluorophenyl)-4,5-dihydroisoxazol-5-yl]methylamine

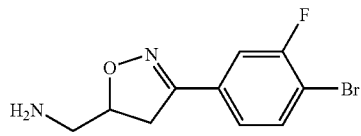

5-(Azidomethyl)-3-(4-bromo-3-fluorophenyl)-4,5-dihydroisoxazole (8.046 g, 26.9 mmol) was dissolved in a mixture of acetonitrile (40 ml) and water (4 ml). Triphenylphosphine (8.48 g, 32.3 mmol) was added and the reaction mixture stirred at room temperature for 48 hours. The reaction mixture was then poured onto a silica gel chromatography column (400 ml). The product was eluted with 10% to 20% water/acetonitrile, then freeze dried to yield 2.67 g of the desired compound.

MS (APCI): (M+H)$^+$ 273.0 & 275.0 for $C_{10}H_{10}BrFN_2O$

NMR (DMSO-$d_6$) δ: 2.73 (m, 2H); 3.26 (dd, 1H); 3.41 (dd, 1H); 3.25 to 3.50 (br s, 2H); 4.72 (m, 1H); 7.45 (dd, 1H); 7.58 (dd, 1H); 7.78 (t, 1 H).

N-{[3-(Bromo-3-fluorophenyl)-4,5-dihydroisoxazol-5-yl]methyl}acetamide

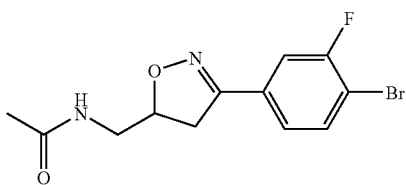

[3-(4-Bbromo-3-fluorophenyl)-4,5-dihydroisoxazol-5-yl]methylamine (1.583 g, 5.8 mmol) was dissolved in a mixture of pyridine (4.7 ml, 58 mmol) and dichloromethane (50 ml). Acetic anhydride (2.74 ml, 29 mmol) was added and the reaction mixture stirred at room temperature for 16 hours under an atmosphere of nitrogen. Water (100 ml) was added and then the organic layer separated, dried over magnesium sulfate, filtered then concentrated in vacuo onto silica gel (1 g). This was subjected to column chromatography (silica gel bond elut; 40% to 100% ethyl acetate/hexanes) to yield 1.303 g of the desired compound.

MS (APCI): (M+H)$^+$ 315.0 & 317.0 for $C_{12}H_{12}BrFN_2O_2$

NMR (DMSO-$d_6$) δ: 1.83 (s, 3H); 3.14 (dd, 1H); 3.28 (t, 2H); 3.47 (dd, 1H); 4.79 (m, 1H); 7.46 (dd, 1H); 7.63 (dd, 1H); 7.83 (t,1H)); 8.16 (t, 1 H).

62

N-({3-[3-Fluoro-4-(trimethylstannyl)phenyl]-4,5-dihydroisoxazol-5-yl}methyl}acetamide

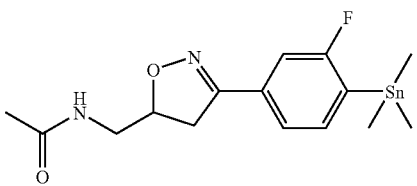

N-{[3-(Bromo-3-fluorophenyl)-4,5-dihydroisoxazol-5-yl]methyl}acetamide (1.303 g, 4.13 mmol) was dissolved in dry 1,4-dioxane (20 ml). The solution was placed under an atmosphere of argon. Hexamethylditin (1.49 g, 4.55 mmol) was added followed by bis(triphenylphosphine)palladium(II) chloride (0.216 g, 0.31 mmol). The reaction mixture was stirred at 90° C. for 4 hours under an atmosphere of argon. The solvent was removed in vacuo, then the crude product re-dissolved in ethyl acetate (100 ml). Silica gel (5 ml) was added and the mixture concentrated in vacuo. This was then subjected to column chromatography (20 g silica gel bond elut: 0% to 100% ethyl acetate/hexanes) to yield 1.201 g (73%) of the desired compound as a white solid.

MS (APCI): (M+H)$^+$ 397.21, 398.21, 399.21, 400.21, 401.15, 402.15 & 403.15 for $C_{15}H_{21}FN_2O_2Sn$ NMR (DMSO-$d_6$) δ: 0.36 (s, 9H); 1.83 (s, 3H); 3.13 (dd, 1H); 3.28 (t, 2H); 3.45 (dd, 1H); 4.76 (m, 1H); 7.36 (dd, 1H); 7.77 (br d, 1H); 7.53 (dd, 1H)); 8.15 (t, 1 H).

Example 17

N-{[(5S)-(2,2'-Difluoro-4'-{5-[4-methyl-1H-1,2,3-triazol-1-yl)methyl]-4,5-dihydroisoxazol-3-yl}-1,1'-biphenyl-4-yl)-2-oxo-1,3-oxazolidin-5-yl]methyl}acetamide 1-({3-[3-Fluoro-4-(trimethylstannyl)phenyl]-4,5-dihydroisoxazol-5-yl}methyl)-4-methyl-1H-1,2,3-triazole (427 mg, 1.0 mmol), N-{[(5S)-3-(3-fluoro-4-iodophenyl)-2-oxo-1,3-oxazolidin-5-yl]methyl}acetamide (254 mg, 0.67 mmol) and 2-trifurylphosphine (16 mg, 0.067 mmol) were dissolved in dry 1,4-dioxane (10 ml) and the reaction mixture placed under an atmosphere of argon. Tris(dibenzylidineacetone)

dipalladium (0) chloroform adduct (35 mg, 0.033 mmol) was added and the reaction mixture stirred for 16 hours at 90° C. under an atmosphere of argon. The reaction mixture was subjected to column chromatography (20 g silica gel bond elut; 0% to 50% methanol/dichloromethane) to yield 19 mg (5%) of the desired compound.

MS (ESP+): (M+H)$^+$ 511.30 for $C_{25}H_{24}F_2N_6O_4$

NMR (DMSO-d) δ: 1.86 (s, 3H); 2.24 (s, 3H); 3.32 (m, 1H); 3.46 (m, 2H); 3.64 (dd, 1H); 3.81 (dd, 1H); 4.20 (t, 1H); 4.60 (m, 2H); 4.79 (m, 1H); 5.19 (m, 1H); 7.47 to 7.66 (m, 6H); 7.88 (s, 1H); 8.28 (t, 1 H).

The following example was prepared by a similar procedure to Example 17 above:

Example 18

1-([3-{2,2'-Difluoro-4'-[(5R,S)-5-(4-methyl-1H-1,2,3-triazol-1-ylmethyl)-4,5-dihydroisoxazol-3-yl]-1,1'-biphenyl-4-yl}-4,5-dihydroisoxazol-5-yl]methyl)-4-methyl-1H-1,2,3-triazole

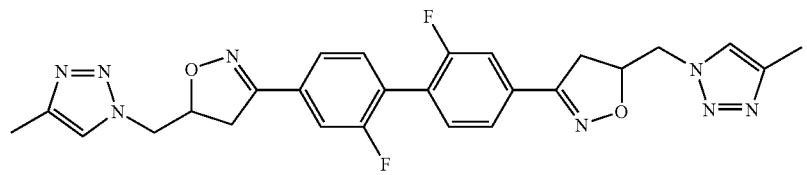

Yield=49 mg

MS (ESP+): (M+H)$^+$ 519.32 for $C_{26}H_{24}F_2N_8O_2$

NMR (DMSO-d$_6$) δ: 2.25 (s, 6H); 3.33 (m, 2H); 3.63 (dd, 2H); 4.61 (m, 4H); 5.19 (m, 2H); 7.62 (m, 6H); 7.88 (s, 2H).

The intermediates for this compound were prepared as follows.

1-{[3-(4-Bromo-3-fluorophenyl)-4,5-dihydroisoxazol-5-yl]methyl}-4-methyl-1H-1,2,3-triazole

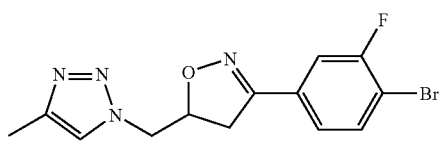

[3-(4-Bromo-3-fluorophenyl)-4,5-dihydroisoxazol-5-yl]methylamine (0.856 g, 3.1 mmol) was dissolved in a mixture of diisopropylethylamine (2.18 ml, 12.5 mmol) and dry methanol (10 ml). N'-[2,2-Dichloro-1-methylethylidene]-4-methylbenzenesulfonylhydrazide (1.16 g, 3.1 mmol) was added and the reaction mixture stirred for 16 hours under an atmosphere of nitrogen. Silica gel (4 ml) was added and the mixture concentrated in vacuo. This was then purified by column chromatography (20 g silica gel bond elut: 60% to 100% ethyl acetate/hexanes) to yield 0.834 g (78%) of the desired compound as a white solid.

MS (APCI): (M+H)$^+$ 339.0 & 341.0 for $C_{13}H_{12}BrFN_4O$

NMR (DMSO-d$_6$) δ: 2.22 (s, 3H); 3.27 (dd, 1H); 3.58 (dd, 1H); 4.57 (m, 2H); 5.16 (m, 1H); 7.45 (dd, 1H); 7.62 (dd, 1H); 7.82 (t, 1 H); 7.86 (s, 1 H).

1-({3-[3-Fluoro-4-(trimethylstannyl)phenyl]-4,5-dihydroisoxazol-5-yl}methyl)-4-methyl-1H-1,2,3-triazole

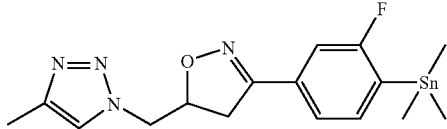

1-{[3-(4-Bromo-3-fluorophenyl)-4,5-dihydroisoxazol-5-yl]methyl}4-methyl-1H-1,2,3-triazole (1.33 g, 3.9 mmol) was dissolved in dry 1,4-dioxane (20 ml). The solution was placed under an atmosphere of argon. Hexamethylditin (1.41 g, 4.3 mmol) was added followed by bis(triphenylphosphine)palladium(II) chloride (0.138 g, 0.2 mmol). The reaction mixture was stirred at 90° C. for 3 hours under an atmosphere of argon. The solvent was removed in vacuo, then the crude product re-dissolved in ethyl acetate (100 ml). Silica gel (5 ml) was added and the mixture concentrated in vacuo. This was purified by column chromatography (20 g silica gel bond elut: 50% to 100% ethyl acetate/hexanes) to yield 0.855 g (52%) of the desired compound as a white solid.

MS (APCI): (M+H)$^+$ 421.34, 422.34, 423.34, 424.34, 425.34 & 426.44 for $C_{16}H_{21}FN_4OSn$ NMR (DMSO-d$_6$) δ: 0.36 (s, 9H); 2.23 (s, 3H); 3.27 (dd, 1H); 3.58 (dd, 1H); 4.58 (m, 2H); 5.14 (m, 1H); 7.34 (q, 1H); 7.45 (d, 1H); 7.52 (dd, 1H); 7.86 (s, 1H).

Example 19

N-[((5S)-3-{2,2'-Difluoro-4'-[5-(hydroxymethyl)-4,5-dihydroisoxazol-3-yl]-1,1'-biphenyl-4-yl}-2-oxo-1,3-oxazolidin-5-yl)methyl]acetamide

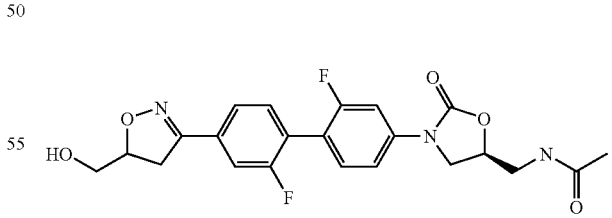

N-[((5S)-3-{4'-[5-({[tert-Butyl(dimethyl)silyl]oxy}methyl)-4,5-dihydroisoxazol-3-yl]-2,2'-difluoro-1,1'-biphenyl-4-yl}-2-oxo-1,3-oxazolidin-5-yl)methyl]acetamide (416 mg, 0.74 mmol) was dissolved in dichloromethane (25 ml) at room temperature. A 1M solution of tetrabutylammonium fluoride in tetrahydrofuran (0.82 ml, 0.82 mmol) was added and the reaction mixture stirred for 300 minutes. Water (50 ml) was added and the dichloromethane layer separated, dried over magnesium sulfate, filtered then concentrated in vacuo onto silica (2 ml). This was purified by chromatography (20 g silica gel bond elut; 0 to 6% methanol/dichloromethane) to yield 125 mg (38%) of the desired compound.

MS (ESP+): (M+H)+ 446.27 for $C_{22}H_{21}F_2N_3O_5$

NMR (DMSO-$d_6$) δ: 1.86 (s, 3H); 3.23 (dd, 1H); 3.45 (m, 3H); 3.51 to 3.59 (m, 2H); 3.81 (q, 1H); 4.20 (t, 1H); 4.76 to 4.81 (m, 2H); 5.04 (t, 1H); 7.47 (dd, 1H); 7.53 to 7.58 (dd, 2H); 7.59 to 7.66 (m, 3H); 8.28 (t, 1H).

The following Examples were prepared by a similar procedure to Example 19 above.

Example 20

(5R)-3-{2,2'-Difluoro-4'-[5-(hydroxymethyl)4,5-dihydroisoxazol-3-yl]-1,1'-biphenyl-4-yl}-5-[(4-methyl-1H-1,2,3-triazol-1-yl)methyl]-1,3-oxazolidin-2-one

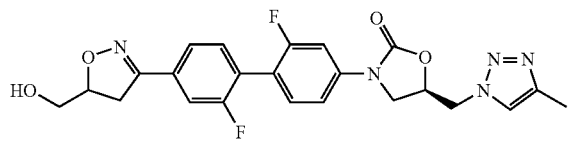

Yield=29 mg (7%)

MS (ESP+): (M+H)+ 470.31 for $C_{23}H_{21}F_2N_5O_4$

NMR (DMSO-$d_6$) δ: 2.25 (s, 3H); 3.25 (dd, 1H); 3.45 (dd, 1H); 3.51 to 3.59 (m, 2H); 3.95 (q, 1H); 4.31 (t, 1H); 4.76 to 4.82 (m, 3H); 5.04 (t, 1H); 5.16 (m, 1H); 7.44 (dd, 1H); 7.52 to 7.64 (m, 5H); 7.91 (s, 1H).

Example 21

(5R)-3-{2,2'-Difluoro-4'-[5-(hydroxymethyl)-4,5-dihydroisoxazol-3-yl]-1,1'-biphenyl-4-yl}-5-(1H-1,2,3-triazol-1-ylmethyl)-1,3-oxazolidin-2-one

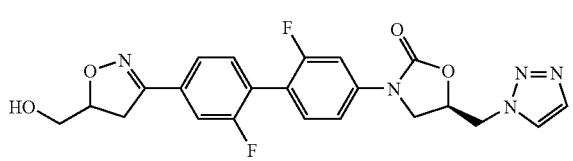

Yield=137 mg (48%)

MS (ESP+): (M+H)+ 456.28 for $C_{22}H_{19}F_2N_5O_4$

NMR (DMSO-$d_6$) δ: 3.25 (dd, 1H); 3.46 (dd, 1H); 3.51 to 3.59 (m, 2H); 3.98 (q, 1H); 4.32 (t, 1H); 4.79 (m, 1H); 4.88 (d, 2H); 5.04 (t, 1H); 5.20 (m, 1H); 7.43 (dd, 1H); 7.52 to 7.64 (m, 5H); 7.80 (d, 1H); 8.21 (d, 1H).

Example 22 tert-Butyl N-((5R)-3-{2,2'-difluoro-4'-[5-(hydroxymethyl)-4,5-dihydroisoxazol-3-yl]-1,1'-biphenyl-4-yl}-2-oxo-1,3-oxazolidin-5-yl)methyl N-(isoxazol-3-yl) carbamate

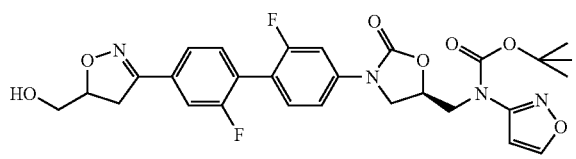

Yield=186 mg (67%)

MS (ESP+): (M+H)+ 571.27 for $C_{28}H_{28}F_2N_4O_7$

NMR (DMSO-$d_6$) δ: 1.52 (s, 9H); 3.25 (dd, 1H); 3.47 (dd, 1H); 3.51 to 3.60 (m, 2H); 3.94 (q, 1H); 4.04 (m, 1H); 4.30 (t, 1H); 4.34 (d, 1H); 4.79 (m, 1H); 5.05 (t, 1H); 5.07 (m, 1H); 6.90 (s, 1H); 7.51 (dd, 1H); 7.55 to 7.58 (m, 2H); 7.59 to 7.66 (m, 3H); 8.85 (d, 1H).

Example 23

(5R)-3-[2'-Fluoro-4'-[5-(hydroxymethyl)-4,5-dihydroisoxazol-3-yl]-1,1'-biphenyl-4-yl}-5-(hydroxymethyl)-1,3-oxazolidin-2-one

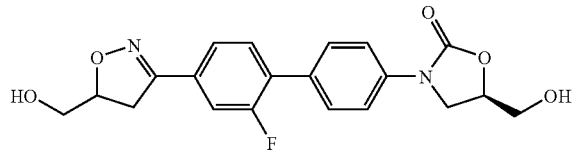

Yield=76 mg (23%)

MS (ESP+): (M+H)+ 387.24 for $C_{20}H_{19}FN_2O_5$

NMR (DMSO-$d_6$) δ: 3.25 (dd, 1H); 3.46 (dd, 1H); 3.51 to 3.57 (m, 2H); 3.59 to 3.63 (m, 1H); 3.70 to 3.74 (m, 1H); 3.91 (q, 1H); 4.17 (t, 1H); 4.72 to 4.82 (m, 2H); 5.04 (t, 1H); 5.25 (t, 1H); 7.57 to 7.61 (m, 2H); 7.64 to 7.67 (m, 3H); 7.71 to 7.75 (m, 2H).

Example 24

N-[((5S)-3-{2'-Fluoro-4'-[5-(hydroxymethyl)-4,5-dihydroisoxazol-3-yl]-1,1'-biphenyl-4-yl}-2-oxo-1,3-oxazolidin-5-yl)methyl]acetamide

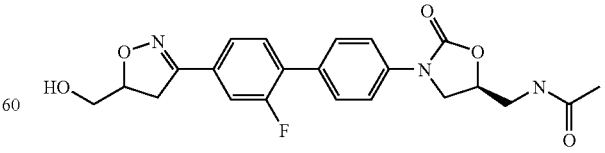

Yield=149 mg (61%)

MS (ESP+): (M+H)+ 428.31 for $C_{22}H_{22}FN_3O_5$

NMR (DMSO-$d_6$) δ: 1.85 (s, 3H); 3.24 (dd, 1H); 3.42 to 3.48 (m, 3H); 3.50 to 3.58 (m, 2H); 3.81 (q, 1H); 4.19 (t, 1H);

4.75 to 4.88 (m, 2H); 5.03 (t, 1H); 7.56 to 7.60 (m, 2H); 7.63 to 7.67 (m, 3H); 7.68 to 7.70 (m, 2H); 8.27 (t, 1H).

Example 25

{3-[2,2'-Difluoro-4'-(5-hydroxymethyl-4,5-dihydro-isoxazol-3-yl)-1,1'-biphenyl-4-yl]-4,5-dihydro-isoxazol-5-yl}methanol

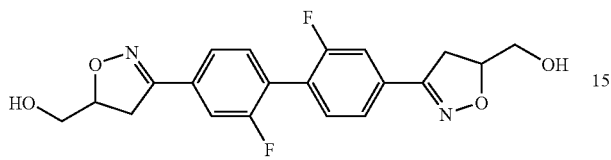

Yield=45 mg (60%)

MS (ESP+): (M+H)+ 389.25 for $C_{20}H_{19}F_2N_2O_4$

NMR (DMSO-$d_6$) δ: 3.26 (dd, 2H); 3.47 (dd, 2H); 3.51 to 3.59 (m, 4H); 4.79 (m, 2H); 5.04 (t, 2H); 7.59 to 7.67 (m, 6H).

Intermediates for Examples 19 to 25 were prepared as follows.

3-(4-Bromo-3-fluorophenyl)-5-({[tert-butyl(dimethyl)silyl]oxy}methyl)-4,5-dihydroisoxazole

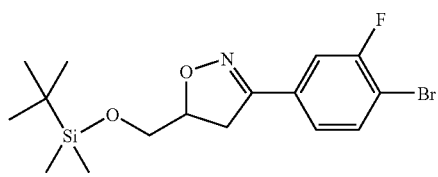

[3-(4-Bromo-3-fluorophenyl)-4,5-dihydroisoxazol-5-yl]methanol (7.518 g, 27.4 mmol) was dissolved in a mixture of triethylamine (4.59 ml, 33.0 mmol) and dichloromethane (100 ml). The resulting solution was cooled to 0° C., then a 1M solution of tert-butyldimethylsilylchloride (30.2 ml) in dichloromethane was added dropwise over 30 minutes. 4-Dimethylamino pyridine (0.67 g, 5.48 mmol) was added and the reaction mixture left to stir overnight at room temperature. The reaction mixture was washed with water (200 ml). The dichloromethane layer was separated, dried over magnesium sulfate, filtered and concentrated in vacuo to yield 9.263 g (87%) of the desired compound as a colourless oil.

MS (ESP+): (M+H)+ 388 & 390 for $C_{16}H_{23}BrFNO_2Si$

NMR (DMSO-$d_6$) δ: 0.04 (s, 3H); 0.06 (s, 3H); 0.82 (s, 9H); 3.19 (dd, 1H); 3.44 (dd, 1H); 3.68 to 3.78 (m, 2H); 4.82 (m, 1H); 7.47 (dd, 1H); 7.47 (dd, 1H); 7.47 (t, 1H).

5-({[tert-Butyl(dimethyl)silyl]oxy}methyl)-3-[3-fluoro-4-(trimethylstannyl)phenyl]-4,5-dihydroisoxazole

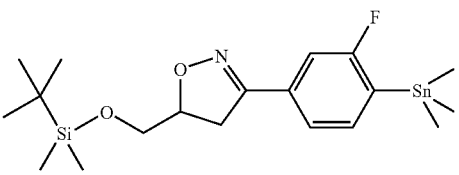

3-(4-Bromo-3-fluorophenyl)-5-({[tert-butyl(dimethyl)silyl]oxy}methyl)-4,5-dihydroisoxazole (5.403 g, 14.6 mmol) was dissolved in dry 1,4-dioxane (50 ml). The solution was placed under an atmosphere of argon. Hexamethylditin (5.26 g, 16 mmol) was added followed by bis(triphenylphosphine) palladium(II) chloride (0.512 g, 0.73 mmol). The reaction mixture was stirred at 90° C. for 90 minutes under an atmosphere of argon. The solvent was removed in vacuo and then the crude product re-dissolved in ethyl acetate (100 ml). Silica gel (5 ml) was added and the mixture concentrated in vacuo. This was then subjected to column chromatography (50 g silica gel bond elut: 0% to 50% ethyl acetate/hexanes) to yield 4.893 g (74%) of the desired compound as a colourless oil.

MS (APCI): (M+H)+ 471, 472, 473, 474 & 475 for $C_{13}H_{32}FNO_2SiSn$

NMR (DMSO-$d_6$) δ: 0.05 (s, 3H); 0.07 (s, 3H); 0.35 (t, 9H); 0.83 (s, 9H); 3.17 (dd, 1H); 3.42 (dd, 1H); 3.68 to 3.77 (m, 2H); 4.79 (m, 1H); 7.35 (dd, 1H); 7.47 to 7.53 (m, 2H).

N-[((5S)-3-[4'-[5-(4 [tert-Butyl(dimethyl)silyl]oxy}methyl)-4,5-dihydroisoxazol-3-yl]-2,2'-difluoro-1,1'-biphenyl-4-yl}-2-oxo-1,3-oxazolidin-5-yl)methyl]acetamide

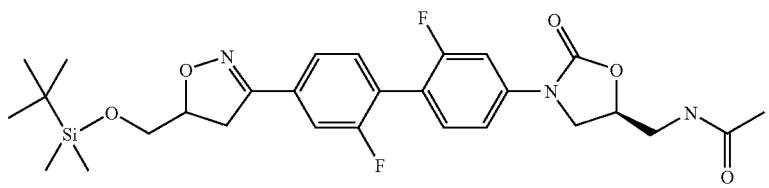

N-{[(5S)-3-(3-Fluoro-4-iodophenyl)-2-oxo-1,3-oxazolidin-5-yl]methyl}acetamide (378 mg, 1.0 mmol) and copper (I) iodide (39 mg, 0.2 mmol) were dissolved in dry 1-methyl-2-pyrrolidinone (2 ml) and the reaction mixture placed under an atmosphere of argon. Tetrakis(triphenylphosphine)palladium(0) (58 mg, 0.05 mmol) was added followed by a solution of 5-({[tert-butyl(dimethyl)silyl]oxy}methyl)-3-[3-fluoro-4-(trimethylstannyl)phenyl]-4,5-dihydroisoxazole (525 mg, 1.1 mmol) in 1-methyl-2-pyrrolidinone (2 ml) and the reaction mixture stirred for 16 hours at 90° C. Water (20 ml) and ethyl acetate (20 ml) were added and the insoluble materials filtered off. The ethyl acetate layer was separated, dried over magnesium sulphate, filtered then concentrated in vacuo onto silica gel (2 g). This was purified by column chromatography (20 g silica gel bond elut: 25% to 100% ethyl acetate/hexanes) to yield 416 mg (74%) of the desired compound.

MS (ESP+): (M+H)+ 560.38 for $C_{28}H_{35}F_2N_3O_5Si$

NMR (DMSO-d$_6$) δ: 0.06 (s, 3H); 0.08 (s, 3H); 0.85 (s, 9H); 1.86 (s, 3H); 3.23 (dd, 1H); 3.42 to 3.51 (m, 3H); 3.72 (dd, 1H); 3.78 (dd, 1H); 3.82 (q, 1H); 4.20 (t, 1H); 4.79 (m, 1H); 4.84 (m, 1H); 7.47 (dd, 1H); 7.52 to 7.68 (m, 5H); 8.28 (t, 1 H).

The following intermediate examples were prepared by a procedure similar to that used for the intermediate example above.

(5R)-3-{4'-[5-({[tert-Butyl(dimethyl)silyl]oxy}methyl)-4,5-dihydroisoxazol-3-yl]-2,2'-difluoro-1,1'-biphenyl-4-yl}-5-[(4-methyl-1H-1,2,3-triazol-1-yl)methyl]-1,3-oxazolidin-2-one

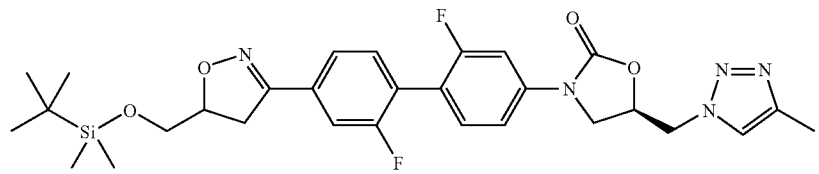

Yield=512 mg (88%)

MS (ESP+): (M+H)+ 584.42 for $C_{29}H_{35}F_2N_5O_4Si$

NMR (DMSO-d$_6$) δ: 0.06 (s, 3H); 0.08 (s, 3H); 0.85 (s, 9H); 2.71 (s, 3H); 3.23 (dd, 1H); 3.48 (dd, 1H); 3.72 (dd, 1H); 3.78 (dd, 1H); 3.95 (q, 1H); 4.31 (t, 1H); 4.79 (d, 2H); 4.84 (m, 1H); 5.16 (m, 1H); 7.44 (dd, 1H); 7.51 to 7.68 (m, 5H); 7.91 (s, 1H).

The following intermediate examples were prepared by a similar procedure to the example above but used 0.4 mmol of copper (I) iodide and 0.1 mmol of tetrakis(triphenylphosphine)palladium(0).

(5R)-3-{4'-[5-({[tert-Butyl(dimethyl)silyl]oxy}methyl)-4,5-dihydroisoxazol-3-yl]-2,2'-difluoro-1,1'-biphenyl-4-yl}-5-(1H-1,2,3-triazol-1-ylmethyl)-1,3-oxazolidin-2-one

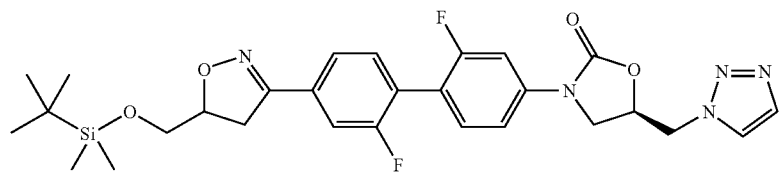

Yield=355 mg (62%)

MS (ESP+): (M+H)+ 570.40 for $C_{28}H_{33}F_2N_5O_4Si$

NMR (DMSO-d$_6$) δ: 0.06 (s, 3H); 0.08 (s, 3H); 0.85 (s, 9H); 3.23 (dd, 1H); 3.48 (dd, 1H); 3.72 (d, 1H); 3.78 (dd, 1H); 3.99 (q, 1H); 4.32 (t, 1H); 4.85 (m, 1H); 4.88 (d, 2H); 5.20 (m, 1H); 7.43 (dd, 1H); 7.51 to 7.68 (m, 5H); 7.80 (d, 1H); 8.21 (d, 1H).

tert-butyl N-((5R)-3-{4'-[5-({tert-butyl(dimethyl)
silyl]oxy}methyl)-4,5-dihydroisoxazol-3-yl]-2,2'-
difluoro-1,1'-biphenyl-4-yl}-2-oxo-1,3-oxazolidin-5-
yl)methyl N-(isoxazol-3-yl) carbamate

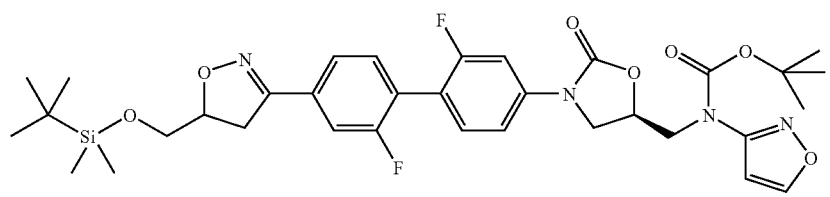

Yield=333 mg (49%)

MS (ESP+): (M+H)$^+$ 685.46 for $C_{34}H_{42}F_2N_4O_7Si$

NMR (DMSO-d$_6$) δ: 0.06 (s, 3H); 0.08 (s, 3H); 0.85 (s, 9H); 1.52 (s, 9H); 3.24 (dd, 1H); 3.48 (dd, 1H); 3.72 (dd, 1H); 3.79 (dd, 1H); 3.95 (dd, 1H); 4.01 to 4.07 (m, 2H); 4.30 (t, 1H); 4.84 (m, 1H); 5.07 (m, 1H); 6.90 (s, 1H); 7.50 to 7.66 (m, 6H); 8.85 (d, 1H).

(5R)-3-{4'-[5-({[tert-Butyl(dimethyl)silyl]
oxy}methyl)-4,5-dihydroisoxazol-3-yl]-2'-fluoro-1,
1°-biphenyl-4-yl}-5-(hydroxymethyl)-1,3-oxazoli-
din-2-one

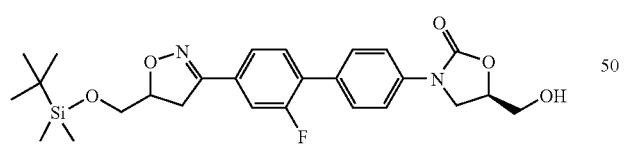

Yield=422 mg (84%)

MS (ESP+): (M+H)$^+$ 501.36 for $C_{26}H_{33}FN_2O_5Si$

NMR (DMSO-d$_6$) δ: 0.06 (s, 3H); 0.08 (s, 3H); 0.85 (s, 9H); 3.23 (dd, 1H); 3.48 (dd, 1H); 3.60 (dd, 1H); 3.71 (dd, 2H); 3.78 (dd, 1H); 3.91 (q, 1H); 4.16 (t, 1H); 4.76 (m, 1H); 4.83 (m, 1H); 5.26 (br s, 1H); 7.56 to 7.70 (m, 5H); 7.73 (d, 2H).

N-[((5S)-3-{4'-[5-({[tert-Butyl(dimethyl)silyl]oxy}methyl)-4,5-dihydroisoxazol-3-yl]-2'-fluoro-1,1'-biphenyl-4-yl}-2-oxo-1,3-oxazolidin-5-yl)methyl]acetamide

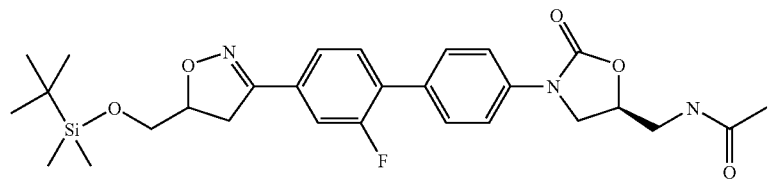

Yield=310 mg (57%)

MS (ESP+): (M+H)$^+$ 501.36 for $C_{28}H_{36}FN_3O_5Si$

NMR (DMSO-d$_6$) δ: 0.06 (s, 3H); 0.08 (s, 3H); 0.85 (s, 9H); 1.86 (s, 3H); 3.23 (dd, 1H); 3.45 to 3.51 (m, 3H); 3.71 (dd, 1H); 3.78 (dd, 1H); 3.82 (q, 1H); 4.20 (t, 1H); 4.78 (m, 1H); 4.83 (m, 1H); 7.56 to 7.71 (m, 7H); 8.28 (t, 1H).

3-{4'-[5-({[tert-Butyl(dimethyl)silyl]oxy}methyl)-4,5-dihydroisoxazol-3-yl]-2,2'-difluoro-1,1'-biphenyl-4-yl[}-5-[tert-butyl(dimethyl)silyl]oxymethyl-4,5-dihydroisoxazole (4-iodophenyl)-2-oxo-1,3-oxazolidin-5yl]methyl}acetamide (0.40 g, 1.2 mM), tris(dibenzylideneacetone)dipalladium (0) (0.037 g, 0.040 mM), and tri-2-furylphosphine (0.019, 0.080 mM) were weighed into a flask and degassed. 1-Methyl-2-pyrrolidinone (3 mL) was added and the reaction was heated at 90° C. for 21 hours. The black mixture was diluted with 1-methyl-2-pyrrolidinone (10 ml) and filtered through celite, collecting the brown band that migrated through the pad. Water was added to the solution causing a light brown solid to precipitate. The mixture was filtered after refrigeration for 2 hours to give the desired product as a brown solid (0.037 g).

MS (ESP): 467 (MH$^+$) for $C_{24}H_{26}N_4O_6$

NMR (DMSO-d$_6$) δ: 1.77 (s, 6H); 3.37 (t, 4H); 3.72 (t, 2H); 4.10 (t, 2H); 4.67-4.69 (m, 2H); 7.55 (d, 4H); 7.65 (d, 4H); 8.20 (t, 2H).

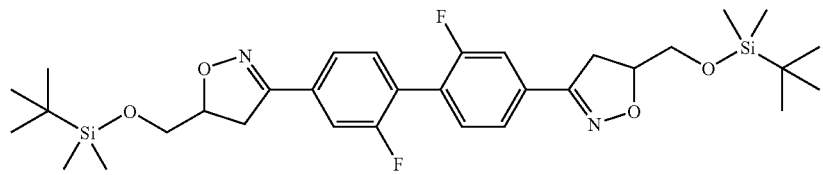

Yield=128 mg

MS (ESP+): (M+H)$^+$ 617.48 for $C_{32}H_{46}F_2N_2O_4Si_2$

NMR (DMSO-d$_6$) δ: 0.06 (s, 6H); 0.08 (s, 6H); 0.85 (s, 18H); 3.24 (dd, 2H); 3.9 (dd, 2H); 3.72 (dd, 2H); 3.79 (dd, 2H); 4.84 (m, 2H); 7.59 to 7.67 (m, 6H).

Example 26

(5S,5'S)-N-(3-{4'-[5-(Acetylamino-methyl)-2-oxo-oxazolidin-3-yl]-biphenyl-4-yl}-2-oxo-oxazolidin-5-ylmethyl-acetamide

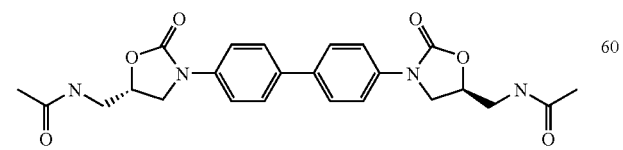

N-({(5S)-2-Oxo-3-[4-(trimethylstannyl)phenyl]-1,3-oxazolidin-5-yl}methyl)acetamide (0.36 g, 1 mM), N-{[(5S)-3-

Example 27

(5R,5'R)-3-[2,2'-difluoro-4'-(5-[4-methyl-1H-1,2,3-triazolyl-1-ylmethyl]-2-oxo-1,3-oxazolidin-3-yl)-1,1'-biphenyl-4-yl]-5-[(4-methyl-1H-1,2,3-triazol-1-ylmethyl]-1,3-oxazolidin-2-one

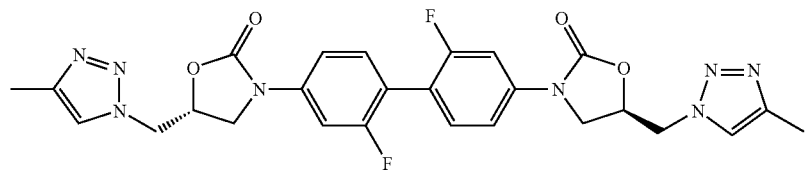

Using essentially the same procedure as Example 26, but starting from (5R)-3-(3-fluoro-4-iodophenyl)-5-[(4-methyl-1H-1,2,3-triazol-1-yl)methyl]-1,3-oxazolidin-2-one (0.40 g, 1.00 mM) and (5R)-3-[3-fluoro-4-(trimethylstannyl)phenyl]-5-[(4-methyl-1H-1,2,3-triazol-1-yl)methyl]-1,3-oxazolidin-2-one (0.53 g 1.20 mM), gave the title compound as a brown solid (0.50 g).

MS (ESP): 551 (MH$^+$) for $C_{26}H_{24}F_2N_8O_4$

NMR (DMSO-d$_6$) δ: 2.25 (s, 6H); 3.95 (dd, 2H); 4.30 (t, 2H); 4.80 (d, 4H); 5.16 (m, 2H); 7.41 (dd, 2H); 7.49 (m, 2H); 7.57 (m, 2H); 7.90 (s, 2H).

The intermediates for Example 27 were prepared as follows:

(5R)-3-[3-Fluoro-4-(trimethylstannyl)phenyl]-5-[(4-methyl-1H-1,2,3-triazol-1-yl)methyl]-1,3-oxazolidin-2-one

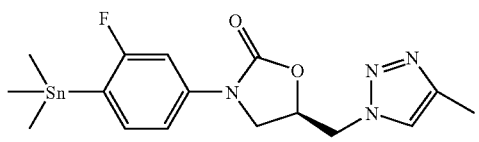

(5R)-3-(3-Fluoro-4-iodophenyl)-5-[(4-methyl-1H-1,2,3-triazol-1-yl)methyl]-1,3-oxazolidin-2-one (5.12 g, 12.7 mM) and bis(triphenylphosphine)palladium(II) chloride (0.45 g, 0.05 mM) were placed in a flask and degassed. Dioxane (50 ml) was added followed by hexamethylditin (5.00 g, 15.3 mM) and the reaction was degassed. The orange-brown mixture was heated at 90° C. for 20 hours, cooled and adsorbed into silica gel. The residue was purified by flash chromatography using 50% hexanes/ethyl acetate to ethyl acetate. Relevant fractions were combined to give the desired product as a brown solid (3.91 g).

MS (ESP): 440 (MH$^+$) for $C_{16}H_{21}FN_4O_2Sn$

NMR (DMSO-d$_6$) δ: 0.09 (t, 9H); 2.00 (s, 3H); 3.65 (dd, 1H); 4.00 (t, 1H); 4.53 (d, 2H); 4.88 (m, 1H); 7.03 (dd, 1H); 7.11 (dd, 1H); 7.18 (dd, 1H); 7.64 (s, 1H).

(5R)-3-(3-Fluoro-4-iodophenyl)-5-[(4-methyl-1H-1,2,3-triazol-1-yl)methyl]-1,3-oxazolidin-2-one

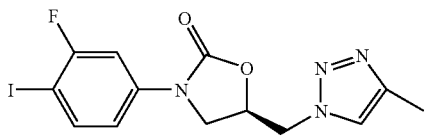

Silver trifluoroacetate (0.52 g, 2.35 mM) was added to a solution of (5R)-3-(3-fluorophenyl)-5-[(4-methyl-1H-1,2,3-triazol-1-yl)methyl]-1,3-oxazolidin-2-one (0.50 g, 1.81 mM) in dichloromethane (15 mL). Iodine (0.55 g, 2.17 mM) was added over 1.5 h, and reaction mixture was stirred overnight. After 16 h, the solids were removed by filtration and additional silver trifluoroacetate (0.38 g, 1.72 mM) and iodine (0.27 g, 1.06 mM) were added. After an additional 24 h, the reaction mixture was filtered. The filter cake was washed with methanol. The methanol filtrate was concentrated under vacuum to give 0.31 g of the title product.

MS (ESP): 403 (M+1) for $C_{13}H_{12}FIN_4O_2$

NMR (DMSO-d$_6$) δ: 2.24 (s, 3H); 3.89 (dd, 1H); 4.23 (t, 1H); 4.76 (d, 2H); 5.12 (m, 1H); 7.17 (dd, 1H); 7.51 (dd, 1H); 7.84 (t, 1H); 7.88 (s, 1H).

(5R)-3-(3-Fluorophenyl)-5-[(4-methyl-1H-1,2,3-triazol-1-yl)methyl]-1,3-oxazolidin-2-one

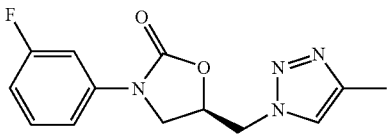

N,N-Diisopropylethylamine (3.20 mL, 18.35 mM) was added to a solution of (5S)-5-(aminomethyl)-3-(3-fluorophenyl)-1,3-oxazolidin-2-one (0.77 g, 3.57 mM; see Dong Pharmaceuticals WO 0194342) in anhydrous methanol (25 mL). The solution was cooled to 0° C., and N'-[2,2-dichloro-1-methylethylidene]-4-methylbenzenesulfonohydrazide (1.28 g, 4.58 mM) was added. The solution was warmed to room temperature and stirred overnight. The reaction mixture was then concentrated under vacuum and chromatographed on silica gel using 2% methanol/dichloromethane to give 0.71 g of the title product.

MS (ESP): 277 (M+1) for $C_{13}H_{13}FN_4O_2$

NMR (DMSO-$d_6$) δ: 2.24 (s, 3H); 3.90 (dd, 1H); 4.25 (t, 1H); 4.77 (d, 2H); 5.13 (m, 1H); 6.99 (m, 1H); 7.28 (d, 1H); 7.42-7.48 (m, 2H); 7.89 (s, 1H).

Example 28

(5R)-5-(Hydroxymethyl)-3-{4'-[(5R)-2-oxo-5-(1H-1,2,3-triazol-1-ylmethyl)-1,3-oxazolidin-3-yl]-1,1'-biphenyl-4-yl}-1,3-oxazolidin-2-one

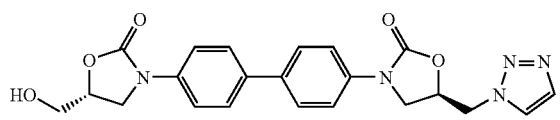

(5R)-3-(4-iodophenyl)-5-(1H-1,2,3-triazol-1-ylmethyl)-1,3-oxazolidin-2-one (0.39 g, 1.00 mM), tris(dibenzylideneacetone)dipalladium (0) (0.037 g, 0.040 mM), and tri-2-furylphosphine (0.0199, 0.080 mM) were weighed into a flask and degassed. 1-Methyl-2-pyrrolidinone (3 ml) was added and the flask was degassed. (5R)-5-({tert-Butyl(dimethyl)silyl]oxy}methyl)-3-[4-(trimethylstannyl)phenyl]-1,3-oxazolidin-2-one (0.71 g, 1.50 mM) was added and the flask was degassed. The reaction was stirred at 90° for 22 hours. The black mixture was adsorbed onto silica gel and chromatographed using ethyl acetate to give an oily solid (1.78 g) that was dissolved in DMSO and purified using reverse phase HPLC (acetonitrile-water-1% trifluoroacetic acid). The protective tert-butyldimethylsilyl-group was removed adventitiously during the reverse phase purification to give the product directly as a light yellow solid (0.98 g).

MS (APCI Negative): 436 (MH$^+$) for $C_{22}H_{21}N_5O_5$

NMR (DMSO-$d_6$) δ: 3.44 (dd, 1H); 3.55 (dd, 1H); 3.73 (t, 1H); 3.79 (t, 1H); 3.98 (t, 1H); 4.14 (t, 1H); 4.57 (m, 1H); 4.72 (d, 2H); 5.01 (m, 1H); 7.41 (d, 2H); 7.51 (d, 2H); 7.54-7.57 (m, 4H); 7.63 (s, 1H); 8.04 (s, 1H).

The intermediate (5R)-5-({tert-Butyl(dimethyl)silyl]oxy}methyl)-3-[4-(trimethylstannyl)phenyl]-1,3-oxazolidin-2-one is described in Example 29; the intermediate (5R)-3-(4-iodophenyl)-5-(1H-1,2,3-triazol-1-ylmethyl)-1,3-oxazolidin-2-one is one of the intermediates described before Example 1.

Example 29

(5R)-5-({[tert-Butyl(dimethyl)silyl]oxy}methyl)-3-(4'-[(5R)-5-[(4-methyl-1H-1,2,3-triazol-1-yl)methyl]-2-oxo-1,3-oxazolidin-3-yl]-1,1'-biphenyl-4-yl)-1,3-oxazolidin-2-one

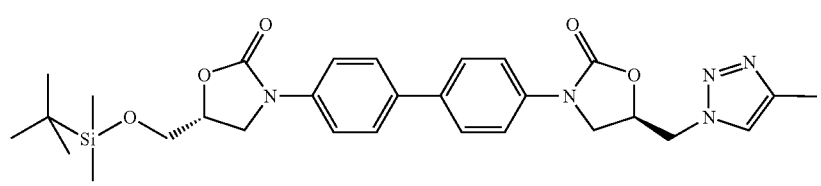

Using essentially the same procedure as Example 28, but starting from (5R)-3-(4-iodophenyl)-5-[(4-methyl-1H-1,2,3-triazol-1-yl)methyl]-1,3-oxazolidin-2-one (0.34 g, 1.00 mM) gave the title compound as a white solid (0.016 g).

NMR (DMSO-$d_6$) δ: 0.00 (s, 6H); 0.75 (s, 9H); 2.18 (s, 3H); 3.76-3.87 (m, 4H); 4.11 (t, 1H); 4.23 (t, 1H); 4.72 (d, 2H); 5.06 (m, 2H); 7.49-7.52 (m, 2H); 7.59-7.66 (m, 6H); 7.83 (s, 1H).

Intermediates for Example 29 may be prepared as follows:

(5R)-5-({[tert-Butyl(dimethyl)silyl]oxy}methyl)-3-[4-(trimethylstannyl)phenyl]-1,3-oxazolidin-2-one

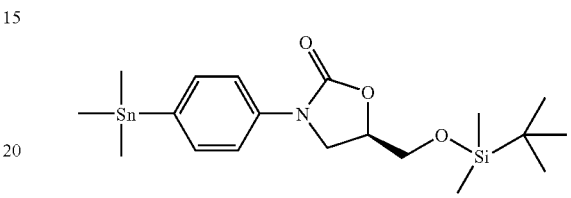

Using the procedure described for (5R)-3-[3-fluoro-4-(trimethylstannyl)phenyl]-5-[(4-methyl-1H-1,2,3-triazol-1-yl)methyl]-1,3-oxazolidin-2-one (above), but starting from (5R)-5-({[tert-butyl(dimethyl)silyl]oxy}methyl)-3-(4-iodophenyl)-1,3-oxazolidin-2-one (2.45 g, 5.66 mM) gave the title compound as a white solid after chromatography, using hexanes then 20% ethyl acetate/hexanes (1.59 g).

MS (ESP): 471 (MH$^+$) for $C_{19}H_{33}NO_3SiSn$

NMR (DMSO-$d_6$) δ: 0.00 (s, 6H); 0.21 (s, 9H); 0.75 (s, 9H); 3.68-3.75 (m, 2H); 3.83 (d, 1H); 4.05 (t, 1H); 4.70 (m, 1H); 7.41-7.48 (m, 4H).

(5R)-5-({[tert-Butyl(dimethyl)silyl]oxy}methyl)-3-(4-iodophenyl)-1,3-oxazolidin-2-one

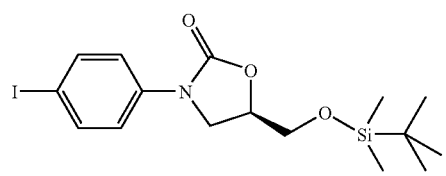

(5R)-5-(Hydroxymethyl)-3-(4-iodophenyl)-1,3-oxazolidin-2-one (2.00 g, 1.00 mM) was dissolved in methylene chloride (12 ml). N,N-Dimethylaminopyridine (0.76 g, 7.52 mM) and triethylamine (0.76 g, 7.52 mM) were added and the solution was degassed. A 1N solution of tert-butyldimethylsilyl chloride in methylene chloride (7 ml) was added and the reaction was stirred at room temperature for 16 hours. The yellow solution was diluted with water and the product was extracted using methylene chloride (3×200 ml). The organic layer was dried (magnesium sulfate), filtered and concentrated to give the desired product as a light yellow solid (2.54 g).

NMR (DMSO-$d_6$) δ: 0.00 (s, 6H); 0.74 (s, 9H); 3.69-3.73 (m, 2H); 3.83 (d, 1H); 4.06 (t, 1H); 4.73 (m, 1H); 7.36 (d, 2H); 7.67 (d, 2H).

Example 30

(5R)-5-({[tert-Butyl(dimethyl)silyl]oxy}methyl)-3-(2'-fluoro-4'-{(5R)-5-[(4-methyl-1H-1,2,3-triazol-1-yl)methyl]-2-oxo-1,3-oxazolidin-3-yl}-1,1'-biphenyl-4-yl)-1,3-oxazolidin-2-one

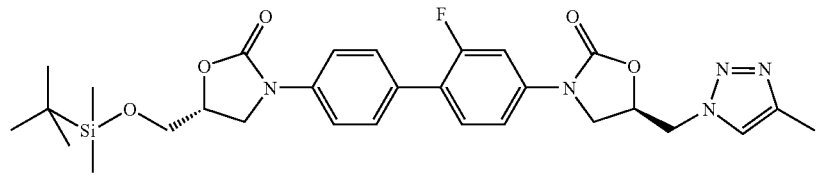

Using essentially the same procedure as Example 28, but starting from (5R)-5-({[tert-butyl(dimethyl)silyl]oxy}methyl)-3-(4-iodophenyl)-1,3-oxazolidin-2-one (0.43 g, 1.00 mM) and adding (5R)-3-[3-fluoro-4-(trimethylstannyl)phenyl]-5-[(4-methyl-1H-1,2,3-triazol-1-yl)methyl]-1,3-oxazolidin-2-one (0.66 g, 1.50 mM) gave the title compound as a white solid (0.025 g).

NMR (DMSO-$d_6$) δ: 0.00 (s, 6H); 0.75 (s, 9H); 2.17 (s, 3H); 3.82-3.87 (m, 2H); 4.11-4.23 (m, 2H); 4.68-4.73 (m, 4H); 5.03-5.09 (m, 2H); 7.31-7.45 (m, 2H); 7.52-7.70 (m, 4H); 7.60-7.62 (d, 2H); 7.81-7.82 (m, dH).

Example 31

N-[((5S)-3-{4'-[(5R)-5-({[tert-Butyl(dimethyl)sily]oxy}methyl)-2-oxo-1,3-oxazolidin-3-yl]-2,2'-difluoro-1,1'-biphenyl-4-yl}-2-oxo-1,3-oxazolidin-5-yl)methyl]acetamide Using essentially the same procedure as Example 28, but starting from N-{[(5S)-3-(3-fluoro-4-iodophenyl)-2-oxo-1,3-oxazolidin-5-yl]methyl}acetamide (0.38 g, 1.00 mM) and adding (5R)-5-({[tert-butyl(dimethyl)silyl]oxy}methyl)-3-[3-fluoro-4-(trimethylstannyl)phenyl]-1,3-oxazolidin-2-one (0.73 g, 1.50 mM) gave the title compound as a light yellow solid (0.334 g).

NMR (DMSO-$d_6$) δ: 0.00 (s, 6H); 0.74 (s, 9H); 1.79 (s, 3H); 3.38-3.39 (t, 2H); 3.70-3.83 (m, 4H); 4.10-4.14 (m, 2H); 4.70-4.76 (m, 2H); 7.37-7.42 (m, 3H); 7.56 (t, 2H); 8.20 (t, 1H).

Intermediates for Example 31 may be prepared as follows:

(5R)-5-({[tert-Butyl(dimethyl)silyl]oxy}methyl)-3-[3-fluoro-4-(trimethylstannyl)phenyl]-1,3-oxazolidin-2-one

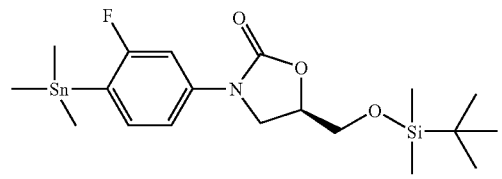

Using essentially the same procedure as described for (5R)-5-({[tert-butyl(dimethyl)silyl]oxy}methyl)-3-[4-(trimethylstannyl)phenyl]-1,3-oxazolidin-2-one, but starting from (5R)-5-({[tert-butyl(dimethyl)silyl]oxy}methyl)-3-(3-fluoro-4-iodophenyl)-1,3-oxazolidin-2-one (1.97 g, 4.37 mM) gave the title compound as a white solid after chromatography using hexanes then 20% ethyl acetate/hexanes (1.75 g)

MS (ESP): 489 (MH$^+$) for $C_{19}H_{32}FNO_3SiSn$.

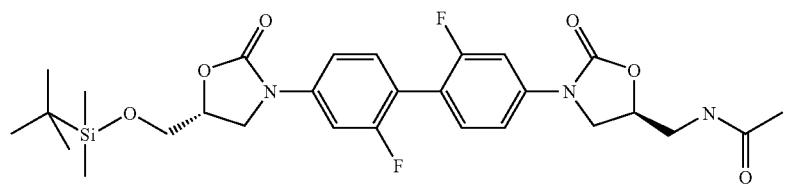

NMR (DMSO-$d_6$) δ: 0.00 (s, 6H); 0.27 (s, 9H); 0.74 (s, 9H); 3.69-3.76 (m, 2H); 3.83 (d, 1H); 4.06 (t, 1H); 4.74 (m, 1H); 7.27 (d, 1H): 7.34-7.39 (m, 2H).

(5R)-5-({[tert-Butyl(dimethyl)silyl]oxy}methyl)-3-(3-fluoro-4-iodophenyl)-1,3-oxazolidin-2-one

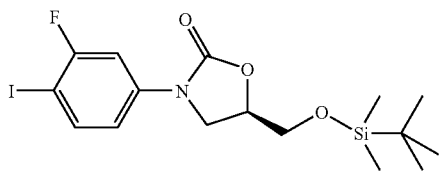

Using essentially the same procedure as that used for (5R)-5-({[tert-butyl(dimethyl)silyl]oxy}methyl)-3-(4-iodophenyl)-1,3-oxazolidin-2-one (above), but starting from (5R)-3-(3-fluoro-4-iodophenyl)-5-(hydroxymethyl)-1,3-oxazolidin-2-one (2.0 g, 1.0 mM) gave the title compound as a light yellow soild after chromatography using 50% ethyl acetate/hexanes (1.94 g).

MS (ESP): 452 (MH$^+$) for $C_{16}H_{23}FINO_3Si$

NMR (DMSO-$d_6$) δ: 0.00 (s, 6H); 0.75 (s, 9H); 3.69-3.72 (m, 2H); 3.84 (d, 1H); 4.08 (t, 1H); 4.76 (m, 1H); 7.19 (d, 1H); 7.54 (d, 1H); 7.78 (t, 1H).

Example 32

(5R)-3-{2-Fluoro-4'-[(5R)-5-(hydroxymethyl)-2-oxo-1,3-oxazolidin-3-yl]-1,1'-biphenyl-4-yl}-5-[(4-methyl-1H-1,2,3-triazol-1-yl)methyl]-1,3-oxazolidin-2-one

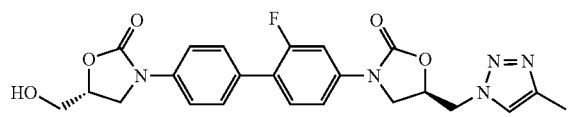

(5R)-5-({[tert-Butyl(dimethyl)silyl]oxy}methyl)-3-(4'-{(5R)-5-[(4-methyl-1H-1,2,3-triazol-1-yl)methyl]-2-oxo-1,3-oxazolidin-3-yl}-1,1'-biphenyl-4-yl)-1,3-oxazolidin-2-one (0.016 g, 0.030 mM) was suspended in tetrahydrofuran (0.5 ml) and a 1N solution of tetrabutylammoniumfluoride in tetrahydrofuran (0.03 ml) was added. The reaction was stirred at room temperature for one hour. The cloudy suspension was concentrated as a white residue.

MS (APCI Negative): 468 (MH$^+$) for $C_{23}H_{22}FN_5O_5$

NMR (DMSO-$d_6$) δ: 2.28 (s, 3H); 3.65 (t,1H); 3.71 (dd, 1H); 3.96 (m, 1H); 4.16 (t, 1H); 4.29-4.34(m, 2H); 4.74-4.77 (m, 1H); 4.82-4.83 (d, 2H); 5.15-5.18 (m, 1H); 7.61-7.62 (d, 2H); 7.70-7.76 (m, 6H); 7.94 (s, 1H).

Example 33

(5R)-5-(Hydroxymethyl)-3-(4'-{(5R)-5-[(4-methyl-1H-1,2,3-triazol-1-yl)methyl]-2-oxo-1,3-oxazolidin-3-yl}-1,1'-biphenyl-4-yl)-1,3-oxazolidin-2-one

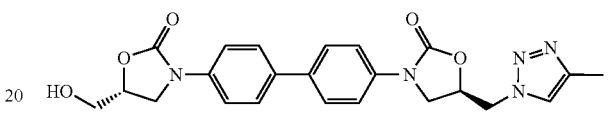

Using essentially the same procedure as described for Example 32, but starting with (5R)-5-({[tert-butyl(dimethyl)silyl]oxy}methyl)-3-(4'-{(5R)-5-[(4-methyl-1H-1,2,3-triazol-1-yl)methyl]-2-oxo-1,3-oxazolidin-3-yl}-1,1'-biphenyl-4-yl)-1,3-oxazolidin-2-one (0.025 g, 0.043 mM) gave the title compound as a white residue.

MS (ESP): 448 (MH$^-$) for $C_{23}H_{23}N_5O_5$

NMR (DMSO-$d_6$) δ: 2.26 (s, 3H); 3,59-3.68 (dq, 2H); 3.78 (t, 1H); 3.95-4.02 (m, 2H); 4.12 (t, 1H); 4.28-4.33 (q, 1H); 4.72-4.73 (m, 1H); 4.80-4.81 (d, 2H); 5.16-5.19 (m, 1H); 7.39 (d, 1H); 7.56-7.60 (m, 4H); 7.70-7.72 (d, 2H); 7.93 (s, 1H).

Example 34

(5R)-3-{4'-[5-({[tert-butyl(dimethyl)silyl]oxy}methyl)-4,5-dihydroisoxazol-3-yl]-1,1'-biphenyl-4-yl}-5-[(4-methyl-1H-1,2,3-triazol-1-yl)methyl]-1,3-oxazolidin-2-one

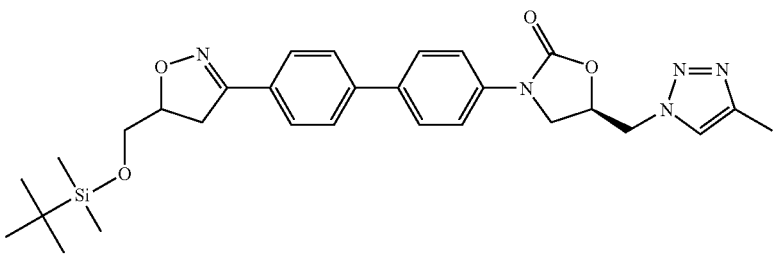

5-({[tert-Butyl(dimethyl)silyl]oxy}methyl)-3-[4-(trimethylstannyl)phenyl]4,5-dihydroisoxazole (0.70 g, 1.6 mmol), (5R)-3-(4-iodophenyl)-5-[(4-methyl-1H-1,2,3-triazol-1-yl)methyl]-1,3-oxazolidin-2-one (0.5 g, 1.29 mmol), tri-2-furyl phosphine (0.06 g, 0.26 mmol) and tris(dibenzylideneacetone)palladium (0) (0.12 g, 0.13 mmol) were dissolved in 1,4-dioxane (5 ml) and degassed three times. The mixture was then heated to 90° C. and stirred for 18 hr. LCMS indicated that the reaction was not yet complete, so it was cooled and an additional (0.12 g, 0.13 mmol) of tris(dibenzylidene acetone) palladium (0) was added, the mixture degassed and reheated to 110° C. for 3 hours, and 25° C. for 40 hours. The solution was concentrated in vacuo and purified by silica flash chromatography with 5-10% methanol in dichloromethane as eluent giving 0.2 g of the desired product as a yellow solid.

MS (ESP) 548.45 (MH+) for $C_{29}H_{37}N_5O_4Si$ $^1$HNMR (DMSO-$d_6$) δ: 0.05 (d, 6H); 0.83 (s, 9H); 2.24 (s, 3H); 3.22 (m, 1H); 3.46 (m, 1H); 4.77 (m, 4H); 5.12 (m, 1H); 7.36 (s, 1H); 7.58 (m, 4H); 7.74 (m, 6H); 7.88 (s, 1H).

The starting material for Example 34 was prepared as follows:

1-({[3-[4-(Trimethylstannyl)phenyl]-4,5-dihydroisoxazol-5-yl]methyl}-1H-1,2,3-triazole

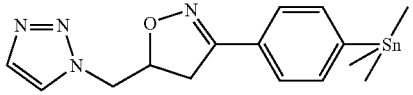

1-{[3-(4-Bromophenyl)-4,5-dihydroisoxazol-5-yl]methyl}-1H-1,2,3-triazole (3.7 g, 12.1 mmol) and trans-dichlorobis(triphenylphosphine) palladium (II) were dissolved in 1,4-dioxane (50 ml) and the solution was degassed three times. Hexamethylditin (5 g, 15.3 mmol) was added and the solution degassed. The solution was stirred and heated to 90° C. for 16 hours. The black reaction mixture was filtered through Celite and the Celite was washed with methanol. The methanol layer was concentrated in vacuo then purified by silica flash chromatography with 1.5-3% methanol in dichloromethane as eluent giving 4.6 g of the title compound.

MS (ESP) 393.06 (M+2H+) for $C_{15}H_{20}N_4OSn$ $^1$HNMR (DMSO-$d_6$) δ: 0.03 (s, 9H); 3.25 (dd, 1H); 3.59 (dd, 1H); 4.64 (m, 2H); 5.15 (m, 1H); 7.56 (s, 4H); 7.72 (s, 1H); 8.14 (s, 1H).

Example 35

(5R)-5-(1H-1,2,3-Triazol-1-ylmethyl)-3-{4'-[5-(1H-1,2,3-triazol-1-ylmethyl)-4,5-dihydroisoxazol-3-yl]-1,1'-biphenyl-4-yl}-1,3-oxazolidin-2-one

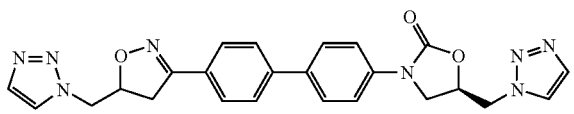

1-({3-[4-(Trimethylstannyl)phenyl]-4,5-dihydroisoxazol-5-yl}methyl)-1H-1,2,3-triazole (0.33 g, 0.84 mmol), (5R)-3-(4-iodophenyl)-5-(1H-1,2,3-triazol-1-ylmethyl)-1,3-oxazolidin-2-one (0.26 g, 0.7 mmol) and tri-2-furylphosphine (0.033 g, 0.14 mmol) were dissolved in 1,4-dioxane (6 ml) and degassed three times. Tris(dibenzylideneacetone) palladium (0) (0.064 g, 0.07 mmol) was added and the solution was degassed three times. The solution was stirred and heated to 110° C. for 3 hours and then 25° C. for 40 hours. LCMS showed that the reaction was not complete, so an additional (0.09 g, 0.1 mmol) of tris(dibenzylideneacetone)palladium (0) was added and the mixture was degassed and then heated to 90° C. for 6 hours, and 25° C. for 12 hours. The mixture was concentrated in vacuo and then purified by silica flash chromatography with 5-10% methanol in dichloromethane as eluent giving 0.05 g desired product.

MS (ESP) 471.31 (MH+) for $C_{24}H_{22}N_8O_3$ $^1$HNMR (DMSO-$d_6$) δ: 3.64 (m, 2H); 3.95 (dd, 1H); 4.30 (m, 1H); 4.68 (s, 2H); 4.86 (d, 2H); 5.17 (m, 2H); 7.6 (d, 2H) 7.75 (m, 8H); 8.17 (d, 2H).

Example 36

(5R)-3-{2-Fluoro-4'-[5-(1H-1,2,3-triazol-1-ylmethyl)-4,5-dihydroisoxazol-3-yl]-1,1'-biphenyl-4-yl}-5-[(4-methyl-1H-1,2,3-triazol-1-yl)methyl]-1,3-oxazolidin-2-one

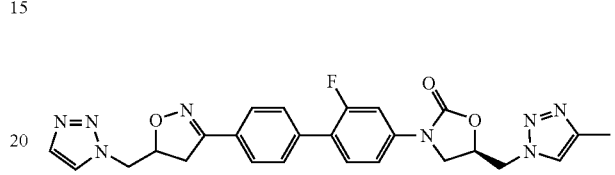

1-({3-[4-(Trimethylstannyl)phenyl]4,5-dihydroisoxazol-5-yl}methyl)-1H-1,2,3-triazole (0.33 g, 0.84 mmol), (5R)-3-(3-fluoro-4-iodophenyl)-5-[(4-methyl-1H-1,2,3-triazol-1-yl)methyl]-1,3-oxazolidin-2-one (0.27 g, 0.69 mmol) and tri-2-furylphosphine (0.033 g, 0.14 mmol) were dissolved in 1,4-dioxane (6 ml) and degassed three times. Tris(dibenzylideneacetone)palladium (0) (0.064 g, 0.07 mmol) was added and the solution was degassed three times. The solution was stirred and heated to 110° C. for 3 hours and then 25° C. for 40 hours. LCMS showed that the reaction was not complete, so an additional (0.09 g, 0.1 mmol) of tris (dibenzylideneacetone)palladium (0) was added and the mixture was degassed and then heated to 90° C. for 6 hours, and 25° C. for 12 hours. The mixture was concentrated in vacuo and then purified by silica flash chromatography with 5-10% methanol in dichloromethane as eluent giving 0.223 g desired product.

MS (ESP) 503.23 (MH+) for $C_{25}H_{23}FN_8O_3$ $^1$HNMR (DMSO-$d_6$) δ: 2.24 (s, 3H); 3.63 (dd, 1H); 3.94 (dd, 1H); 4.29 (m, 1H); 4.67 (m, 2H) 4.78 (d, 2H); 5.17 (m, 2H); 7.40 (dd, 1H); 7.54 (d, 1H); 7.65 (m, 7H); 7.89 (s, 1H); 8.16 (s, 1H).

Example 37

(5R)-3-{4'-[5-({[tert-Butyl(dimethyl)silyl]oxy}methyl)4,5-dihydroisoxazol-3-yl]-1,1'-biphenyl-4-yl}-5-(1H-1,2,3-triazol-1-ylmethyl)-1,3-oxazolidin-2-one

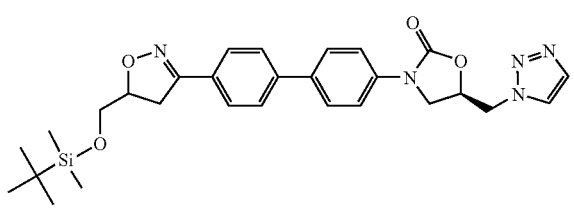

5-({[tert-Butyl(dimethyl)silyl]oxy}methyl)-3-[4-(trimethylstannyl)phenyl]-4,5-dihydroisoxazole (0.5 g, 1.1 mmol), (5R)-3-(4-iodophenyl)-5-(1H-1,2,3-triazol-1-ylmethyl)-1,3-oxazolidin-2-one (0.49 g, 1.32 mmol), and tri-2-furylphosphine (0.051 g, 0.22 mmol) were dissolved in 1,4-dioxane (6 ml) and degassed three times. Tris(dibenzylideneacetone)palladium (0) (0.1 g, 0.11 mmol) was added and the solution was degassed three times. The solution was stirred and heated to 90° C. for 18 hours. The mixture was concentrated in vacuo and then purified by silica flash chromatography with 5-10% methanol in dichloromethane as eluent giving 0.24 g desired product.

MS (ESP) 534.42 (MH+) for $C_{28}H_{35}N_5O_4Si$ $^1$HNMR (DMSO-$d_6$) δ: 0.06 (d, 6H); 0.83 (s, 9H); 3.22 (dd, 1H); 3.46 (m, 1H); 3.73 (dd, 2H); 4.80 (overlapping m, 4H); 5.16 (m, 2H); 7.35 (s, 1H); 7.60 (d, 1H); 7.75 (m, 7H); 8.19 (m, 1H).

Example 38

N-[((5S)-3-{2-Fluoro-4'-[5-(1H-1,2,3-triazol-1-ylmethyl)-4,5-dihydroisoxazol-3-yl]-1,1'-biphenyl-4-yl}-2-oxo-1,3-oxazolidin-5-yl)methyl]acetamide

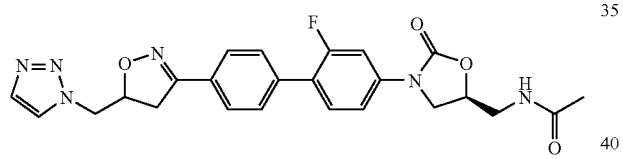

1-({3-[4-(Trimethylstannyl)phenyl]-4,5-dihydroisoxazol-5-yl}methyl)-1H-1,2,3-triazole (0.62 g, 1.58 mmol), N-{[(5S)-3-(3-fluoro-4-iodophenyl)-2-oxo-1,3-oxazolidin-5-yl]methyl}acetamide (0.5 g, 1.32 mmol) and tri-2-furylphosphine (0.08 g, 0.34 mmol) were dissolved in 1,4-dioxane (6 ml) and degassed three times. Tris(dibenzylideneacetone)palladium (0) (0.16 g, 0.18 mmol) was added and the solution was degassed three times. The solution was stirred and heated to 90° C. for 18 hours. The mixture was concentrated in vacuo and then purified by silica flash chromatography with 5-10% methanol in dichloromethane as eluent giving 0.20 g desired product.

MS (ESP) 479.32 (MH+) for $C_{24}H_{23}FN_6O_4$ $^1$HNMR (DMSO-$d_6$) δ: 1.85 (s, 3H); 3.36 (overlapping m, 1H); 3.44 (t, 2H); 3.63 (m, 1H); 3.80 (m, 1H); 4.18 (t, 1H); 4.67 (m, 2H); 4.77 (m, 1H); 5.19 (m, 1H); 7.44 (dd, 1H); 7.69 (m, 7H); 8.16 (s, 1H); 8.25 (t, 1H).

Example 39

(5R)-3-{4'-[5-(Hydroxymethyl)-4,5-dihydroisoxazol-3-yl]-1,1'-biphenyl-4-yl}-5-[(4-methyl-1H-1,2,3-triazol-1-yl)methyl]-1,3-oxazolidin-2-one

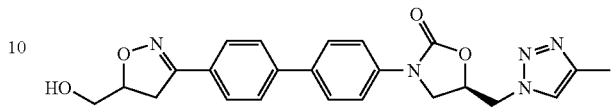

(5R)-3-{4'-[5-({[tert-Butyl(dimethyl)silyl]oxy}methyl)-4,5-dihydroisoxazol-3-yl]-1,1'-biphenyl-4-yl}-5-[(4-methyl-1H-1,2,3-triazol-1-yl)methyl]-1,3-oxazolidin-2-one (0.2 g, 0.37 mmol) was dissolved in THF (5 ml) at 25° C. Tetrabutylammoniumfluoride.3H$_2$O (0.11 g, 0.40 mmol) was added as a solid and the reaction was stirred at 25° C. for 1.5 hours. The mixture was then diluted with ethyl acetate (50 ml) and poured into water. The layers were separated and the aqueous layer was extracted three times with ethyl acetate (3×50 ml). The organic layers were combined, dried over sodium sulfate and concentrated in vacuo. The resulting yellow oil was purified by silica flash chromatography with 5-10% methanol in dichloromethane as eluent, giving 0.025 g desired product.

MS (ESP) 434.32 (MH+) for $C_{23}H_{23}N_5O_4$ $^1$HNMR (DMSO-$d_6$) δ: 2.24 (s, 3H); 3.21 (dd, 1H); 3.40 (m, 1H); 3.53 (m, 1H); 3.94 (dd, 1H); 4.29 (t, 1H); 4.72 (overlapping m, 1H); 4.77 (d, 2H); 5.00 (t, 1H); 5.12 (m, 1H); 7.60 (d, 2H); 7.75 (m, 7H); 7.88 (s, 1H).

Example 40

(5R)-3-{4'-[5-(Hydroxymethyl)-4,5-dihydroisoxazol-3-yl]-1,1'-biphenyl-4-yl}-5-(1H-1,2,3-triazol-1-ylmethyl)-1,3-oxazolidin-2-one

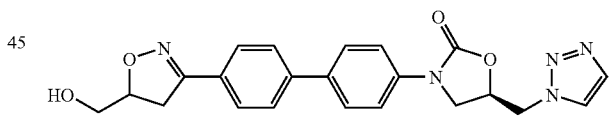

(5R)-3-{4'-[5-({[tert-Butyl(dimethyl)silyl]oxy}methyl)-4,5-dihydroisoxazol-3-yl]-1,1'-biphenyl-4-yl}-5-(1H-1,2,3-triazol-1-ylmethyl)-1,3-oxazolidin-2-one (0.24 g, 0.45 mmol) was dissolved in THF (5 ml) at 25° C. Tetrabutylammoniumfluoride.3H$_2$O (0.138 g, 0.495 mmol) was added as a solid and the reaction was stirred at 25° C. for 1.5 hours. The mixture was then diluted with ethyl acetate (50 ml) and poured into water. The layers were separated and the aqueous layer was extracted three times with ethyl acetate (3×50 ml). The organic layers were combined, dried over sodium sulfate and concentrated in vacuo. The resulting yellow oil was purified by silica flash chromatography with 5-10% methanol in dichloromethane as eluent, giving 0.05 g desired product.

MS (ESP) 420.30 (MH+) $C_{22}H_{21}N_5O_4$

¹HNMR (DMSO-d₆) δ: 3.21 (dd, 1H); 3.42 (m, 2H); 3.53 (m, 1H); 3.95 (dd, 1H); 4.30 (t, 1H); 4.73 (m, 1H); 4.87 (d, 2H); 4.99 (t, 1H); 5.16 (m, 1H); 7.59 (d, 1H); 7.75 (m, 8H); 8.19 (s, 1H).

Example 41

N-{[(5S,5'RS)-3-(2-Fluoro-4'-{5-[(4-methyl-1H-1,2,3-triazol-1-yl)methyl]-4,5-dihydroisoxazol-3-yl}-1,1'-biphenyl-4-yl)-2-oxo-1,3-oxazolidin-5-yl]methyl}acetamide

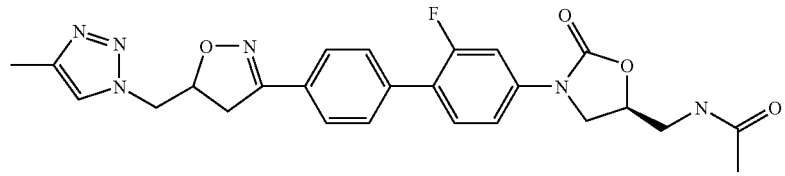

(5S)-N-[3-(3-Fluoro-4-iodo-phenyl)-2-oxo-oxazolidin-5-ylmethyl]acetamide (336 mg, 1.00 mM), tris(dibenzylidineacetone)dipalladium (0) (36 mg, 0.039 mM) and tri-2-furylphosphine (19 mg, 0.082 mM) were placed in a flask. The solids were degassed and placed under argon. Anhydrous N-methylpyrrolidinone (5 ml) was added, and the resulting purple solution became brown within minutes. 4-Methyl-1-({3-[4-(trimethylstannyl)phenyl]-4,5-dihydroisoxazol-5-yl}methyl)-1H-1,2,3-triazole (486 mg, 1.20 mM) was added (and the solution degassed again). The solution was heated at 90° C. for approximately 24 hours. The reaction mixture was filtered through celite and water added to the filtrate to precipitate the crude product. The crude material was purified by reverse phase chromatography using an ether-linked phenyl phase column with polar endcapping (250×50 mm, 10μ). The mobile phase was water with 0.1% trifluoroacetic acid/acetonitrile with 0.1% trifluoroacetic acid. The organic phase was increased from 20-95% over 35 minutes with a flow rate of 100 ml/min. Sample collection was monitored at 254 nm. A total of 97 mg of the desired product was obtained.

MS (ESP): 493 (M+1) for C₂₅H₂₅FN₆O₄

NMR (DMSO-d₆) δ: 1.84 (s, 3H); 2.22 (s, 3H); 3.30 (dd, 1H); 3.43-3.45 (m overlapping with water, 2H); 3.62 (dd, 1H); 3.79 (dd, 1H); 4.18 (t, 1H); 4.54-4.62 (m, 2H); 4.77 (m, 1H); 5.13 (m, 1H); 7.43 (dd, 1H); 7.60-7.74 (m, 6H); 7.86 (s, 1H); 8.26 (t, 1H).

The intermediate for this compound was prepared as follows:

4-Methyl-1-({3-[4-(trimethylstannyl)phenyl]-4,5-dihydroisoxazol-5-yl]methyl)-1H-1,2,3-triazole

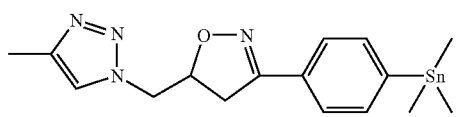

1-{[3-(4-Bromo-phenyl)-4,5-dihydro-isoxazol-5-yl]methyl}-4-methyl-1H-1,2,3-triazole (1.78 g, 5.55 mM), was dissolved in 1,4-dioxane (20 ml). Bis(triphenylphosphine)palladium(II) chloride (195 mg, 0.28 mM) was added and the solution was degassed. Hexamethylditin (2.00 g, 6.10 mM) was added and the resulting solution was heated at 90° C. for approximately 20 hours. The reaction mixture was adsorbed onto silica gel and chromatographed with 50% ethyl acetate/hexanes to give 1.83 g of the desired product.

MS (APCI): 405, 406, 407 (M+1) for C₁₆H₂₂N₄OSn

NMR (DMSO-d₆) δ: 0.28 (s, 9H); 2.21 (s, 3H); 3.23 (dd, 1H); 3.56 (dd, 1H); 4.54-4.57 (m, 2H); 5.09 (m, 1H); 7.56 (s, 4H); 7.84 (s, 1H).

Example 42

(5R,5'RS)-3-(2-Fluoro-4'-{5-[(4-methyl-1H-1,2,3-triazol-1-yl)methyl]-4,5-dihydroisoxazol-3-yl}-1,1'-biphenyl-4-yl)-5-(hydroxymethyl)-1,3-oxazolidin-2-one

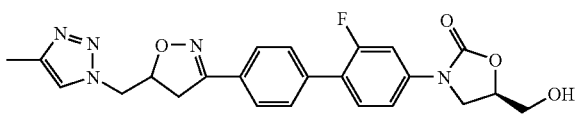

(5R,5'RS)-5-({[tert-Butyl(dimethyl)silyl]oxy}methyl)-3-(2-fluoro-4'-{5-[(4-methyl-1H-1,2,3-triazol-1-yl)methyl]-4,5-dihydroisoxazol-3-yl}-1,1'-biphenyl-4-yl)-1,3-oxazolidin-2-one (90 mg, 0.16 mM) was dissolved in tetrahydrofuran (5 ml) and a 1 M solution of tetrabutylammonium fluoride in THF (0.2 ml, 0.19 mM) was added. After 30 min, the reaction mixture was poured into ethyl acetate and washed with water. The phases were separated and the organic phase was concentrated under vacuum. The crude product was purified by reverse phase chromatography using a C8 column (100×21.2 mm, 5u). The mobile phase was water with 0.1% trifluoroacetic acid/acetonitrile with 0.1% trifluoroacetic acid. The organic phase was increased from 20-50% over 14 minutes with a flow rate of 20 ml/min, and monitored a wavelength of 280 nm, to give 59 mg of the title product.

MS (APCI): 452 (M+1) for C₂₃H₂₂FN₅O₃

NMR (DMSO-d₆) δ: 2.22 (s, 3H); 3.30 (dd, 1H); 3.56-3.76 (overlapping m, 3H); 3.86 (dd, 1H); 4.14 (t, 1H); 4.54-4.62 (m, 2H); 4.74 (m, 1H); 5.13 (m, 1H); 7.47 (dd, 1H); 7.60-7.67 (m, 4H); 7.72 (d, 2H); 7.83 (s, 1H).

The intermediate for this compound was prepared as follows:

(5R, 5'RS)-5-({[tert-Butyl(dimethyl)silyl]oxy}methyl)-3-(2-fluoro-4'-{5-[(4-methyl-1H-1,2,3-triazol-1-yl)methyl]-4,5-dihydroisoxazol-3-yl}-1,1'-biphenyl-4-yl)-1,3-oxazolidin-2-one

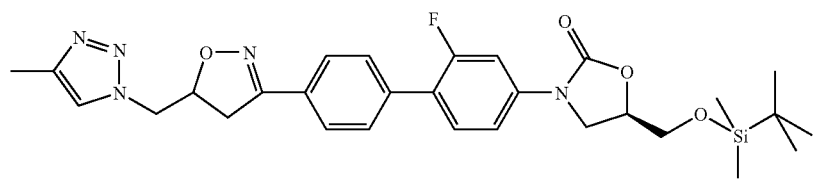

The procedure of Example 41 was used, but starting from (5R)-5-({[tert-butyl(dimethyl)silyl]oxy}methyl)-3-(3-fluoro-4-iodophenyl)-1,3-oxazolidin-2-one (180 mg, 0.40 mM), and 4-methyl-1-({3-[4-(trimethylstannyl)phenyl]-4,5-dihydroisoxazol-5-yl}methyl)-1H-1,2,3-triazole (194 mg, 0.48 mM). The reaction mixture was filtered through celite. Water was added to precipitate the product which was adsorbed onto silica gel and chromatographed with 50% ethyl acetate/dichloromethane to give 95 mg of the title product.

MS (APCI): 566 (M+1) for $C_{29}H_{36}FN_5O_4Si$

NMR (DMSO-$d_6$) δ: 0.03 (s, 6H); 0.75 (s, 9H); 2.17 (s, 3H); 3.24 (overlapping with solvent, 1H); 3.57 (dd, 1H); 3.70-3.86 (overlapping m, 3H); 4.12 (t, 1H); 4.49-4.57 (m, 2H); 4.76 (m, 1H); 5.07 (m, 1H); 7.41, (dd, 1H); 7.55-7.68 (m, 6H); 7.81 (s, 1H).

Example 43

(5R,5'RS)-3-{2-Fluoro-4'-[5-(hydroxymethyl)-4,5-dihydroisoxazol-3-yl]-1,1'biphenyl-4-yl}-5-(1H-1,2,3-triazol-1-ylmethyl)-1,3-oxazolidin-2-one

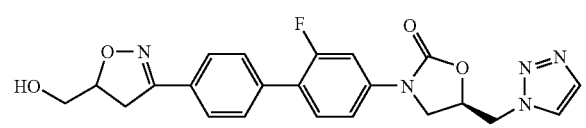

Using essentially the same procedure as described for Example 41, but starting from (5R)-3-(3-fluoro-4-iodophenyl)-5-(1H-1,2,3-triazol-1-ylmethyl)-1,3-oxazolidin-2-one (412 mg, 1.06 mM), and 5-({[tert-butyl(dimethyl)silyl]oxy}methyl)-3-[4(trimethylstannyl)phenyl]-4,5-dihydroisoxazole (579 mg, 1.27 mM) gave the product as a silyl ether. Purification by reverse phase chromatography using water with 0.1% trifluoroacetic acid/acetonitrile with 0.1% trifluoroacetic acid as mobile phase concomitantly removed the silyl protecting group to give 84 mg of the title product.

MS (ESP): 438 (M+1) for $C_{22}H_{20}FN_5O_4$

NMR (DMSO-$d_6$) δ: 3.24 (dd, 1H); 3.45 (dd, 1H); 3.49-3.59 (m, 2H); 3.97 (m, 1H); 4.31 (t, 1H); 4.76 (m, 1H); 4.88-4.89 (m, 2H); 5.02 (m, 1H); 5.21 (m, 1H); 7.41 (d, 1H); 7.56-7.66 (overlapping m, 4H); 7.76-7.79 (overlapping m, 3H); 8.2 (s, 1H).

Example 44

N-[((5S)-3-{4'-[(5R)-5-(Hydroxymethyl)-4,5-dihydroisoxazol-3-yl]-1,1'-biphenyl-4-yl}-2-oxo-1,3-oxazolidin-5-yl)methyl]acetamide

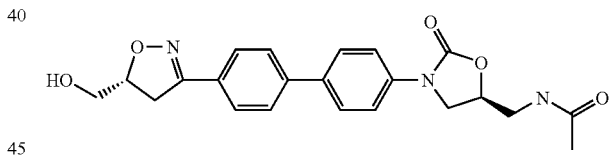

A solution of tetrabutylammonium fluoride in THF (1M, 0.69 ml, 0.69 mM) was added to a solution of N-[((5S)-3-{4'-[(5R)-5-({[tert-butyl(dimethyl)silyl]oxy}methyl)-4,5-dihydroisoxazol-3-yl]-1,1'-biphenyl-4-yl}-2-oxo-1,3-oxazolidin-5-yl)methyl]acetamide (300 mg, 0.57 mM) in THF (5 ml). After approximately 2 hours, ethyl acetate was added and the resulting suspension was filtered. The filter cake was washed with water and ethyl acetate to give 140 mg of the title product.

MS (ESP): 410 (M+1) for $C_{22}H_{23}N_3O_4$

NMR (DMSO-$d_6$) δ: 1.84 (s, 3H); 3.22 (dd, 1H); 3.41-3.49 (m, 3H); 3.50-3.53 (m, 2H); 3.79 (dd, 1H); 4.17 (t, 1H); 4.70-4.77 (m, 2H); 5.00 (m, 1H); 7.64-7.78 (overlapping m, 8H); 8.26 (t, 1H).

The intermediates for this compound were prepared as follows:

N-[((5S)-3-{4'-[(5R)-5-({[tert-Butyl(dimethyl)silyl]oxy}methyl)-4,5-dihydroisoxazol-3-yl]-1,1'-biphenyl-4-yl}-2-oxo-1,3-oxazolidin-5-yl)methyl]acetamide

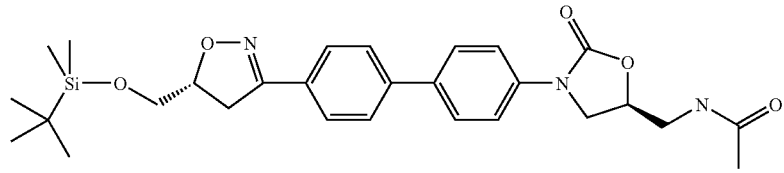

The procedure of Example 41, but starting from N-({(5S)-2-oxo-3-[4-(trimethylstannyl)phenyl]-1,3-oxazolidin-5-yl}methyl)acetamide (476 mg, 1.20 mM) and (5R)-3-(4-bromophenyl)-5-({[tert-butyl(dimethyl)silyl]oxy}methyl)-4,5-dihydroisoxazole (370 mg, 1.00 mM) was used to give the desired product after 7 hours at 90° C. Purification by chromatography on silica gel using 90% ethyl acetate/hexanes gave 398 mg of the title product.

MS (APCI): 524 (M+1) for $C_{28}H_{37}N_3O_5Si$

NMR (DMSO-$d_6$) δ: 0.04 (s, 3H); 0.06 (s, 3H); 0.83 ((s, 9H); 1.84 (s, 3H); 3.20 (dd, 1H); 3.40-3.47 (m, 3H); 3.68-3.81 (overlapping m, 3H); 4.17 (m, 1H); 4.72-4.80 (m, 2H); 7.64-7.78 (m, 8H); 8.26 (t, 1H).

(5R)-3-(4-Bromophenyl)-5-({[tert-butyl(dimethyl)silyl]oxy}methyl)-4,5-dihydroisoxazole

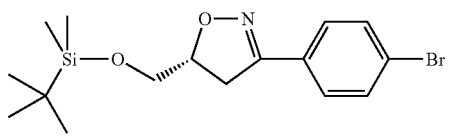

The preparation of (5R)-3-(4-bromophenyl)-5-({[tert-butyl(dimethyl)silyl]oxy}methyl)-4,5-dihydroisoxazole from (SR)-[3-(4-bromophenyl)-4,5-dihydroisoxazol-5-yl]methanol was the same as that shown in Example 6 for the racemate. The title product was obtained in 99% yield. The analytical data were also indistinguishable from those of the racemate.

Racemic [3-(4-bromophenyl)-4,5-dihydroisoxazol-5-yl]methanol mixture was separated using a Chiracel OJ column (500 mm×50 mm, 10μ) using 30% isopropanol in hexane at a 100 mL/min flow rate. The separation was monitored at 254 nm. The first peak was assigned the R configuration. [α$_D$]=−126.8° The assignment of absolute stereochemistry was made by comparison of the sign of rotation and the order of elution of analogous compounds (D. P. Curran et al., *Tet. Letters*, 1988, 29(29), 3555-3558; C. Ticozzi and A. Zanarotti, *Tet. Letters*, 1994, 35(40), 7421-7424).

Example 45

N-[((5S)-3-{4'-[(5S)-5-(Hydroxymethyl)-4,5-dihydroisoxazol-3-yl]-1,1'-biphenyl-4-yl}-2-oxo-1,3-oxazolidin-5-yl)methyl]acetamide

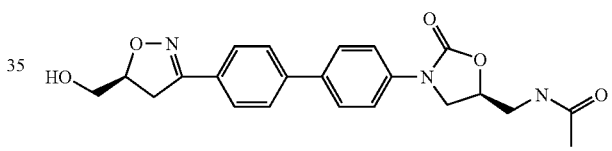

The preparation of the title compound was analogous to that shown in Example 44 except N-[((5S)-3-{4'-[(5S)-5-({[tert-butyl(dimethyl)silyl]oxy}methyl)-4,5-dihydroisoxazol-3-yl]-1,1'-biphenyl-4-yl}-2-oxo-1,3-oxazolidin-5-yl)methyl]acetamide (200 mg, 0.38 mM) was used as starting material. The crude product was recrystallized from N-methyl-pyrrolidinone and water to give 41 mg of the title product.

MS (ESP): 410 (M+1) for $C_{22}H_{23}N_3O_4$

NMR (DMSO-$d_6$) δ: 1.84 (s, 3H); 3.22 (dd, 1H); 3.41-3.49 (m, 3H); 3.50-3.53 (m, 2H); 3.79 (dd, 1H); 4.17 (t, 1H); 4.70-4.77 (m, 2H); 5.00 (br s, 1H); 7.64-7.78 (overlapping m, 8H); 8.26 (t, 1H).

The intermediates for this compound were prepared as follows:

N-[((5S)-3-4'-[(5S)-5-({[tert-Butyl(dimethyl)silyl]oxy}methyl)-4,5-dihydroisoxazol-3-yl]-1,1'-biphenyl-4-yl}-2-oxo-1,3-oxazolidin-5-yl)methyl]acetamide

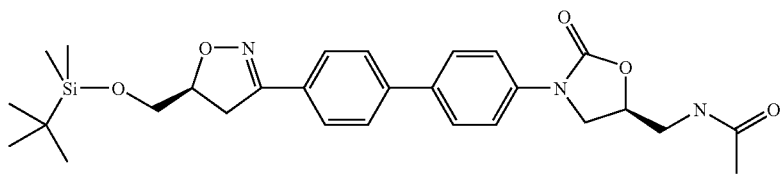

The procedure of Example 41, but starting from N-({(5S)-2-oxo-3-[4-(trimethylstannyl)phenyl]-1,3-oxazolidin-5-yl}methyl)acetamide (476 mg, 1.20 mM) and (5S)-3-(4-bromophenyl)-5-({[tert-butyl(dimethyl)silyl]oxy}methyl)-4,5-dihydroisoxazole (370 mg, 1.00 mM) was used to give the desired product after approximately 20 hours at 90° C. Purification by chromatography on silica gel using 90% ethyl acetate/hexanes gave 284 mg of the title product.

MS (APCI): 524 (M+1) for $C_{28}H_{37}N_3O_5Si$

NMR (DMSO-$d_6$) δ: 0.04 (s, 3H); 0.06 (s, 3H); 0.83 ((s, 9H); 1.84 (s, 3H); 3.26 (dd, 1H); 3.40-3.47 (m, 3H); 3.70-3.81 (overlapping m, 3H); 4.17 (t, 1H); 4.74-4.77 (m, 2H); 7.64-7.78 (m, 8H); 8.26 (t, 1H).

(5S)-3-(4-Bromophenyl)-5-({[tert-butyl(dimethyl)silyl]oxy}methyl)-4,5-dihydroisoxazole

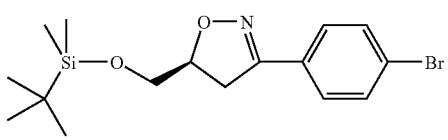

The preparation of (5S)-3-(4-bromophenyl)-5-({[tert-butyl(dimethyl)silyl]oxy}methyl)-4,5-dihydroisoxazole from (5S)-3-(4-bromophenyl)-4,5-dihydroisoxazol-5-yl]methanol was the same as that shown in Example 6 for the racemate. The title product was obtained in 97% yield. The analytical data were also indistinguishable from those of the racemate.

Racemic [3-(4-bromophenyl)-4,5-dihydroisoxazol-5-yl]methanol mixture was separated using a Chiracel OJ column (500 mm×50 mm, 10μ) using 30% isopropanol in hexane at a 100 mL/min flow rate. The separation was monitored at 254 nm. The second peak was assigned the S configuration. [$α_D$] =+103.8.

The assignment of absolute stereochemistry was made by comparison of the sign of rotation and the order of elution of analogous compounds (D. P. Curran et al., *Tet. Letters*, 1988, 29(29), 3555-3558; C. Ticozzi and A. Zanarotti, *Tet. Letters*, 1994, 35(40), 7421-7424).

Example 46

(5S)-3-(2-Fluoro-4'-5-[(4-methyl)-1H-1,2,3-triazol-1-yl)methyl]-4,5-dihydroisoxazol-3-yl}-1,1'-biphenyl-4-yl)-5-[(isoxazol-3-ylamino)methyl]-1,3-oxazolidinon-2-one

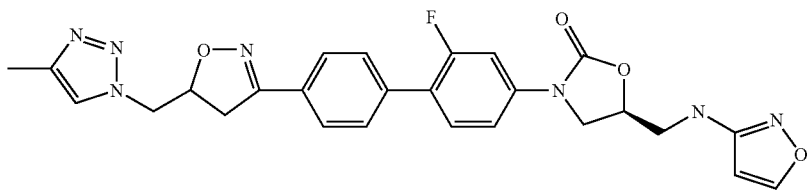

To a solution of tert-butyl N-[(5R)-3-(2-fluoro-4'-{5-[(4-methyl)-1H-1,2,3-triazol-1-yl)methyl]-4,5-dihydroisoxazol-3-yl}-1,1'-biphenyl-4-yl)-2-oxo-1,3-oxazolidin-5-yl]methyl N-(isoxazol-3-yl) carbamate (41 mg, 0.067 mM) in dichloromethane (1 ml) was added trifluoroacetic acid (0.5 ml). After approximately 30 min, the solution was concentrated under vacuum to give 33 mg of the title compound.

MS (ESP): 518 (M+1) for $C_{26}H_{24}FN_7O_4$

NMR (DMSO-$d_6$) δ: 2.23 (s, 3H); 3.30(dd, 1H); 3.43-3.50 (m, 2H); 3.62 (dd, 1H); 3.87 (dd, 1H); 4.21 (t, 1H); 4.54-4.62 (m, 2H); 4.92 (m, 1H); 5.13 (m, 1H); 6.01 (s, 1H); 7.43-7.49 (m, 2H); 7.60-7.64 (m, 3H); 7.23 (d, 2H); 7.87 (s, 1H); 8.39 (s, 1H).

The intermediate for this compound was prepared as follows:

tert-Butyl N-[(5R)-3-(2-fluoro-4'-{5-[(4-methyl)-1H-1,2,3-triazol-1-yl)methyl]-4,5-dihydroisoxazol-3-yl}-1,1'-biphenyl-4-yl)-2-oxo-1,3-oxazolidin-5-yl]methyl N-(isoxazol-3-yl)carbamate

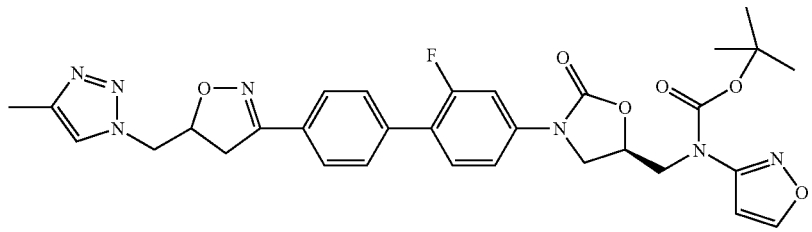

The procedure of Example 41 but starting from 4-methyl-1-({3-[4-(trimethylstannyl)phenyl]-4,5-dihydroisoxazol-5-yl}methyl)-1H-1,2,3-triazole (729 mg, 1.80 mM) and N-(5R)-[3-(3-fluoro-4-iodo-phenyl)-2-oxo-1,3-oxazolidin-5-ylmethyl]-N-isoxazol-3-yl carbamic acid tert-butyl ester (755 mg, 1.50 mM) was used. A total of 269 mg of the title product was obtained after purification by reverse phase chromatography using an ether-linked phenyl phase column with polar endcapping (250×50 mm, 10µ). The mobile phase was water with 0.1% trifluoroacetic acid/acetonitrile with 0.1% trifluoroacetic acid. The organic phase was increased from 20-95% over 35 minutes with a flow rate of 100 ml/min and sample collection was monitored at 280 nm.

MS (ESP): 618 (M+1) for $C_{31}H_{32}FN_7O_6$

NMR (DMSO-$d_6$) δ: 1.51 (s, 9H); 2.08 (s, 3H); 3.32 (dd, 1H); 3.64 (dd, 1H); 3.93 (dd, 1H); 4.02 (dd, 1H); 4.27-4.33 (m, 2H); 4.56-4.63 (m, 2H); 5.06 (m, 1H); 5.15 (m, 1H); 6.89 (s, 1H); 7.48 (dd, 1H); 7.62-7.75 (overlapping m, 6H); 7.75 (s, 1H); 8.55 (d, 1H).

Example 47

[3-(4'-{(5S)-5-[(Acetylamino)methyl]-2-oxo-1,3-oxazolidin-3-yl}-1,1'-biphenyl-4-yl)-4,5-dihydroisoxazol-5-yl]methyl di-tert-butyl phosphate

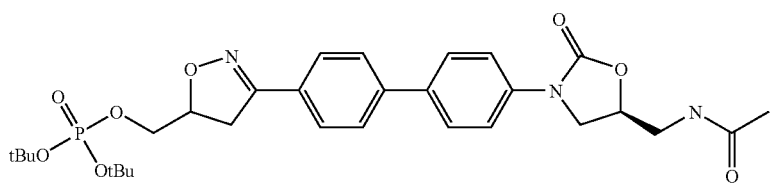

[3-(4-Bromophenyl)-4,5-dihydroisoxazol-5-yl]methyl di-tert-butyl phosphate (0.25 g, 0.55 mmol), N-({(5S)-2-oxo-3-[4-(trimethylstannyl)phenyl]-1,3-oxazolidin-5-yl}methyl)acetamide (0.25 g, 0.66 mmol), tri-2-furylphosphine (0.026 g, 0.11 mmol) and tris(dibenzylideneacetone)palladium (0) (0.05 g, 0.55 mmol) were dissolved in 1,4-dioxane (5 ml) and degassed three times. The mixture was heated to 90° C. and stirred for 5 hr, then stirred at 25° C. for 12 hours. The solution was concentrated in vacuo and purified by silica flash chromatography with 5-10% methanol in dichloromethane as eluent giving 0.12 g of the desired product as a yellowish white foam.

MS (ESP) 490.21 [(M+3H$^+$–(2t–Bu)](calculated mass=489.43) and 602.35 (MH+) for $C_{30}H_{40}N_3O_8P$ $^1$HNMR (DMSO-$d_6$) δ: 1.4 (d, 18H); 1.84 (s, 3H); 3.25 (dd, 1H); 3.44 (t, 2H); 3.57 (dd, 1H); 3.81 (dd, 1H); 3.99 (m, 2H); 4.18 (t, 1H); 4.75 (m, 1H); 4.94 (m, 1H); 7.65 (d, 2H); 7.76 (m, 6H); 8.26 (t, 1H).

The phosphate intermediate for Example 47 was prepared as follows:

[3-(4-Bromophenyl)-4,5-dihydroisoxazol-5-yl]methyl di-tert-butyl phosphate

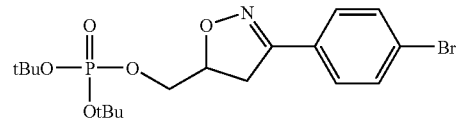

[3-(4-Bromophenyl)-4,5-dihydroisoxazol-5-yl]methanol (2.5 g, 9.8 mmol) was dissolved in dichloromethane (100 ml). To this solution, di-tert-butyl-N,N-diethylphosphoroamidite (3.3 ml, 11.7 mmol) and 1H-tetrazole (1.2 g, 17.6 mmol) were added sequentially. After 1.5 h stirring at room temperature, the solution was cooled to 0° C. and m-chloroperbenzoic acid (70%; 3.6 g, 14.7 mmol) was added. After 1.5 h the reaction was warmed to room temperature; a sodium bisulfite solution was added and the mixture stirred about 5 min. After diluting with dichloromethane, the aqueous layer was extracted with dichloromethane (2×), and the combined organics were washed with saturated sodium bicarbonate solution, brine, and dried over magnesium sulfate. The crude residue was purified by chromatography on silica gel using 0-5% methanol in dichloromethane as the eluent, resuliting in 4.1 g of the desired product.

MS (ESP) 336.06 (M–2tBu+3H$^+$)(calc=336.08) for $C_{18}H_{27}BrNO_5P$.

$^1$H-NMR (DMSO-d$_6$) δ: 1.38 (d, 18H); 3.22 (dd, 1H); 3.53 (dd, 1H); 3.98 (m, 2H); 4.93 (m, 1H); 7.64 (q, 4H).

Example 48

[3-(4'-{(5S)-5-[(Acetylamino)methyl]-2-oxo-1,3-oxazolidin-3-yl}-1,1'-biphenyl-4-yl)-4,5-dihydroisoxazol-5-yl]methyl dihydrogen phosphate

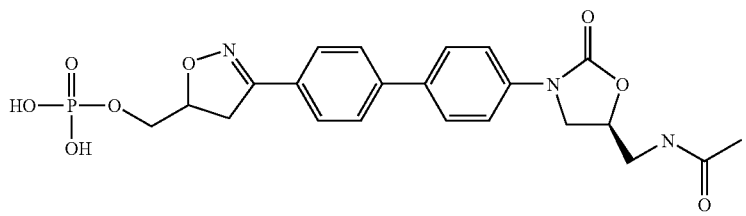

[3-(4'-{(5S)-5-[(Acetylamino)methyl]-2-oxo-1,3-oxazolidin-3-yl}-1,1'-biphenyl-4-yl)-4,5-dihydroisoxazol-5-yl]methyl di-tert-butyl phosphate (95 mg, 0.16 mmol) was dissolved in dichloromethane (1 ml) and trifluoroacetic acid (0.1 ml) was added. The solution was stirred for 1 h at ambient temperature, then concentrated in vacuo. Dichloromethane was added and the volatiles were removed in vacuo. This was repeated twice with dichloromethane and five times with diethyl ether. A pale yellow solid was obtained (78 mg) corresponding to the desired product.

MS (ESP) 490.21 (MH+) for $C_{22}H_{24}N_3O_8P$.

$^1$H-NMR (DMSO-d$_6$) δ: 1.84 (s, 3H); 3.28 (dd, 1H); 3.44 (t, 2H); 3.54 (dd, 1H); 3.80 (dd, 1H); 3.94 (m, 2H); 4.18 (t, 1H); 4.75 (m, 1H); 4.91 (m, 1H); 7.66 (d, 2H); 7.76 (m, 6H); 8.26 (t, 1H).

[3-(4'-{(5S)-5-[(Acetylamino)methyl]-2-oxo-1,3-oxazolidin-3-yl}-1,1'-biphenyl-4-yl)-4,5-dihydroisoxazol-5-yl]methyl disodium phosphate

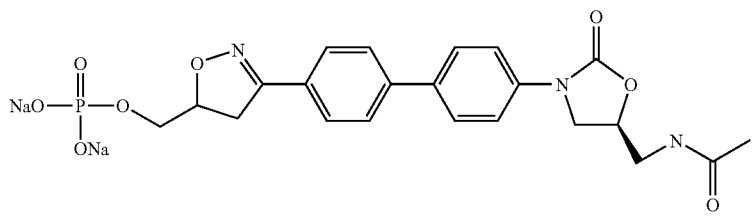

[3-(4'-{(5S)-5-[(Acetylamino)methyl]-2-oxo-1,3-oxazolidin-3-yl}-1,1'-biphenyl-4-yl)-4,5-dihydroisoxazol-5-yl] methyl dihydrogen phosphate (78 mg) was suspended in water (15 ml). The pH was slowly adjusted from ≈pH 3.5 to ≈pH 7.5 using a solution of saturated sodium bicarbonate. The water was removed by lyophilization resulting in 130 mg white solid (desired product+excess sodium bicarbonate).

Example 49

N-{[(5S)-3-(4-{5-[5-(Hydroxymethyl)-4,5-dihydroisoxazol-3-yl]thien-2-yl}phenyl)-2-oxo-1,3-oxazolidin-5-yl]methyl}acetamide

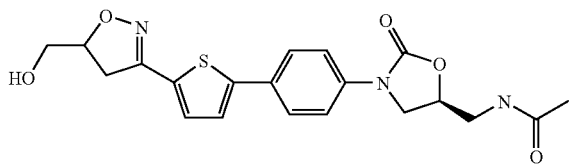

N-({(5S)-2-Oxo-3-[4-(trimethylstannyl)phenyl]-1,3-oxazolidin-5-yl}methyl)acetamide (500 mg, 1.26 mM), [3-(5-bromothien-2-yl)-4,5-dihydroisoxazol-5-yl]methanol (330 mg, 1.26 mM), tris(dibenzylideneacetone)dipalladium (0)-chloroform adduct (130 mg, 0.126 mM) and tri-2-furylphosphine (58 mg, 0.252 mM) were placed in a flask. The solids were degassed and placed under nitrogen. Anhydrous dioxane (10 ml) was added and the suspension was heated at 90° C. for 16 hours. The reaction mixture was cooled and the solvent was evaporated. The residue was chromatographed on silica gel eluting with 5% methanol in dichloromethane to give the title compound (220 mg).

MS (APCI): 416 (M+1) for $C_{20}H_{21}N_3O_5S$

NMR (DMSO-d$_6$) δ: 1.84 (s, 3H); 3.18-3.51 (m, 6H); 3.80 (t, 1H); 4.15 (t, 1H); 4.73 (m, 2H); 5.08 (m, 1H); 7.35 (d, 1H); 7.51 (d, 1H); 7.59 (d, 2H); 7.75 (d, 2H); 8.25 (t, 1H).

Example 50

(5R)-3-(4-{5-[5-(Hydroxymethyl)-4,5-dihydroisox-azol-3-yl]thien-2-yl}phenyl)-5-(1H-1,2,3-triazol-1-ylmethyl)-1,3-oxazolidin-2-one

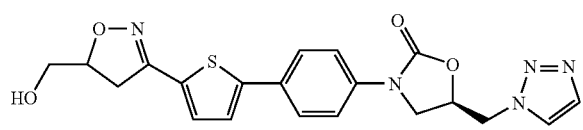

(5R)-3-(4-Iodophenyl)-5-(1H-1,2,3-triazol-1-ylmethyl)-1,3-oxazolidin-2-one (214 mg, 0.58 mM), {3-[5-(trimethylstannyl)thien-2-yl]-4,5-dihydroisoxazol-5-yl}methanol (200 mg, 0.58 mM), tris(dibenzylideneacetone)dipalladium (0)-chloroform adduct (60 mg, 0.058 mM) and tri-2-furylphosphine (27 mg, 0.116 mM) were placed in a flask. The solids were degassed and placed under nitrogen. Anhydrous dioxane (5 ml) was added and the suspension was heated at 90° C. for 16 hours. The reaction mixture was cooled and the solvent was evaporated. The residue was chromatographed on silica gel eluting with 5% methanol in dichloromethane to give the title compound (100 mg).

MS (APCI): 426 (M+1) for $C_{20}H_{19}N_5O_4S$

NMR (DMSO-$d_6$) δ: 3.18-3.57 (m, 5H); 3.94 (dd, 1H); 4.31 (t, 1H); 4.75 (m, 1H); 4.84 (d, 2H); 5.16 (m, 1H); 7.35 (d, 1H); 7.50 (d, 1H); 7.53 (d, 2H); 7.71 (d, 2H); 7.76 (s, 1H); 8.18 (s, 1H).

The intermediate for this compound was prepared as follows:

{3-[5-(Trimethylstannyl)thien-2-yl]-4,5-dihydroisoxazol-5-yl}methanol

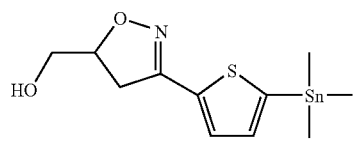

[3-(5-Bromothien-2-yl)-4,5-dihydroisoxazol-5-yl]methanol (3.7 g, 14.10 mM) and bis(triphenylphosphine)palladium (II) chloride (593 mg, 0.847 mM) were placed under nitrogen. Anhydrous dioxane (50 ml) was added and the supension was heated to 90° C. Hexamethylditin (5.00 g, 15.53 mM) was added and the resulting solution was stirred at 90° C. for 16 hours. The solution was cooled and the solvent was evaporated. The residue was chromatographed on silica gel eluting with 5% methanol in dichloromethane to give the desired product (2.5 g).

MS (APCI): 347 (M+1) for $C_{11}H_{17}NO_2SSn$

NMR (DMSO-$d_6$) δ: 0.36 (s, 9H); 3.19 (dd, 1H); 3.40 (dd, 1H); 3.49 (br t, 2H); 4.70 (m, 1H); 4.98 (t, 1H); 7.20 (d, 1H); 7.41 (d, 1H).

Example 51

(5R)-3-(4-{5-[5-(Hydroxymethyl)-4,5-dihydroisox-azol-3-yl]thien-2-yl}phenyl)-5-[(4-methyl-1H-1,2,3-triazol-1-yl)methyl]-1,3-oxazolidin-2-one

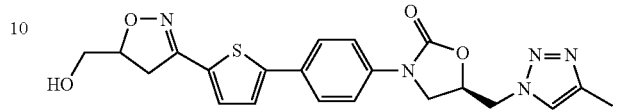

(5R)-3-(4-Iodophenyl)-5-[(4-methyl-1H-1,2,3-triazol-1-yl)methyl]-1,3-oxazolidin-2-one (222 mg, 0.58 mM), {3-[5-(trimethylstannyl)thien-2-yl]4,5-dihydroisoxazol-5-yl}methanol (200 mg, 0.58 mM), tris(dibenzylideneacetone)dipalladium (0)-chloroform adduct (60 mg, 0.058 mM) and tri-2-furylphosphine (27 mg, 0.116 mM) were placed in a flask. The solids were degassed and placed under nitrogen. Anhydrous dioxane (5 ml) was added and the suspension was heated at 90° C. for 16 hours. The reaction mixture was cooled and the solvent was evaporated. The residue was chromatographed on silica gel eluting with 5% methanol in dichloromethane to give the title compound (90 mg).

MS (APCI): 440 (M+1) for $C_{21}H_{21}N_5O_4S$

NMR (DMSO-$d_6$) δ: 2.23 (s, 3H); 3.18-3.56 (m, 4H); 3.91 (dd, 1H); 4.26 (t, 1H); 4.76 (m, 3H); 5.01 (t, 1H); 5.11 (m, 1H); 7.35 (d, 1H); 7.50 (d, 1H); 7.54 (d, 2H); 7.71 (d, 2H); 7.87 (s, 1H).

Example 52

N-{[(5S)-3-(3-Fluoro-4-{5-[5-(hydroxymethyl)-4,5-dihydroisoxazol-3-yl]thien-2-yl}phenyl)-2-oxo-1,3-oxazolidin-5-yl]methyl}acetamide

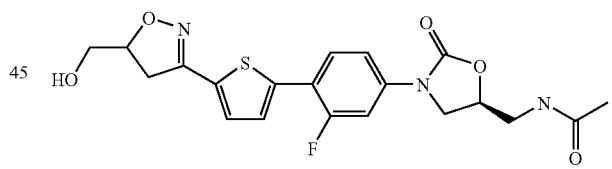

N-{[(5S)-3-(3-Fluoro-4-iodophenyl)-2-oxo-1,3-oxazolidin-5-yl]methyl}acetamide (273 mg, 0.72 mM), {3-[5-(trimethylstannyl)thien-2-yl]-4,5-dihydroisoxazol-5-yl}methanol (250 mg, 0.72 mM), tris(dibenzylideneacetone)dipalladium (0)-chloroform adduct (75 mg, 0.072 mM) and tri-2-furylphosphine (34 mg, 0.145 mM) were placed in a flask. The solids were degassed and placed under nitrogen. Anhydrous dioxane (5 ml) was added and the suspension was heated at 90° C. for 16 hours. The reaction mixture was cooled and the solvent was evaporated. The residue was chromatographed on silica gel eluting with 5% methanol in dichloromethane to give the title compound (180 mg).

MS (APCI): 434 (M+1) for $C_{20}H_{20}N_3O_5SF$

NMR (DMSO-$d_6$) δ: 1.84 (s, 3H); 3.19-3.52 (m, 6H); 3.79 (dd, 1H); 4.17 (t, 1H); 4.76 (m, 2H); 5.01 (m, 1H); 7.41-7.44 (m, 2H); 7.56 (d, 1H); 7.60 (dd, 1H); 7.87 (t, 1H); 8.24 (t, 1H).

Example 53

(5R)-3-(3-Fluoro-4-{5-[5-(hydroxymethyl)-4,5-dihydroisoxazol-3-yl]thien-2-yl}phenyl)-5-(1H-1,2,3-triazol-1-ylmethyl)-1,3-oxazolidin-2-one

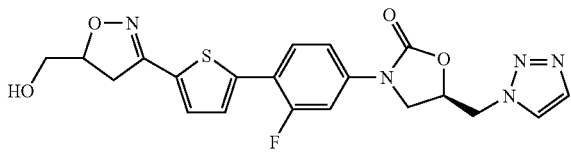

(5R)-3-(3-Fluoro-4-iodophenyl)-5-(1H-1,2,3-triazol-1-ylmethyl)-1,3-oxazolidin-2-one (280 mg, 0.72 mM), {3-[5-(trimethylstannyl)thien-2-yl]-4,5-dihydroisoxazol-5-yl}methanol (250 mg, 0.72 mM), tris(dibenzylideneacetone) dipalladium (0)-chloroform adduct (75 mg, 0.072 mM) and tri-2-furylphosphine (34 mg, 0.145 mM) were placed in a flask. The solids were degassed and placed under nitrogen. Anhydrous dioxane (5 ml) was added and the suspension was heated at 90° C. for 16 hours. The reaction mixture was cooled and the solvent was evaporated. The residue was chromatographed on silica gel eluting with 5% methanol in dichloromethane to give the title compound (170 mg).

MS (APCI): 444 (M+1) for $C_{20}H_{18}N_5O_4SF$

NMR (DMSO-$d_6$) δ: 3.19-3.52 (m, 6H); 3.95 (dd, 1H); 4.31 (t, 1H); 4.78 (m, 1H); 4.87 (d, 2H); 5.09 (m, 1H); 5.20 (m, 1H); 7.36-7.40 (m, 2H); 7.54-7.59 (m, 2H); 7.77 (s, 1H); 7.86 (t, 1H); 8.18 (s, 1H).

Example 54

(5R)-3-(3-Fluoro-4-{5-[5-(hydroxymethyl)-4,5-dihydroisoxazol-3-yl]thien-2-yl}phenyl)-5-[(4-methyl-1H-1,2,3-triazol-1-yl)methyl]-1,3-oxazolidin-2-one

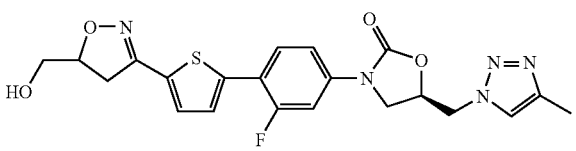

(5R)-3-(3-Fluoro-4-iodophenyl)-5-[(4-methyl-1H-1,2,3-triazol-1-yl)methyl]-1,3-oxazolidin-2-one (232 mg, 0.58 mM), {3-[5-(trimethylstannyl)thien-2-yl]4,5-dihydroisoxazol-5-yl}methanol (200 mg, 0.58 mM), tris(dibenzylideneacetone) dipalladium (0)-chloroform adduct (60 mg, 0.058 mM) and tri-2-furylphosphine (27 mg, 0.116 mM) were placed in a flask. The solids were degassed and placed under nitrogen. Anhydrous dioxane (5 ml) was added and the suspension was heated at 90° C. for 16 hours. The reaction mixture was cooled and the solvent was evaporated. The residue was chromatographed on silica gel eluting with 5% methanol in dichloromethane to give the title compound (160 mg).

MS (APCI): 458 (M+1) for $C_{21}H_{20}N_5O_4SF$

NMR (DMSO-$d_6$) δ: 2.23 (s, 3H); 3.18-3.52 (m, 4H); 3.92 (dd, 1H); 4.30 (t, 1H); 4.69-4.84 (m, 3H); 5.01 (t, 1H); 5.16 (m, 1H); 7.37-7.40 (m, 2H); 7.57-7.67 (m, 2H); 7.84-7.94 (m, 2H).

Example 55

(5R)-3-(3-Fluoro-4-{5-[5-(hydroxymethyl)-4,5-dihydroisoxazol-3-yl]thien-2-yl}phenyl)-5-(hydroxymethyl)-1,3-oxazolidin-2-one

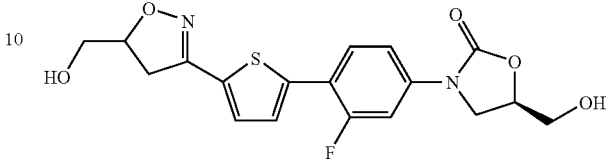

(5R)-3-(3-Fluoro-4-iodophenyl)-5-(hydroxymethyl)-1,3-oxazolidin-2-one (195 mg, 0.58 mM), {3-[5-(trimethylstannyl)thien-2-yl]4,5-dihydroisoxazol-5-yl}methanol (200 mg, 0.58 mM), tris(dibenzylideneacetone) dipalladium (0)-chloroform adduct (60 mg, 0.058 mM) and tri-2-furylphosphine (27 mg, 0.116 mM) were placed in a flask. The solids were degassed and placed under nitrogen. Anhydrous dioxane (5 ml) was added and the suspension was heated at 90° C. for 16 hours. The reaction mixture was cooled and the solvent was evaporated. The residue was chromatographed on silica gel eluting with 5% methanol in dichloromethane to give the title compound (60 mg).

MS (APCI): 393 (M+1) for $C_{18}H_{17}N_2O_5SF$

NMR (DMSO-$d_6$) δ: 3.19-3.72 (m, 9H); 3.88 (dd, 1H); 4.16 (t, 1H); 4.75 (m, 2H); 7.40 (dd, 1H); 7.45 (dd, 1H); 7.56 (d, 1H); 7.63 (dd, 1H); 7.86 (t, 1H).

Example 56

N-({((5S)-3-[4-(5-{5-[(Acetylamino)methyl]-4,5-dihydroisoxazol-3-yl}thien-2-yl)phenyl]-2-oxo-1,3-oxazolidin-5-yl}methyl)acetamide

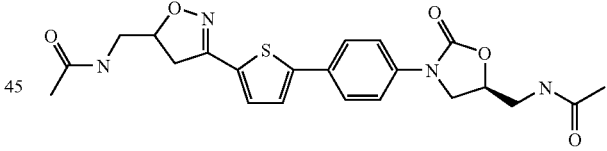

N-({(5S)-2-Oxo-3-[4-(trimethylstannyl)phenyl]-1,3-oxazolidin-5-yl}methyl)acetamide (500 mg, 1.26 mM), N-{[3-(5-bromothien-2-yl)4,5-dihydroisoxazol-5-yl]methyl}acetamide (382 mg, 1.26 mM), tris(dibenzylideneacetone)dipalladium (0)-chloroform adduct (130 mg, 0.126 mM) and tri-2-furylphosphine (58 mg, 0.252 mM) were placed in a flask. The solids were degassed and placed under nitrogen. Anhydrous dioxane (5 ml) was added and the suspension was heated at 90° C. for 5 hours. The reaction mixture was cooled and the solvent was evaporated. The residue was chromatographed on silica gel eluting with 5% methanol in dichloromethane to give the title compound (85 mg).

MS (APCI): 457 (M+1) for $C_{22}H_{24}N_4O_5S$

NMR (DMSO-$d_6$) δ: 1.83 (s, 6H); 3.13-3.52 (m, 6H); 3.80 (dd, 1H); 4.18 (t, 1H); 4.75 (m, 2H); 5.08 (m, 1H); 7.34 (d, 1H); 7.51 (d, 1H); 7.59 (d, 2H); 7.73 (d, 2H); 8.15 (t, 1H); 8.25 (t, 1H).

Example 57

N-(5R)-3-(5-{5-[5-(Hydroxymethyl)-4,5-dihydroisoxazol-3-yl]thien-2-yl}pyrid-2-yl)-2-oxo-1,3-oxazolidin-5-ylmethyl acetamide

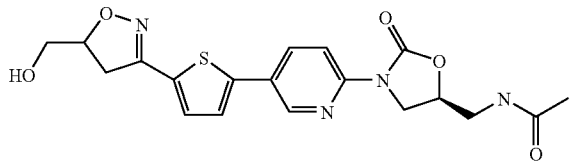

N-{[(5S)-3-(5-Bromopyrid-2-yl)-2-oxo-1,3-oxazolidin-5-yl]methyl}acetamide (181 mg, 0.58 mM), {3-[5-(trimethylstannyl)thien-2-yl]-4,5-dihydroisoxazol-5-yl}methanol (200 mg, 0.58 mM), tris(dibenzylideneacetone)dipalladium (0)-chloroform adduct (60 mg, 0.058 mM) and tri-2-furylphosphine (27 mg, 0.116 mM) were placed in a flask. The solids were degassed and placed under nitrogen. Anhydrous dioxane (5 ml) was added and the suspension was heated at 90° C. for 5 hours. The reaction mixture was cooled and the solvent was evaporated. The residue was chromatographed on silica gel eluting with 5% methanol in dichloromethane to give the title compound (118 mg).

MS (APCI): 417 (M+1) for $C_{19}H_{20}N_4O_5S$

NMR (DMSO-$d_6$) δ: 1.83 (s, 3H); 3.21-3.52 (m, 6H); 3.89 (dd, 1H); 4.24 (t, 1H); 4.76 (m, 2H); 5.03 (m, 1H); 7.40 (d, 1H); 7.60 (d, 1H); 8.15 (m, 2H); 8.26 (t, 1H); 8.74 (m, 1H).

Example 58

(5R)-3-(5-{5-[5-(Hydroxymethyl)-4,5-dihydroisoxazol-3-yl]thien-2-yl}pyrid-2-yl)-5-(1H-1,2,3-triazol-1-ylmethyl)-1,3-oxazolidin-2-one

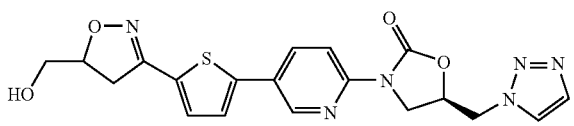

(5R)-3-(5-Bromopyrid-2-yl)-5-(1H-1,2,3-triazol-1-ylmethyl)-1,3-oxazolidin-2-one (187 mg, 0.58 mM), {3-[5-(trimethylstannyl)thien-2-yl]-4,5-dihydroisoxazol-5-yl}methanol (200 mg, 0.58 mM), tris(dibenzylideneacetone)dipalladium (0)-chloroform adduct (60 mg, 0.058 mM) and tri-2-furylphosphine (27 mg, 0.116 mM) were placed in a flask. The solids were degassed and placed under nitrogen. Anhydrous dioxane (5 ml) was added and the suspension was heated at 90° C. for 5 hours. The reaction mixture was cooled and the solvent was evaporated. The residue was chromatographed on silica gel eluting with 5% methanol in dichloromethane to give the title compound (99 mg).

MS (APCI): 427 (M+1) for $C_{19}H_{18}N_6O_4S$

NMR (DMSO-$d_6$) δ: 3.19-3.52 (m, 4H); 4.06 (dd, 1H); 4.34 (t, 1H); 4.75 (m, 1H); 4.87 (d, 2H); 5.02 (m, 1H); 5.17 (m, 1H); 7.40 (d, 1H); 7.59 (d, 1H); 7.76 (s, 1H); 8.03 (d, 1H); 8.14 (d, 1H); 8.16 (s, 1H); 8.74 (d, 1H).

Example 59

(5R)-3-(5-{5-[5-(Hydroxymethyl)-4,5-dihydroisoxazol-3-yl]thien-2-yl}pyrid-2-yl)-5-[(4-methyl-1H-1,2,3-triazol-1-yl)methyl]-1,3-oxazolidin-2-one

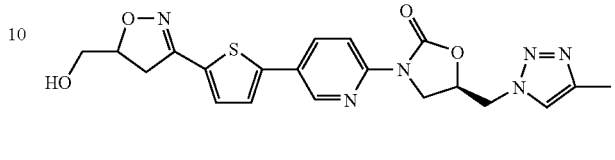

(5R)-3-(5-Bromopyrid-2-yl)-5-[(4-methyl-1H-1,2,3-triazol-1-yl)methyl]-1,3-oxazolidin-2-one (195 mg, 0.58 mM), {3-[5-(trimethylstannyl)thien-2-yl]-4,5-dihydroisoxazol-5-yl}methanol (200 mg, 0.58 mM), tris(dibenzylideneacetone)-dipalladium (0)-chloroform adduct (60 mg, 0.058 mM) and tri-2-furylphosphine (27 mg, 0.116 mM) were placed in a flask. The solids were degassed and placed under nitrogen. Anhydrous dioxane (5 ml) was added and the suspension was heated at 90° C. for 5 hours. The reaction mixture was cooled and the solvent was evaporated. The residue was chromatographed on silica gel eluting with 5% methanol in dichloromethane to give the title compound (72 mg).

MS (APCI): 441 (M+1) for $C_{19}H_{19}N_6O_4S$

NMR (DMSO-$d_6$) δ: 2.22 (s, 3H); 3.19-3.52 (m, 4H); 4.02 (dd, 1H); 4.34 (t, 1H); 4.78 (m, 1H); 4.83 (d, 2H); 5.15 (m, 2H); 7.40 (d, 1H); 7.60 (d, 1H); 7.86 (s, 1H); 8.04 (d, 1H); 8.15 (m, 1H); 8.73 (d, 1H).

Example 60

N-{[(5S)-3-(4-{2-[5-(Hydroxymethyl)-4,5-dihydroisoxazol-3-yl]pyrid-5-yl}phenyl)-2-oxo-1,3-oxazolidin-5-yl]methyl}acetamide

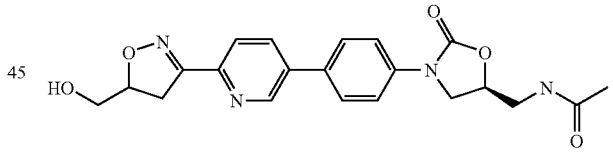

N-({(5S)-2-Oxo-3-[4-(trimethylstannyl)phenyl]-1,3-oxazolidin-5-yl}methyl)acetamide (300 mg, 0.76 mM), [3-(5-bromopyridin-2-yl)-4,5-dihydroisoxazol-5-yl]methanol (194 mg, 0.76 mM), tris(dibenzylideneacetone)dipalladium (0)-chloroform adduct (78 mg, 0.076 mM) and tri-2-furylphosphine (35 mg, 0.152 mM) were placed in a flask. The solids were degassed and placed under nitrogen. Anhydrous dioxane (5 ml) was added and the suspension was heated at 90° C. for 15 hours. The reaction mixture was cooled and the solvent was evaporated. The residue was chromatographed on silica gel eluting with 5% methanol in dichloromethane to give the title compound (83 mg).

MS (APCI): 411 (M+1) for $C_{21}H_{22}N_4O_5$

NMR (DMSO-$d_6$) δ: 1.85 (s, 3H); 3.25-3.58 (m, 6H); 3.81 (dd, 1H); 4.18 (t, 1H); 4.77 (m, 2H); 5.01 (m, 1H); 7.68 (d, 2H); 7.83 (d, 2H); 7.95 (d, 1H); 8.18 (dd, 1H); 8.25 (t, 1H); 8.98 (d, 1H).

Example 61

(5R)-3-(3-Fluoro-4-{2-[5-(hydroxymethyl)-4,5-dihydroisoxazol-3-yl]pyrid-5-yl}phenyl)-5-[(4-methyl-1H-1,2,3-triazol-1-yl)methyl]-1,3-oxazolidin-2-one

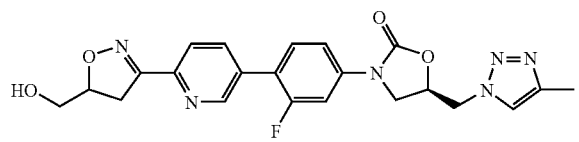

(5R)-3-(3-Fluoro-4-iodophenyl)-5-[(4-methyl-1H-1,2,3-triazol-1-yl)methyl]-1,3-oxazolidin-2-one (236 mg, 0.58 mM), {3-[5-(trimethylstannyl)pyridin-2-yl)-4,5-dihydroisoxazol-5-yl}methanol (200 mg, 0.58 mM), tris(dibenzylideneacetone) dipalladium (0)-chloroform adduct (60 mg, 0.058 mM) and tri-2-furylphosphine (27 mg, 0.116 mM) were placed in a flask. The solids were degassed and placed under nitrogen. Anhydrous dioxane (5 ml) was added and the suspension was heated at 90° C. for 5 hours. The reaction mixture was cooled and the solvent was evaporated. The residue was chromatographed on silica gel eluting with 5% methanol in dichloromethane to give the title compound (70 mg).

MS (APCI): 453 (M+1) for $C_{22}H_{21}N_6O_4F$

NMR (DMSO-$d_6$) δ: 2.23 (s, 3H); 3.25-3.54 (m, 4H); 3.94 (dd, 1H); 4.29 (t, 1H); 4.77 (d, 2H); 4.84 (m, 1H); 5.01 (m, 1H); 5.16 (m, 1H); 7.42 (dd, 1H); 7.58 (dd, 1H); 7.70 (t, 1H); 7.88 (s, 1H); 7.98 (d, 1H); 8.05 (m, 1H); 8.83 (d, 1H).

The intermediate for this compound was prepared as follows:

{3-[5-(Trimethylstannyl)pyrid-2-yl)-4,5-dihydroisoxazol-5-yl}methanol

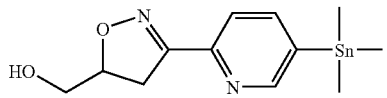

[3-(5-Bromopyrid-2-yl)-4,5-dihydroisoxazol-5-yl]methanol (3.6 g, 14.0 mM) and bis(triphenylphosphine)palladium (II) chloride (982 mg, 1.4 mM) were placed under nitrogen. Anhydrous dioxane (50 ml) was added and the supension was heated at 90° C. Hexamethylditin (5.00 g, 15.4 mM) was added and the resulting solution was stirred at 90° C. for 16 hours. The solution was cooled and the solvent was evaporated. The residue was chromatographed on silica gel eluting with 5% methanol in dichloromethane to give the desired product (2.0 g).

MS (APCI): 341 (M+1) for $C_{12}H_{18}N_2O_2Sn$

NMR (DMSO-$d_6$) δ: 0.33 (s, 9H); 3.36 (dd, 1H); 3.43 (dd, 1H); 3.54 (m, 2H); 4.74 (m, 1H); 4.98 (m, 1H); 7.92 (dd, 1H); 8.10 (dd, 1H); 8.98 (d, 1H).

Example 62

N-{[(5S)-3-(5'-{5-[(Acetylamino)methyl]-2-oxo-1,3-oxazolidin-3-yl}-2,2'-bithien-5-yl)-2-oxo-1,3-oxazolidin-5-yl]methyl}acetamide

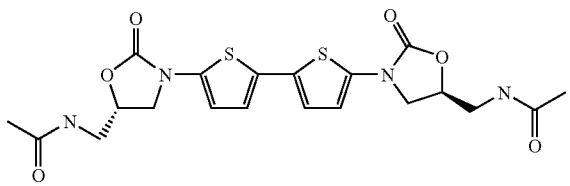

tert-Butyl N-acetyl N-{[(5S)-3-(5-iodothien-2-yl)-2-oxo-1,3-oxazolidin-5-yl]methyl}carbamate (233 mg, 0.50 mM), 4-(trimethylstannyl)pyridine (143 mg, 0.60 mM), dichlorobis (triphenylphosphine)palladium (II) (63 mg, 0.089 mM) and triethylamine (0.170 ml) were placed in a flask. The solids were degassed and placed under nitrogen. Anhydrous dimethylformamide (5 ml) was added and the suspension was heated at 60° C. for 18 hours. The reaction mixture was cooled and the solvent was evaporated. The residue was chromatographed on silica gel eluting with 55% ethylacetate in hexane to give the title compound (51 mg). This compound was dissolved in dichloromethane (5 mL), then treated with trifluoroacetic acid (1 mL). The solution was stirred at room temperature for 1 hour. The solvent was evaporated, and the residue was re-evaporated with dichloromethane to give desired product as a solid (28 mg).

M.P: 257-260° C.

MS (APCI): 479 (M+1) for $C_{20}H_{22}N_4O_6$

NMR (DMSO-$d_6$) δ: 1.46 (s, 3H); 3.06 (br t, 2H); 3.35 (m, 1H); 3.74 (t, 1H); 4.46 (m, 1H); 6.08 (d, 1H); 6.60 (d, 1H); 7.86 (br t, 1H).

The tert-butyl N-acetyl N-{[(5S)-3-(5-iodothien-2-yl)-2-oxo-1,3-oxazolidin-5-yl]methyl}carbamate used in this reaction may be prepared by protection with a tert-butoxycarbonyl group of N-((5S)-[3-(5-iodothien-2-yl)-2-oxo-1,3-oxazolidin-5-yl]methyl) acetamide [Riedl, Bernd; Haebich, Dieter; Stolle, Andreas; Wild, Hanno; Endermann, Rainer; Bremm, Klaus Dieter; Kroll, Hein-Peter; Labischinski, Harald; Schaller, Klaus; Werling, Hans-Otto. Preparation of 3-heteroaryl-2-oxazolidinones as antibacterials. EP 693491 A1 (1996)].

The following example was prepared by a similar procedure to Example 19 above:

Example 63

(5S)-3-{2,2'-Difluoro-4'-[5-(hydroxymethyl)-4,5-dihydroisoxazol-3-yl]-1,1'-biphenyl-4-yl}-5-[(isoxazol-3-ylamino)methyl]-1,3-oxazolidin-2-one

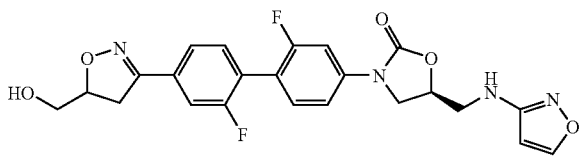

Yield=22 mg

MS (ESP+): (M+H)+ 471.31 for $C_{23}H_{20}F_2N_4O_5$

NMR (DMSO-$d_6$): 3.20 (dd, 1H); 3.41 to 3.52 (m, 4H); 3.57 (dd, 1H); 3.85 (q, 1H); 4.20 (t, 1H); 4.77 (m, 1H); 4.91 (m, 1H); 6.03 (d, 1H); 6.59 (t, 1H); 7.43 (dd, 1H); 7.48 to 7.57 (m, 3H); 7.59 to 7.65 (m, 2H); 8.33 (d, 1H).

Example 64

The following illustrate representative pharmaceutical dosage forms containing a compound of the invention, an in-vivo hydrolysable ester or a pharmaceutically-acceptable salt thereof, including a pharmaceutically-acceptable salt of an in-vivo hydrolysable ester, (hereafter compound X), for therapeutic or prophylactic use in humans:

| (a) | Tablet I | mg/tablet |
|---|---|---|
| | Compound X | 500 |
| | Lactose Ph. Eur | 430 |
| | Croscarmellose sodium | 40 |
| | Polyvinylpyrrolidone | 20 |
| | Magnesium stearate | 10 |
| (b) | Tablet II | mg/tablet |
| | Compound X | 100 |
| | Lactose Ph. Eur | 179 |
| | Croscarmellose sodium | 12 |
| | Polyvinylpyrrolidone | 6 |
| | Magnesium stearate | 3 |
| (c) | Tablet III | mg/tablet |
| | Compound X | 50 |
| | Lactose Ph. Eur | 229 |
| | Croscarmellose sodium | 12 |
| | Polyvinylpyrrolidone | 6 |
| | Magnesium stearate | 3 |
| (d) | Tablet IV | mg/tablet |
| | Compound X | 1 |
| | Lactose Ph. Eur | 92 |
| | Croscarmellose sodium | 4 |
| | Polyvinylpyrrolidone | 2 |
| | Magnesium stearate | 1 |
| (e) | Capsule | mg/capsule |
| | Compound X | 10 |
| | Lactose Ph. Eur | 389 |
| | Croscarmellose sodium | 100 |
| | Magnesium stearate | 1 |
| (f) | Injection I | |
| | Compound X | 50% w/v |
| | Isotonic aqueous solution | to 100% |
| (g) | Injection II (e.g. bolus) | |
| | Compound X | 10% w/v |
| | Isotonic aqueous solution | to 100% |
| (h) | Injection III | |
| | Compound X | 5% w/v |
| | Isotonic aqueous solution | to 100% |
| (i) | Injection IV (e.g. infusion) | |
| | Compound X | 1% w/v |
| | Isotonic aqueous solution | to 100% |

Buffers, pharmaceutically-acceptable surfactants, oils or cosolvents such as polyethylene glycol, polypropylene glycol, glycerol or ethanol, glidants (such as silicon dioxide) or complexing agents such as a cyclodextrin (for example, hydroxypropyl β-cyclodextrin or sulfobutylether β-cyclodextrin) may be used to aid formulation. Also, improvements in aqueous solubility, if desired, may be achieved, for example, by conjugation of a compound of invention with a phospholipid (such as a (phospho)choline derivative) to form a micellar emulsion.

Note: The above formulations may be obtained by conventional procedures well known in the pharmaceutical art, for example as described in "Remington: The Science & Practice of Pharmacy" Vols. I & II (Ed. A. R. Gennaro (Chairman) et al; Publisher: Mack Publishing Company, Easton, Pa.; 19th Edition—1995) and "Pharmaceutics—The Science of Dosage Form Design" (Ed. M. E. Aulton; Publisher: Churchill Livingstone; first published 1988). The tablets (a)-(d) may be (polymer) coated by conventional means, for example to provide an enteric coating of cellulose acetate phthalate.

Example 65

(5R)-3-(3-Fluoro-4-(6-(5-hydroxymethyl-4,5-dihydroisoxazol-3-yl)pyridin-3-yl)phenyl)-5-(1H-1,2,3-triazol-1-ylmethyl)-1,3-oxazolidin-2-one

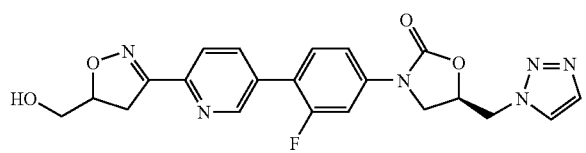

(5R)-3-(3-Fluoro-4-iodophenyl)-5-(1H-1,2,3-triazol-1-ylmethyl)-1,3-oxazolidin-2-one (342 mg, 0.88 mM), {3-[5-(trimethylstannyl)pyridin-2-yl)-4,5-dihydroisoxazol-5-yl}methanol (300 mg, 0.88 mM), tris(dibenzylideneacetone) dipalladium (0)-chloroform adduct (91 mg, 0.088 mM, 0.1 equiv.) and tri-2-furylphosphine (41 mg, 0.176 mM, 0.2 equiv) were placed in a flask. The contents of the flask were degassed and placed under nitrogen. Anhydrous dioxane (5 ml) was added and the mixture was heated at 90° C. for 5 hours and then cooled to room temperature. Solvent was evaporated under reduced pressure and the residue was purified by chromatography (silica gel; elution with 5% methanol in dichloromethane) to give the title compound (170 mg).

MS (APCI): 439 (M+1) for $C_{21}H_{19}N_6O_4F$

NMR (DMSO-$d_6$) δ: 3.42-3.54 (m, 4H); 3.96 (dd, 1H); 4.31 (t, 1H); 4.80 (m, 1H); 4.86 (d, 2H); 5.00 (brs, 1H); 5.20 (m, 1H); 7.41 (dd, 1H); 7.57 (dd, 1H); 7.69 (t, 1H); 7.77 (s, 1H); 7.98-8.07 (m, 2H); 8.19 (s, 1H); 8.82 (brs, 1H).

The invention claimed is:

1. A compound of the formula (I), or a pharmaceutically acceptable salt, prodrug, or in-vivo-hydrolysable ester thereof,

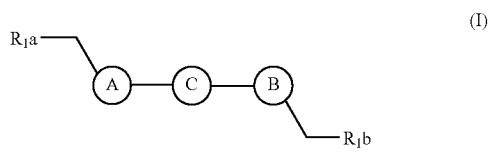

wherein
A and B are i) 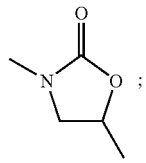

C is a biaryl moiety C'-C"

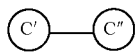

and is represented by the group D below:

D

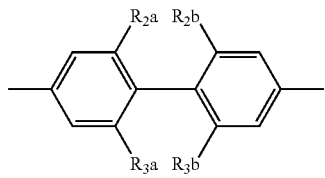

wherein the groups D may be attached to rings A and B in either orientation;
i) is linked as shown in (I) via the 3-position to group C and substituted at the 5-position as shown in (I) by —CH$_2$—R$_1$a and —CH$_2$—R$_1$b;
R$_2$a, R$_2$b, R$_3$a and R$_3$b are independently hydrogen or fluorine;
R$_1$a and R$_1$b are hydroxy.

2. A compound as claimed in claim 1, or a pharmaceutically acceptable salt, prodrug, or in-vivo-hydrolysable ester thereof,
wherein
R$_2$a and R$_2$b are both hydrogen; and
R$_3$a and R$_3$b are both hydrogen or both fluorine.

3. A compound as claimed in claim 1 selected from:
(5R, 5'R)-4,4-bis-(5-hydroxymethyl-2-oxo-oxazolidin-3-yl)-2,2'-difluoro-biphenyl or a pharmaceutically-acceptable salt, or an in-vivo-hydrolysable ester thereof.

4. A method for treating a bacterial infection, comprising administering to a warm-blooded animal in need thereof a compound as claimed in claim 1, or a pharmaceutically acceptable salt, prodrug, or in-vivo hydrolysable ester thereof, wherein the bacteria resulting in the infection is selected from the group consisting of methicillin resistant *staphylococcus*, methicillin resistant coagulase negative *staphylococci, Streptococcus pneumoniae, Streptococcus pyogenes, Haemophilus influenzae* and *Moraxella catarrhalis*.

5. A pharmaceutical composition, which comprises a compound as claimed in claim 1, or a pharmaceutically acceptable salt, prodrug, or an in-vivo hydrolysable ester thereof and a pharmaceutically acceptable diluent or carrier.

6. A process for the preparation of a compound as claimed in claim 1 or a pharmaceutically acceptable salt, prodrug, or an in-vivo hydrolysable ester thereof, which process comprises one of processes (a) to (c):
(a) modifying a substituent in, or introducing a substituent into another compound of the invention by using standard chemistry;
(b) reaction of two molecules of a compound of formula (II) (wherein X is a leaving group useful in palladium coupling) such that an aryl-aryl bond replaces the two aryl-X bonds; or (II)

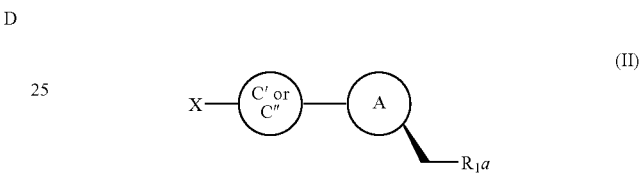

(c) reaction of a biaryl derivative (III) carbamate with an appropriately substituted oxirane to form an oxazolidinone ring (or an equivalent reagent X—CH$_2$CH(O-optionally protected)CH$_2$R$_1$a where X is a displaceable group);

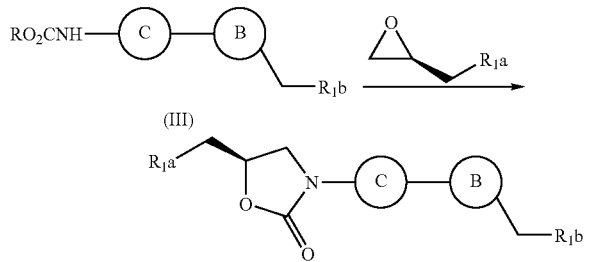

or variations on this process in which the carbamate is replaced by an isocyanate or an amine.

* * * * *